(12) United States Patent
Fauber et al.

(10) Patent No.: US 9,382,222 B2
(45) Date of Patent: Jul. 5, 2016

(54) BENZYL SULFONAMIDE DERIVATIVES AS RORC MODULATORS

(71) Applicant: Genentech, Inc., South San Francisco, CA (US)

(72) Inventors: Benjamin Fauber, San Francisco, CA (US); Olivier Rene, San Francisco, CA (US); Monique Bodil van Niel, Harlow (GB); Simon Gaines, Harlow (GB); Jonathan Killen, Harlow (GB); Stuart Ward, Harlow (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/101,566

(22) Filed: Dec. 10, 2013

(65) Prior Publication Data

US 2014/0163024 A1 Jun. 12, 2014

Related U.S. Application Data

(60) Provisional application No. 61/735,360, filed on Dec. 10, 2012.

(51) Int. Cl.

| | |
|---|---|
| C07D 241/04 | (2006.01) |
| C07D 295/00 | (2006.01) |
| A61K 31/497 | (2006.01) |
| C07D 295/26 | (2006.01) |
| C07D 211/58 | (2006.01) |
| C07D 211/96 | (2006.01) |
| C07D 295/096 | (2006.01) |
| C07D 295/185 | (2006.01) |
| C07D 401/12 | (2006.01) |
| C07D 211/46 | (2006.01) |
| C07D 295/116 | (2006.01) |
| C07D 211/62 | (2006.01) |

(52) U.S. Cl.
CPC ............ *C07D 295/26* (2013.01); *C07D 211/46* (2013.01); *C07D 211/58* (2013.01); *C07D 211/62* (2013.01); *C07D 211/96* (2013.01); *C07D 295/096* (2013.01); *C07D 295/116* (2013.01); *C07D 295/185* (2013.01); *C07D 401/12* (2013.01)

(58) Field of Classification Search
None
See application file for complete search history.

(56) References Cited

FOREIGN PATENT DOCUMENTS

| | | | |
|---|---|---|---|
| WO | WO 2006038594 A1 * | 4/2006 | |
| WO | WO 2008109154 A1 * | 9/2008 | |

OTHER PUBLICATIONS

English Translation of WO 2006/038591 Description 2015.*
English Translation of WO 2006/038591 Claims 2015.*

* cited by examiner

*Primary Examiner* — Jeffrey S Lundgren
*Assistant Examiner* — Michael Schmitt

(57) ABSTRACT

Compounds of the formula Ia or Ib:

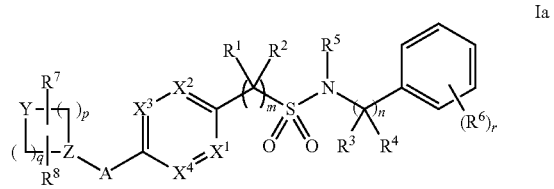

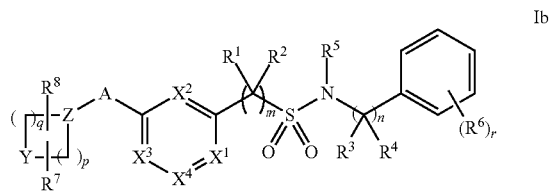

or pharmaceutically acceptable salts thereof,
wherein m, n, p, q, r, A, $X^1$, $X^2$, $X^3$, $X^4$, Y, Z, $R^1$, $R^2$, $R^3$, $R^4$, $R^5$, $R^6$, $R^7$, and $R^8$ are as defined herein. Also disclosed are methods of making the compounds and using the compounds for treatment of inflammatory diseases such as arthritis.

5 Claims, No Drawings

BENZYL SULFONAMIDE DERIVATIVES AS RORC MODULATORS

CROSS REFERENCE TO RELATED APPLICATIONS

This application claims the benefit of priority of U.S. Provisional Patent Application Ser. No. 61/735,360 filed Dec. 10, 2012, the disclosure of which is incorporated herein by reference in their entirety.

FIELD OF THE INVENTION

The invention pertains to compounds that modulate the function of retinoid-receptor related orphan receptor RORc (RORγ) and use of such compounds for treatment of autoimmune diseases.

BACKGROUND OF THE INVENTION

T helper 17 cells (Th17) are interleukin (IL)-17 secreting CD4+ T cells involved in pathogenesis of autoimmune diseases such as rheumatoid arthritis, irritable bowel disease, psoriasis, psoriatic arthritis and spondyloarthridities. The retinoic acid-related orphan receptor γ (RORγ or RORc) is recognized as a transcription factor necessary for Th17 cell differentiation. RORc is an orphan member of the nuclear hormone receptor subfamily that includes RORα (RORa) and RORβ (RORb). RORc controls gene transcription by binding to DNA as a monomer. Selective modulation of RORc has been proposed as a route to discovery and development of Th17 cell-associated autoimmune diseases.

There is accordingly a need for compounds that inhibit RORc for use in treatment of autoimmune diseases such as rheumatoid arthritis, irritable bowel disease, psoriasis, psoriatic arthritis and spondyloarthridities.

SUMMARY OF THE INVENTION

The invention provides compounds of formula Ia or Ib:

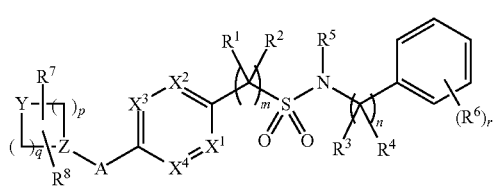

Ia

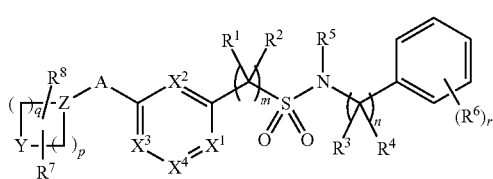

Ib or a pharmaceutically acceptable salt thereof,
wherein:
  m is 0 or 1;
  n is 0 or 1;
  p is 1 or 2;
  q is from 1 to 3;
  r is from 0 to 3;
  A is: a bond; —$CH_2$—; =CH—; —CH(OH)—; —C(O)—; —C(O)—NH—; —NH—(O)C—; —$NR^a$—; —O—; —S—; or —$SO_2$—;

one or two of $X^1$, $X^2$, $X^3$ and $X^4$ is N and the others are $CR^b$; or three of $X^1$, $X^2$, $X^3$ and $X^4$ are N and the other is $CR^b$; or each of $X^1$, $X^2$, $X^3$ and $X^4$ is $CR^b$;
  Y is: —O—; —S—; —$SO_2$—; —$CR^cR^d$—; or —$NR^e$—;
  Z is $CR^f$ or N;
  $R^1$, $R^2$, $R^3$ and $R^4$ each independently is: hydrogen; or $C_{1-6}$alkyl which may be unsubstituted or substituted one or more times with halo;
  $R^5$ is: $C_{1-6}$alkyl; $C_{3-6}$cycloalkyl; $C_{3-6}$cycloalkyl-$C_{1-6}$alkyl; $C_{1-6}$alkoxy-$C_{1-6}$alkyl; or hydroxy-$C_{1-6}$alkyl, wherein the $C_{1-6}$alkyl and $C_{3-6}$cycloalkyl moieties may be substituted one or more times with halo;
  each $R^6$ is independently: $C_{1-6}$alkyl; halo; $C_{1-6}$alkoxy; or cyano; wherein the $C_{1-6}$alkyl moieties may be unsubstituted or substituted one or more times with halo;
  $R^7$ is: hydrogen; $C_{1-6}$alkyl; hydroxy; or halo;
  $R^8$ is: hydrogen; $C_{1-6}$alkyl; halo; hydroxy; or oxo;
  or $R^7$ and $R^8$ together with the atoms to which they are attached may form a four, five, six or seven membered ring;
  each $R^9$ is independently: halo; hydroxy; $C_{1-6}$alkoxy; $C_{1-6}$alkylsulfonyl; amino; $C_{1-6}$alkyl-amino; di-$C_{1-6}$alkyl-amino; cyano; or oxo;
  $R^a$ is: hydrogen; or $C_{1-6}$alkyl;
  each $R^b$ is independently: hydrogen; $C_{1-6}$alkyl; halo; $C_{1-6}$alkoxy; or cyano; wherein the $C_{1-6}$alkyl moieties may be unsubstituted or substituted one or more times with halo;
  $R^c$ is: hydrogen; halo; or $C_{1-6}$alkyl which may be unsubstituted or substituted one or more times with halo;
  $R^d$ is: hydrogen; $C_{1-6}$alkyl; $C_{3-6}$cycloalkyl; $C_{3-6}$cycloalkyl-$C_{1-6}$alkyl; halo; $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-amino carbonyl; N,N-di-$C_{1-6}$alkyl-amino carbonyl; aminosulfonyl; N—$C_{1-6}$alkyl-amino sulfonyl; N,N-di-$C_{1-6}$alkyl-aminosulfonyl; cyano; $C_{1-6}$alkoxy; $C_{1-6}$alkyl-sulfonylamino; amino; N—$C_{1-6}$alkyl-amino; N,N-di-$C_{1-6}$alkyl-amino; halo-$C_{1-6}$alkyl; or hydroxyl; wherein the $C_{1-6}$alkyl moieties may be unsubstituted or substituted one or more times with halo; and wherein the $C_{3-6}$cycloalkyl, and $C_{3-6}$cycloalkyl-$C_{1-6}$alkyl moieties may be unsubstituted or substituted one or more times with $R^9$;
  or $R^c$ and $R^d$ together with the atoms to which they are attached may form a four, five, six or seven membered ring that optionally includes a hetereoatom selected from O, N and S;
  $R^e$ is: hydrogen; $C_{1-6}$alkyl; $C_{3-6}$cycloalkyl; $C_{3-6}$cycloalkyl-$C_{1-6}$alkyl; $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-amino carbonyl; N,N-di-$C_{1-6}$alkyl-amino carbonyl; aminosulfonyl; N—$C_{1-6}$alkyl-amino sulfonyl; or N,N-di-$C_{1-6}$alkyl-aminosulfonyl; wherein the $C_{1-6}$alkyl moieties may be unsubstituted or substituted one or more times with halo; and wherein the $C_{3-6}$cycloalkyl, and $C_{3-6}$cycloalkyl-$C_{1-6}$alkyl moieties may be unsubstituted or substituted one or more times with $R^9$;
  or $R^e$ and $R^7$ together with the atoms to which they are attached may form a four, five, six or seven membered ring; and
  $R^f$ is: hydrogen; hydroxyl; or $C_{1-6}$alkyl which may be unsubstituted or substituted one or more times with halo, or $R^f$ is absent when A is =CH—.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy' means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —$SO_2$—R, wherein R is alkyl as defined herein.

"Alkylsulfonylalkyl means a moiety of the formula —R'—$SO_2$—R" where R' is alkylene and R" is alkyl as defined herein.

"Alkylsulfonylalkoxy" means a group of the formula —O—R—$SO_2$—R' wherein R is alkylene and R' is alkyl as defined herein.

"Amino means a moiety of the formula —NRR' wherein R and R' each independently is hydrogen or alkyl as defined herein. "Amino thus includes" alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, of which may be optionally substituted as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" "means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted as defined herein. Unless defined otherwise, cycloalkyl may be optionally substituted with one or more substituents, wherein each substituent is independently hydroxy, alkyl, alkoxy, halo, haloalkyl, amino, monoalkylamino, or dialkylamino. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, each of which may be optionally substituted as defined herein.

Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, morpholinyl, thiomorpholinyl, azepinyl, pyrrolidinyl, azetidinyl, tetrahydropyranyl, tetrahydrofuranyl, oxetanyl and the like. Such heterocyclyl may be optionally substituted as defined herein.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Oxo" means a group of the formula =O (i.e., an oxygen with a double bond). Thus, for example, a 1-oxo-ethyl group is an acetyl group.

"Alkoxy hydroxyalkyl" and "hydroxy alkoxyalkyl", which may be used interchangeably, means an alkyl as defined herein that is substituted at least once with hydroxy and at least once with alkoxy. "Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R''' wherein R', R" and R''' each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted" when used in association with an "aryl", phenyl", "heteroaryl" "cycloalkyl" or "heterocyclyl" moiety means that such moiety may be unsubstituted (i.e., all open valencies are occupied by a hydrogen atom) or substituted with specific groups as related herein.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "aminoprotecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H$_2$O, such combination being able to form one or more hydrate.

"Arthritis" means a disease or condition that causes damage to joints of the body and pain associated with such joint damage. Arthritis includes rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

"Respiratory disorder" refers to, without limitation, chronic obstructive pulmonary disease (COPD), asthma, bronchospasm, and the like.

"Gastrointestinal disorder" ("GI disorder") refers to, without limitation, Irritable Bowel Syndrome (IBS), Inflammatory Bowel Disease (IBD), biliary colic and other biliary disorders, renal colic, diarrhea-dominant IBS, pain associated with GI distension, and the like.

"Pain" includes, without limitation, inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature and chemical names used in this application are based on ChembioOffice™ by CambridgeSoft™. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes. One or more carbon atom(s) of a compound of the invention may be replaced by a silicon atom(s), and it is contemplated that one or more oxygen atom(s) of a compound of the invention may be replaced by a sulfur or selenium atom(s).

Compounds of the Invention

The invention provides compounds of the formula Ia or Ib:

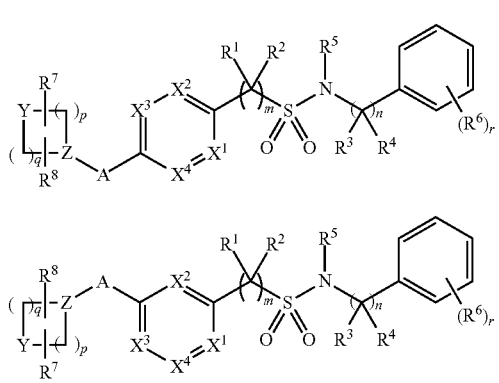

or a pharmaceutically acceptable salt thereof,
wherein:
  m is 0 or 1;
  n is 0 or 1;
  p is 1 or 2;
  q is from 1 to 3;
  r is from 0 to 3;
  A is: a bond; —CH$_2$—; =CH—; —CH(OH)—; —C(O)—; —C(O)—NH—; —NH—(O)C—; —NR$^a$—; —O—; —S—; or —SO$_2$—;
  one or two of $X^1$, $X^2$, $X^3$ and $X^4$ is N and the others are CR$^b$; or three of $X^1$, $X^2$, $X^3$ and $X^4$ are N and the other is CR$^b$; or each of $X^1$, $X^2$, $X^3$ and $X^4$ is CR$^b$;
  Y is: —O—; —S—; —SO$_2$—; —CR$^c$R$^d$—; or —NR$^e$—;
  Z is CR$^f$ or N;
  $R^1$, $R^2$, $R^3$ and $R^4$ each independently is: hydrogen; or C$_{1-6}$alkyl which may be unsubstituted or substituted one or more times with halo;
  $R^5$ is: C$_{1-6}$alkyl; C$_{3-6}$cycloalkyl; C$_{3-6}$cycloalkyl-C$_{1-6}$alkyl; C$_{1-6}$alkoxy-C$_{1-6}$alkyl; or hydroxy-C$_{1-6}$alkyl, wherein the C$_{1-6}$alkyl, C$_{3-6}$cycloalkyl and C$_{3-6}$cycloalkyl-C$_{1-6}$alkyl moities may be substituted one or more times with halo;
  each $R^6$ is independently: C$_{1-6}$alkyl; halo; C$_{1-6}$alkoxy; or cyano; wherein the C$_{1-6}$alkyl moieties may be unsubstituted or substituted one or more times with halo;
  $R^7$ is: hydrogen; C$_{1-6}$alkyl; hydroxy; or halo;
  $R^8$ is: hydrogen; C$_{1-6}$alkyl; halo; hydroxy; or oxo;
  or $R^7$ and $R^8$ together with the atoms to which they are attached may form a four, five, six or seven membered ring;
  each $R^9$ is independently: halo; hydroxy; C$_{1-6}$alkoxy; C$_{1-6}$alkylsulfonyl; amino; C$_{1-6}$alkyl-amino; di-C$_{1-6}$alkyl-amino; cyano; or oxo;
  $R^a$ is: hydrogen; or C$_{1-6}$alkyl;
  each $R^b$ is independently: hydrogen; C$_{1-6}$alkyl; halo; C$_{1-6}$alkoxy; or cyano; wherein the C$_{1-6}$alkyl moieties may be unsubstituted or substituted one or more times with halo;
  $R^c$ is: hydrogen; halo; or C$_{1-6}$alkyl which may be unsubstituted or substituted one or more times with halo;
  $R^d$ is: hydrogen; C$_{1-6}$alkyl; C$_{3-6}$cycloalkyl; C$_{3-6}$cycloalkyl-C$_{1-6}$alkyl; halo; C$_{1-6}$alkyl-carbonyl; C$_{3-6}$cycloalkyl-carbonyl; C$_{3-6}$cycloalkyl-C$_{1-6}$alkyl-carbonyl; C$_{1-6}$alkyl-sulfonyl; C$_{3-6}$cycloalkyl-sulfonyl; C$_{3-6}$cycloalkyl-C$_{1-6}$alkyl-sulfonyl; aminocarbonyl; N—C$_{1-6}$alkyl-amino carbonyl; N,N-di-C$_{1-6}$alkyl-amino carbonyl; aminosulfonyl; N—C$_{1-6}$alkyl-amino sulfonyl; N,N-di-C$_{1-6}$alkyl-amino sulfonyl; cyano; C$_{1-6}$alkoxy; C$_{1-6}$alkyl-sulfonylamino; amino; N—C$_{1-6}$alkyl-amino; N,N-di-C$_{1-6}$alkyl-amino; halo-C$_{1-6}$alkyl; or hydroxyl; wherein the C$_{1-6}$alkyl moieties may be unsubstituted or substituted one or more times with halo; and wherein the C$_{3-6}$cycloalkyl, and C$_{3-6}$cycloalkyl-C$_{1-6}$alkyl moieties may be unsubstituted or substituted one or more times with $R^9$;
  or $R^c$ and $R^d$ together with the atoms to which they are attached may form a four, five, six or seven membered ring that optionally includes a hetereoatom selected from O, N and S;
  $R^e$ is: hydrogen; C$_{1-6}$alkyl; C$_{3-6}$cycloalkyl; C$_{3-6}$cycloalkyl-C$_{1-6}$alkyl; C$_{1-6}$alkyl-carbonyl; C$_{3-6}$cycloalkyl-carbonyl; C$_{3-6}$cycloalkyl-C$_{1-6}$alkyl-carbonyl; C$_{1-6}$alkyl-sulfonyl; C$_{3-6}$cycloalkyl-sulfonyl; C$_{3-6}$cycloalkyl-C$_{1-6}$alkyl-sulfonyl; aminocarbonyl; N—C$_{1-6}$alkyl-amino carbonyl; N,N-di-C$_{1-6}$alkyl-amino carbonyl; aminosulfonyl; N—C$_{1-6}$alkyl-amino sulfonyl; or N,N-di-C$_{1-6}$alkyl-aminosulfonyl; wherein the C$_{1-6}$alkyl moieties may be unsubstituted or substituted one or more times with halo; and wherein the C$_{3-6}$cycloalkyl, and C$_{3-6}$cycloalkyl-C$_{1-6}$alkyl moieties may be unsubstituted or substituted one or more times with $R^9$;
  or $R^e$ and $R^7$ together with the atoms to which they are attached may form a four, five, six or seven membered ring; and
  $R^f$ is: hydrogen; hydroxyl; or C$_{1-6}$alkyl which may be unsubstituted or substituted one or more times with halo, or $R^f$ is absent when A is =CH—.

In certain embodiments, the compounds of the invention are of formula Ia.

In certain embodiments, the compounds of the invention are of formula Ib.

In certain embodiments of formula Ia or Ib, when A is =CH—, —NR$^a$—, —O—, or —S—, then Z is CR$^f$.

In certain embodiments of formula Ia or Ib, when A is =CH—, then R$^f$ is absent.

In certain embodiments of formula Ia or Ib, m is 0.
In certain embodiments of formula Ia or Ib, m is 1.
In certain embodiments of formula Ia or Ib, n is 0.
In certain embodiments of formula Ia or Ib, n is 1.
In certain embodiments of formula Ia or Ib, p is 1.
In certain embodiments of formula Ia or Ib, p is 2.
In certain embodiments of formula Ia or Ib, q is 1 or 2.
In certain embodiments of formula Ia or Ib, q is 2 or 3.
In certain embodiments of formula Ia or Ib, q is 1.
In certain embodiments of formula Ia or Ib, q is 2.
In certain embodiments of formula Ia or Ib, q is 3.
In certain embodiments of formula Ia or Ib, r is from 0 to 2.
In certain embodiments of formula Ia or Ib, r is 0 or 1.
In certain embodiments of formula Ia or Ib, r is 0.
In certain embodiments of formula Ia or Ib, r is 1.
In certain embodiments of formula Ia or Ib, r is 2.
In certain embodiments of formula Ia or Ib, r is 3.
In certain embodiments of formula Ia or Ib, A is a bond; —CH$_2$—; —C(O)—, —NR$^a$—; —O—; —S—; or —SO$_2$—.
In certain embodiments of formula Ia or Ib, A is a bond; —NR$^a$—; —O—; —S—; or —SO$_2$—.
In certain embodiments of formula Ia or Ib, A is a bond; —NR$^a$—; or —O—.
In certain embodiments of formula Ia or Ib, A is a bond.
In certain embodiments of formula Ia or Ib, A is —CH$_2$—.
In certain embodiments of formula Ia or Ib, A is =CH—.
In certain embodiments of formula Ia or Ib, A is —C(O)—.
In certain embodiments of formula Ia or Ib, A is —CH(OH)—.
In certain embodiments of formula Ia or Ib, A is —NR$^a$—.
In certain embodiments of formula Ia or Ib, A is —O—.
In certain embodiments of formula Ia or Ib, A is —S—.
In certain embodiments of formula Ia or Ib, A is —SO$_2$—.
In certain embodiments of formula Ia or Ib, A is —NH—(O)C—.
In certain embodiments of formula Ia or Ib, one or two of $X^1$, $X^2$, $X^3$ and $X^4$ is N and the others are CR$^b$.
In certain embodiments of formula Ia or Ib, three of $X^1$, $X^2$, $X^3$ and $X^4$ are N and the other is CR$^b$.
In certain embodiments of formula Ia or Ib, each of $X^1$, $X^2$, $X^3$ and $X^4$ is CR$^b$.
In certain embodiments of formula Ia or Ib, one of $X^1$, $X^2$, $X^3$ and $X^4$ is N and the other is CR$^b$.
In certain embodiments of formula Ia or Ib, two of $X^1$, $X^2$, $X^3$ and $X^4$ are N and the others are CR$^b$.
In certain embodiments of formula Ia or Ib, $X^1$ is N and $X^2$, $X^3$ and $X^4$ are CR$^b$.
In certain embodiments of formula Ia or Ib, $X^4$ is N and $X^1$, $X^2$ and $X^3$ are CR$^b$.
In certain embodiments of formula Ia or Ib, $X^1$ and $X^2$ are N and $X^3$ and $X^4$ are CR$^b$.
In certain embodiments of formula Ia or Ib, $X^3$ and $X^4$ are N and $X^1$ and $X^2$ are CR$^b$.
In certain embodiments of formula Ia or Ib, $X^2$ and $X^4$ are N and $X^1$ and $X^3$ are CR$^b$.
In certain embodiments of formula Ia or Ib, $X^1$ and $X^4$ are N and $X^2$ and $X^3$ are CR$^b$.
In certain embodiments of formula Ia or Ib, Y is —O—; —CR$^c$R$^d$—; or —NR$^e$—.
In certain embodiments of formula Ia or Ib, Y is —CR$^c$R$^d$—; or —NR$^e$—.
In certain embodiments of formula Ia or Ib, Y is —O—.
In certain embodiments of formula Ia or Ib, Y is —S—.
In certain embodiments of formula Ia or Ib, Y is —SO$_2$—.
In certain embodiments of formula Ia or Ib, Y is —CR$^c$R$^d$—.
In certain embodiments of formula Ia or Ib, Y is —NR$^e$—.

In certain embodiments of formula Ia or Ib, Z is CR$^f$.
In certain embodiments of formula Ia or Ib, Z is N.
In certain embodiments of formula Ia or Ib, Z is CH.
In certain embodiments of formula Ia or Ib, $R^1$, $R^2$, $R^3$ and $R^4$ are hydrogen.
In certain embodiments of formula Ia or Ib, $R^1$ is hydrogen.
In certain embodiments of formula Ia or Ib, $R^1$ is $C_{1-6}$alkyl which may be unsubstituted or substituted one or more times with halo.
In certain embodiments of formula Ia or Ib, $R^1$ is $C_{1-6}$alkyl.
In certain embodiments of formula Ia or Ib, $R^2$ is hydrogen.
In certain embodiments of formula Ia or Ib, $R^2$ is $C_{2-6}$alkyl which may be unsubstituted or substituted one or more times with halo.
In certain embodiments of formula Ia or Ib, $R^2$ is $C_{2-6}$alkyl.
In certain embodiments of formula Ia or Ib, $R^3$ is hydrogen.
In certain embodiments of formula Ia or Ib, $R^3$ is $C_{3-6}$alkyl which may be unsubstituted or substituted one or more times with halo.
In certain embodiments of formula Ia or Ib, $R^3$ is $C_{3-6}$alkyl.
In certain embodiments of formula Ia or Ib, $R^4$ is hydrogen.
In certain embodiments of formula Ia or Ib, $R^4$ is $C_{4-6}$alkyl which may be unsubstituted or substituted one or more times with halo.
In certain embodiments of formula Ia or Ib, $R^4$ is $C_{4-6}$alkyl.
In certain embodiments of formula Ia or Ib, $R^5$ is: $C_{1-6}$alkyl; $C_{3-6}$cycloalkyl; or $C_{3-6}$cycloalkyl-$C_{1-6}$alkyl wherein the $C_{1-6}$alkyl and $C_{3-6}$cycloalkyl portions may be substituted one or more times with halo.
In certain embodiments of formula Ia or Ib, $R^5$ is $C_{1-6}$alkyl.
In certain embodiments of formula Ia or Ib, $R^5$ is halo-$C_{1-6}$alkyl.
In certain embodiments of formula Ia or Ib, $R^5$ is $C_{3-6}$cycloalkyl.
In certain embodiments of formula Ia or Ib, $R^5$ is $C_{3-6}$cycloalkyl-$C_{1-6}$alkyl.
In certain embodiments of formula Ia or Ib, $R^5$ is $C_{1-6}$alkoxy-$C_{1-6}$alkyl.
In certain embodiments of formula Ia or Ib, $R^5$ is hydroxy-$C_{1-6}$alkyl.
In certain embodiments of formula Ia or Ib, each $R^6$ is independently: $C_{1-6}$alkyl; halo-$C_{1-6}$alkyl; halo; $C_{1-6}$alkoxy; or cyano.
In certain embodiments of formula Ia or Ib, each $R^6$ is independently: $C_{1-6}$alkyl; halo-$C_{1-6}$alkyl; or halo.
In certain embodiments of formula Ia or Ib, $R^6$ is $C_{1-6}$alkyl.
In certain embodiments of formula Ia or Ib, $R^6$ is halo.
In certain embodiments of formula Ia or Ib, $R^6$ is $C_{1-6}$alkoxy.
In certain embodiments of formula Ia or Ib, $R^6$ is cyano.
In certain embodiments of formula Ia or Ib, $R^6$ is halo or trifluoromethyl.
In certain embodiments of formula Ia or Ib, $R^7$ and $R^8$ are hydrogen.
In certain embodiments of formula Ia or Ib, $R^7$ is hydrogen or $C_{1-6}$alkyl.
In certain embodiments of formula Ia or Ib, $R^7$ is hydrogen.
In certain embodiments of formula Ia or Ib, $R^7$ is $C_{1-6}$alkyl.
In certain embodiments of formula Ia or Ib, $R^7$ is hydroxyl.
In certain embodiments of formula Ia or Ib, $R^7$ is halo.
In certain embodiments of formula Ia or Ib, $R^8$ is hydrogen or $C_{1-6}$alkyl.
In certain embodiments of formula Ia or Ib, $R^8$ is hydrogen.
In certain embodiments of formula Ia or Ib, $R^8$ is $C_{1-6}$alkyl.
In certain embodiments of formula Ia or Ib, $R^8$ is halo.
In certain embodiments of formula Ia or Ib, $R^8$ is hydroxyl.
In certain embodiments of formula Ia or Ib, $R^8$ is oxo.

In certain embodiments of formula Ia or Ib, $R^7$ and $R^8$ together with the atoms to which they are attached form a four, five, six or seven membered ring.

In certain embodiments of formula Ia or Ib, each $R^9$ is independently: halo; amino; $C_{1-6}$alkyl-amino; di-$C_{1-6}$alkyl; -amino; or oxo.

In certain embodiments of formula Ia or Ib, $R^9$ is halo.

In certain embodiments of formula Ia or Ib, $R^9$ is hydroxyl.

In certain embodiments of formula Ia or Ib, $R^9$ is $C_{1-6}$alkoxy.

In certain embodiments of formula Ia or Ib, $R^9$ is $C_{1-6}$alkyl-sulfonyl.

In certain embodiments of formula Ia or Ib, $R^9$ is amino.

In certain embodiments of formula Ia or Ib, $R^9$ is $C_{1-6}$alkyl-amino.

In certain embodiments of formula Ia or Ib, $R^9$ is di-$C_{1-6}$alkyl; -amino.

In certain embodiments of formula Ia or Ib, $R^9$ is cyano.

In certain embodiments of formula Ia or Ib, $R^9$ is or oxo.

In certain embodiments of formula Ia or Ib, $R^a$ is hydrogen.

In certain embodiments of formula Ia or Ib, $R^a$ is $C_{1-6}$alkyl.

In certain embodiments of formula Ia or Ib, $R^c$ and $R^d$ are hydrogen.

In certain embodiments of formula Ia or Ib, each $R^b$ is independently: hydrogen; $C_{1-6}$alkyl; halo-$C_{1-6}$alkyl; or halo.

In certain embodiments of formula Ia or Ib, each $R^b$ is independently hydrogen, halo, or halo-$C_{1-6}$alkyl.

In certain embodiments of formula Ia or Ib, $R^b$ is hydrogen.

In certain embodiments of formula Ia or Ib, $R^b$ is halo.

In certain embodiments of formula Ia or Ib, $R^c$ is: hydrogen; halo; $C_{1-6}$alkyl; or halo-$C_{1-6}$alkyl.

In certain embodiments of formula Ia or Ib, $R^c$ is hydrogen.

In certain embodiments of formula Ia or Ib, $R^c$ is halo.

In certain embodiments of formula Ia or Ib, $R^c$ is $C_{1-6}$alkyl.

In certain embodiments of formula Ia or Ib, $R^c$ is halo-$C_{1-6}$alkyl.

In certain embodiments of formula Ia or Ib, $R^d$ is: hydrogen; $C_{1-6}$alkyl; $C_{3-6}$cycloalkyl; $C_{3-6}$cycloalkyl-$C_{1-6}$alkyl; halo; $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-amino carbonyl; N,N-di-$C_{1-6}$alkyl-amino carbonyl; aminosulfonyl; N—$C_{1-6}$alkyl-amino sulfonyl; N,N-di-$C_{1-6}$alkyl-amino sulfonyl; cyano; $C_{1-6}$alkoxy; $C_{1-6}$alkyl-sulfonylamino; amino; N—$C_{1-6}$alkyl-amino; N,N-di-$C_{1-6}$alkyl-amino; hydroxyl; or halo-$C_{1-6}$alkyl.

In certain embodiments of formula Ia or Ib, $R^d$ is: aminocarbonyl; N—$C_{1-6}$alkyl-amino carbonyl; N,N-di-$C_{1-6}$alkyl-amino carbonyl; aminosulfonyl; N—$C_{1-6}$alkyl-amino sulfonyl; N,N-di-$C_{1-6}$alkyl-aminosulfonyl; or $C_{1-6}$alkyl-sulfonylamino.

In certain embodiments of formula Ia or Ib, $R^d$ is hydrogen.

In certain embodiments of formula Ia or Ib, $R^d$ is $C_{1-6}$alkyl.

In certain embodiments of formula Ia or Ib, $R^d$ is $C_{3-6}$cycloalkyl.

In certain embodiments of formula Ia or Ib, $R^d$ is $C_{3-6}$cycloalkyl-$C_{1-6}$alkyl.

In certain embodiments of formula Ia or Ib, $R^d$ is halo.

In certain embodiments of formula Ia or Ib, $R^d$ is $C_{1-6}$alkyl-carbonyl.

In certain embodiments of formula Ia or Ib, $R^d$ is $C_{3-6}$cycloalkyl-carbonyl.

In certain embodiments of formula Ia or Ib, $R^d$ is $C_{3-6}$cycloalkyl-$C_{1-6}$alkyl-carbonyl.

In certain embodiments of formula Ia or Ib, $R^d$ is $C_{1-6}$alkyl-sulfonyl.

In certain embodiments of formula Ia or Ib, $R^d$ is $C_{3-6}$cycloalkyl-sulfonyl.

In certain embodiments of formula Ia or Ib, $R^d$ is $C_{3-6}$cycloalkyl-$C_{1-6}$alkyl-sulfonyl.

In certain embodiments of formula Ia or Ib, $R^d$ is aminocarbonyl.

In certain embodiments of formula Ia or Ib, $R^d$ is N—$C_{1-6}$alkyl-aminocarbonyl.

In certain embodiments of formula Ia or Ib, $R^d$ is N,N-di-$C_{1-6}$alkyl-aminocarbonyl.

In certain embodiments of formula Ia or Ib, $R^d$ is aminosulfonyl.

In certain embodiments of formula Ia or Ib, $R^d$ is N—$C_{1-6}$alkyl-aminosulfonyl.

In certain embodiments of formula Ia or Ib, $R^d$ is N,N-di-$C_{1-6}$alkyl-aminosulfonyl.

In certain embodiments of formula Ia or Ib, $R^d$ is cyano.

In certain embodiments of formula Ia or Ib, $R^d$ is $C_{1-6}$alkoxy.

In certain embodiments of formula Ia or Ib, $R^d$ is $C_{1-6}$alkyl-sulfonylamino.

In certain embodiments of formula Ia or Ib, $R^d$ is amino.

In certain embodiments of formula Ia or Ib, $R^d$ is N—$C_{1-6}$alkyl-amino. In certain embodiments of formula Ia or Ib, $R^d$ is N,N-di-$C_{1-6}$alkyl-amino.

In certain embodiments of formula Ia or Ib, $R^d$ is halo-$C_{1-6}$alkyl.

In certain embodiments of formula Ia or Ib, $R^d$ is hydroxyl.

In certain embodiments of formula Ia or Ib, $R^c$ and $R^d$ together with the atoms to which they are attached form a four, five, six or seven membered ring that optionally includes a hetereoatom selected from O, N and S.

In certain embodiments of formula Ia or Ib, $R^e$ is: $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-amino carbonyl; N,N-di-$C_{1-6}$alkyl-amino carbonyl; aminosulfonyl; N—$C_{1-6}$alkyl-amino sulfonyl; or N,N-di-$C_{1-6}$alkyl-aminosulfonyl.

In certain embodiments of formula Ia or Ib, $R^e$ is hydrogen.

In certain embodiments of formula Ia or Ib, $R^e$ is $C_{1-6}$alkyl.

In certain embodiments of formula Ia or Ib, $R^e$ is $C_{3-6}$cycloalkyl.

In certain embodiments of formula Ia or Ib, $R^e$ is $C_{3-6}$cycloalkyl-$C_{1-6}$alkyl.

In certain embodiments of formula Ia or Ib, $R^e$ is $C_{1-6}$alkyl-carbonyl.

In certain embodiments of formula Ia or Ib, $R^e$ is $C_{3-6}$cycloalkyl-carbonyl.

In certain embodiments of formula Ia or Ib, $R^e$ is $C_{3-6}$cycloalkyl-$C_{1-6}$alkyl-carbonyl.

In certain embodiments of formula Ia or Ib, $R^e$ is $C_{1-6}$alkyl-sulfonyl.

In certain embodiments of formula Ia or Ib, $R^e$ is $C_{3-6}$cycloalkyl-sulfonyl.

In certain embodiments of formula Ia or Ib, $R^e$ is $C_{3-6}$cycloalkyl-$C_{1-6}$alkyl-sulfonyl.

In certain embodiments of formula Ia or Ib, $R^e$ is aminocarbonyl. In certain embodiments of formula Ia or Ib, $R^e$ is N—$C_{1-6}$alkyl-aminocarbonyl.

In certain embodiments of formula Ia or Ib, $R^e$ is N,N-di-$C_{1-6}$alkyl-aminocarbonyl.

In certain embodiments of formula Ia or Ib, $R^e$ is aminosulfonyl.

In certain embodiments of formula Ia or Ib, $R^e$ is N—$C_{1-6}$alkyl-aminosulfonyl.

In certain embodiments of formula Ia or Ib, $R^e$ is N,N-di-$C_{1-6}$alkyl-aminosulfonyl.

In certain embodiments of formula Ia or Ib, $R^e$ and $R^7$ together with the atoms to which they are attached form a four, five, six or seven membered ring.

In certain embodiments of formula Ia or Ib, $R^f$ is hydrogen.

In certain embodiments of formula Ia or Ib, $R^f$ is $C_{1-6}$alkyl.

In certain embodiments of formula Ia or Ib, $R^f$ is hydrogen or $C_{1-6}$alkyl.

In certain embodiments of formula Ia or Ib, $R^f$ is hydroxyl.

In certain embodiments of formula Ia or Ib, $R^f$ is absent.

In certain embodiments of formula Ia, the subject compounds may be of formulas IIa through IIg:

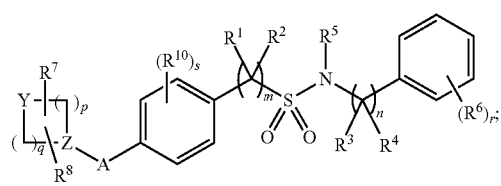
IIa

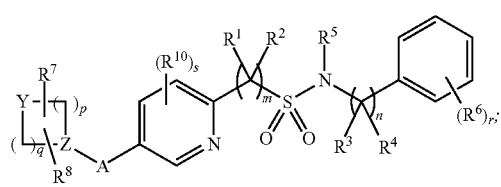
IIb

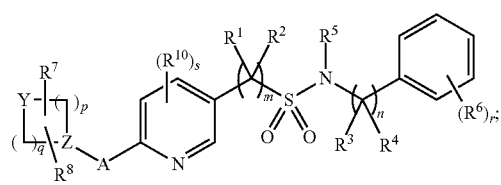
IIc

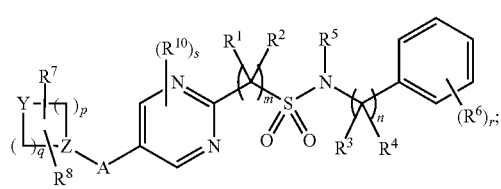
IId

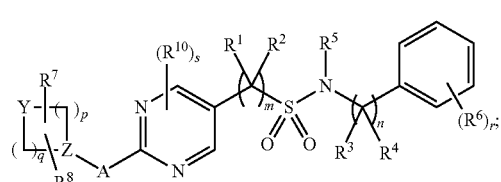
IIe

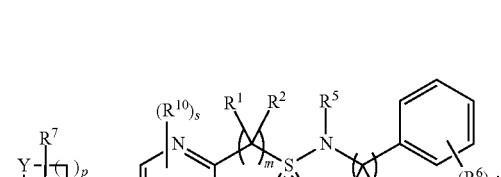
IIf

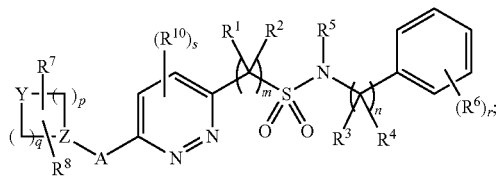
IIg or pharmaceutically acceptable salts thereof, wherein:

s is from 0 to 2;

each $R^{10}$ is independently: $C_{1-6}$alkyl; halo; $C_{1-6}$alkoxy; or halo-$C_{1-6}$alkyl; and A, Y, Z, m, n, p, q, r, $R^1$, $R^2$, $R^3$, $R^1$, $R^2$, $R^4$, $R^5$, $R^6$, $R^7$ and $R^8$ are as defined herein.

In certain embodiments of formula IIa through IIg, s is 0 or 1.

In certain embodiments of formula IIa through IIg, s is 0.

In certain embodiments of formula IIa through IIg, s is 1.

In certain embodiments of formulas IIa, IIb, IIc, IId, IIe, IIf and IIg, each $R^{10}$ is indepently: $C_{1-6}$alkyl; or halo.

In certain embodiments of formulas IIa, IIb, IIc, IId, IIe, IIf and IIg, each $R^{10}$ is indepently: methyl; or fluoro.

In certain embodiments the subject compounds are of formula IIa.

In certain embodiments the subject compounds are of formula IIb.

In certain embodiments the subject compounds are of formula IIc.

In certain embodiments the subject compounds are of formula IId.

In certain embodiments the subject compounds are of formula IIe.

In certain embodiments the subject compounds are of formula IIf.

In certain embodiments the subject compounds are of formula IIg.

In certain embodiments of formula Ia, the subject compounds may be of formula III:

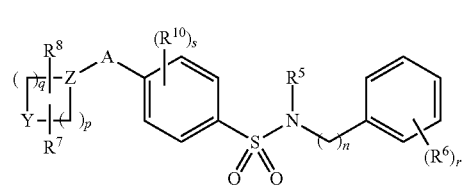
III or pharmaceutically acceptable salts thereof, wherein A, Y, Z, n, p, q, r, s, $R^5$, $R^6$, $R^7$, $R^8$ and $R^{10}$ are as defined herein.

In certain embodiments of formula Ia, the subject compounds may be of formula IV:

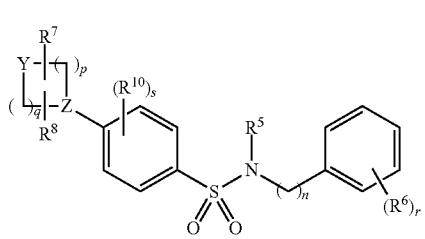

IV or pharmaceutically acceptable salts thereof,
wherein Y, Z, n, p, q, r, s, $R^5$, $R^6$, $R^7$, $R^8$ and $R^{10}$ are as defined herein.

In certain embodiments of formula Ia, the subject compounds may be of formula V:

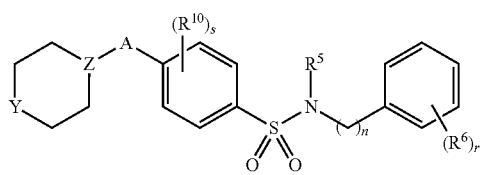

V or pharmaceutically acceptable salts thereof,
wherein A, Y, Z, n, r, s, $R^5$, $R^6$, $R^7$, $R^8$ and $R^{10}$ are as defined herein.

In certain embodiments of formula Ia, the subject compounds may be of formula VI:

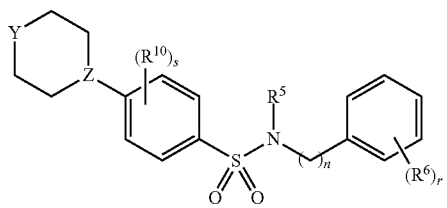

VI or pharmaceutically acceptable salts thereof,
wherein Y, Z, n, r, s, $R^5$, $R^6$, $R^7$, $R^8$ and $R^{10}$ are as defined herein.

In certain embodiments of formula Ia, the subject compounds may be of formula VII:

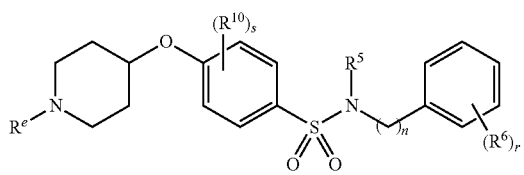

VII or pharmaceutically acceptable salts thereof,
wherein n, r, s, $R^5$, $R^6$, $R^7$, $R^8$, $R^{10}$ and $R^e$ are as defined herein.

In certain embodiments of formula Ia, the subject compounds may be of formula VIII:

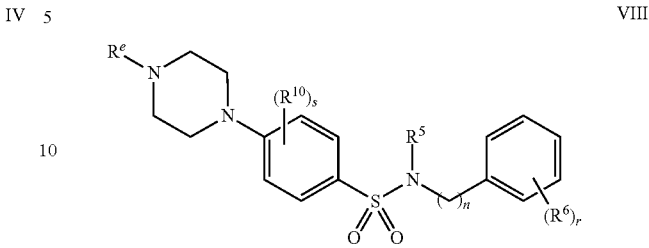

VIII or pharmaceutically acceptable salts thereof,
wherein n, r, s, $R^5$, $R^6$, $R^7$, $R^8$, $R^{10}$ and $R^e$ are as defined herein.

In certain embodiments of formula Ia, the subject compounds may be of formula IX:

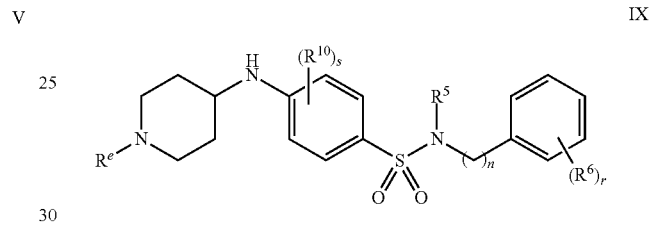

IX or pharmaceutically acceptable salts thereof,
wherein n, r, s, $R^5$, $R^6$, $R^7$, $R^8$, $R^{10}$ and $R^e$ are as defined herein.

The invention also provides a method for treating a disease or condition mediated by or otherwise associated with the RORc receptor, the method comprising administering to a subject in need thereof an effective amount of a compound of the invention.

The disease may be arthritis such as rheumatoid arthritis or osteoarthritis.

The disease may be a asthma or COPD.

Representative compounds in accordance with the methods of the invention are shown in the experimental examples below.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein may be conducted under an inert atmosphere at atmospheric pressure at a reaction temperature range of from about −78° C. to about 150° C., for example, from about 0° C. to about 125° C., or conveniently at about room (or ambient) temperature, e.g., about 20° C.

Scheme A below illustrates one synthetic procedure usable to prepare specific compounds of formula Ia, wherein X is a leaving group and may be the same or different in each occurrence, and m, n, r, $X^1$, $X^2$, $X^3$, $X^4$, Y, Z, $R^1$, $R^2$, $R^3$, $R^4$, $R^5$, $R^6$, $R^7$ and $R^8$ are as defined herein.

compound e. This reaction may be carried out, by way of example, under polar aprotic solvent conditions.

Reaction of compound e with cyclic amine f in step 3a may then provide aryl sulfonamide g, which is a compound of formula I in accordance with the invention. The reaction of step 3a may be carried out in non-polar solvent in the presence of a suitable palladium catalyst.

Alternatively, compound e may be treated with alcohol compound h in step 3b to yield aryl sulfonamide compound i, which is a compound of formula I in accordance with the invention. The reaction of step 3b may be carried out in polar solvent under anhydrous conditions and in the presence of an alkalki metal hydride base.

SCHEME A

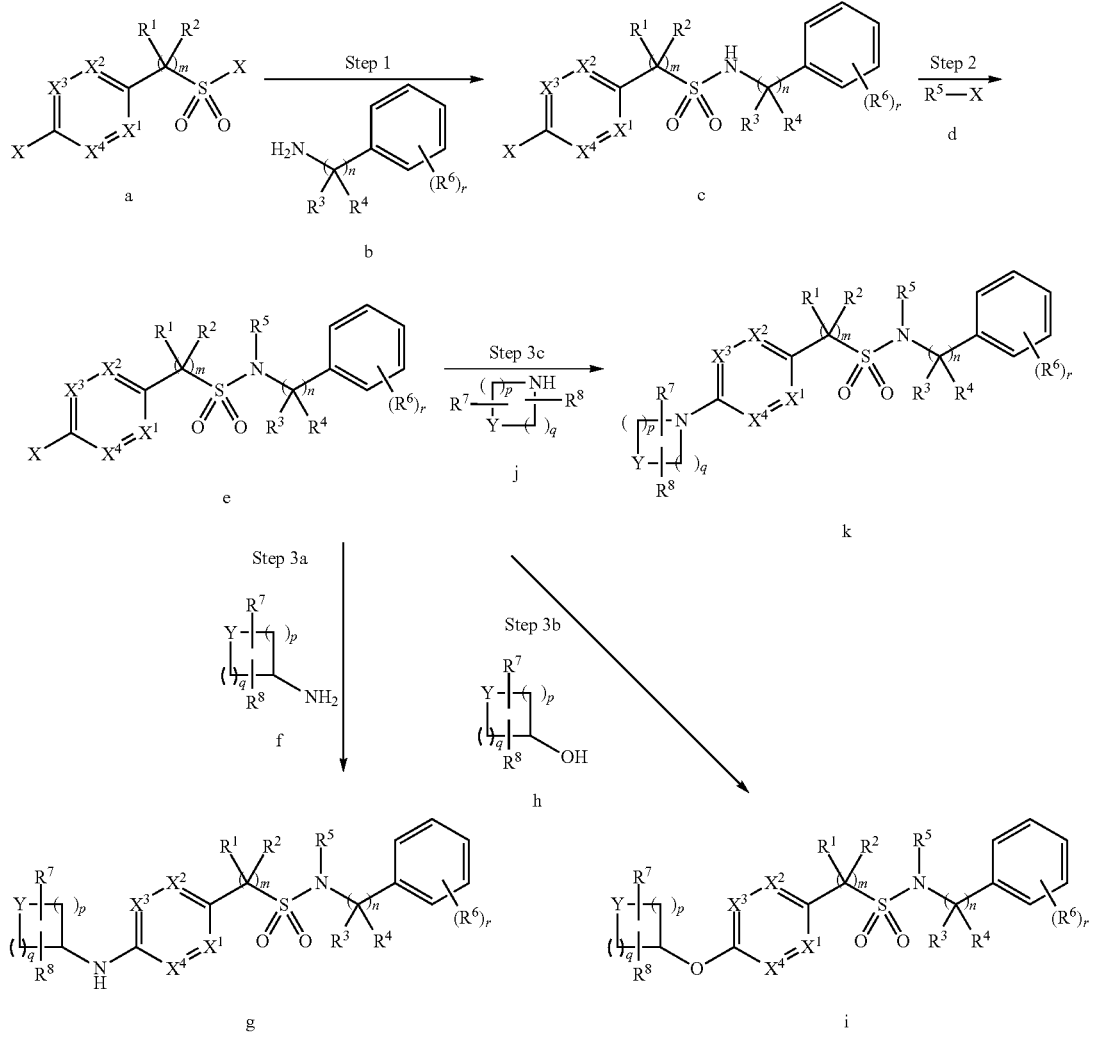

In step 1 of Scheme A, aryl or aralkyl sulfonyl halide compound a is reacted with aryl or aralkyl amine compound b to afford aryl sulfonamide compound c. The reaction of step 1 may be carried out in polar aprotic solvent in the presence of a tertiary amine.

In step 2, an N-alkylation is carried out by treating compound c with alkylating agent d (which may be, for example, an alkyl halide or alkyl triflate), to yield aryl sulfonamide In yet another alternative, compound e may undergo reaction with cyclic amine j to afford aryl sulfonamide compound k, which is a compound of formula I in accordance with the invention. The reaction of step 3c may be carried out in non-polar solvent in the presence of a suitable palladium catalyst.

Many variations on the procedure of Scheme A are possible and will suggest themselves to those skilled in the art. For example, amine compound b may be alkylated with reagent d prior to step 1 in certain embodiments. Various protecting group strategies may be used in the reactions of Scheme A. Specific details for producing compounds of the invention are described in the Examples below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, for example 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. A particular manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets may contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Utility

The compounds of the invention are useful for treatment of immune disorders generally. The compounds may be used for treatment of arthritis, including rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

The compounds may be used for treatment of respiratory disorders such as chronic obstructive pulmonary disease (COPD), asthma, bronchospasm, and the like.

The compounds may be used for treatment of gastrointestinal disorder ("GI disorder") such as Irritable Bowel Syndrome (IBS), Inflammatory Bowel Disease (IBD), biliary colic and other biliary disorders, renal colic, diarrhea-dominant IBS, pain associated with GI distension, and the like.

The compounds may be used for treatment of pain conditions such as inflammatory pain; arthritic pain, surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

General Experimental

LCMS Methods:

High Pressure Liquid Chromatography—Mass Spectrometry (LCMS) experiments to determine retention times (RT) and associated mass ions were performed using one of the following methods:

Method A: Compounds were analysed using the following conditions: Experiments were performed on a Waters ZMD single quadrupole mass spectrometer linked to a Hewlett Packard HP1100 LC system with UV diode array detector and 100 position autosampler. The spectrometer has an electrospray source operating in positive and negative ion mode. This system uses a Phenomenex Luna 3 micron C18(2) 30×4.6 mm column at ambient temperature and a 2.0 mL/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 minutes. This was maintained for 1 minute before returning to 95% solvent A and 5% solvent B over the next 0.5 minute. Total run time was 6 minutes.

Method B: Compounds were analysed using the following conditions: Experiments were performed on a Waters Micromass ZQ2000 quadrupole mass spectrometer linked to a Waters Acquity UPLC system with a PDA UV detector. The spectrometer has an electrospray source operating in positive and negative ion mode. This system uses an Acquity BEH C18 1.7 µm 100×2.1 mm column, maintained at 40° C. or an Acquity BEH Shield RP18 1.7 µm 100×2.1 mm column, maintained at 40° C. and a 0.4 mL/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.6 minutes. This was maintained for 0.8 minute before returning to 95% solvent A and 5% solvent B over the next 1.2 minutes. Total run time was 8 minutes.

NMR Methods:

$^1$H NMR spectra were recorded at ambient temperature or at 80° C. where indicated using one of the following machines: Varian Unity Inova (400 MHz) spectrometer with a triple resonance 5 mm probe, Bruker Avance DRX 400 (400 MHz) spectrometer with a triple resonance 5 mm probe, a Bruker Avance DPX 300 (300 MHz) equipped with a standard 5 mm dual frequency probe for detection of $^1$H and $^{13}$C, a Bruker AVIII (400 MHz) using a BBI Broad Band Inverse 5 mm probe, or a Bruker AVIII (500 MHz) using a QNP (Quad Nucleus detect) 5 mm probe. Chemical shifts are expressed in ppm relative to an internal standard, tetramethylsilane (ppm=0.00). The following abbreviations have been used: br=broad signal, s=singlet, d=doublet, dd=double doublet, t=triplet, q=quartet, m=multiplet, or any combination of.

Microwave Reactor:

Microwave reactions were carried out using a Biotage® Initiator® in vials appropriate to the scale of the reaction and at the temperature and time described in the experimental details.

Purification Equipment:

Purifications were carried out using pre-packed silica gel cartridges either on a Teledyne ISCO CombiFlash® or Biotage® Isolera Four® or using compressed air to apply external pressure. Solvents and gradients shown in the experimental details were used.

Reverse Phase High Pressure Liquid Chromatography (HPLC) was used to purify compounds where indicated. Separation using gradient elution on a Phenomenex Gemini C18 column (250×21.2 mm, 5 micron) as stationary phase and using mobile phase indicated, operating at a 18 mL/min flow rate using a Gilson UV/Vis-155 dual channel detector and Gilson GX-271 automated liquid handler.

Phase separator cartridges are supplied by Biotage® as Isolute® phase separator cartridges.

LIST OF ABBREVIATIONS

AcOH Acetic acid
AIBN 2,2'-Azobis(2-methylpropionitrile)
Atm. Atmosphere
BOC tert-Butyloxycarbonyl group
(BOC)$_2$O Di-tert-butyl dicarbonate
CDCl$_3$ Deuterated chloroform
DavePhos 2-Dicyclohexylphosphino-2'-(N,N-dimethylamino)biphenyl
DCM Dichloromethane/methylene chloride
DMA N,N-Dimethylacetamide
DIAD Diisopropyl azodicarboxylate
DIPEA DIPEA
DMAP 4-Dimethylaminopyridine
DME 1,2-Dimethoxyethane
DMF N,N-Dimethylformamide
DMSO Dimethyl sulfoxide
DPPF 1,1'-Bis(diphenylphosphino)ferrocene
ES Electrospray
Et$_2$O Diethyl ether
Et$_3$N Triethylamine
EtOH Ethanol/Ethyl alcohol
EtOAc Ethyl acetate
HATU 2-(1H-7-Azabenzotriazol-1-yl)-1,1,3,3-tetramethyl uronium hexafluorophosphate methanaminium
HBTU O-Benzotriazol-1-yl-N,N,N',N'-tetramethyluronium hexafluorophosphate
HCl Hydrochloric acid
HOBT 1-Hydroxybenzotriazole
HPLC High pressure liquid chromatography
RP HPLC Reverse phase high pressure liquid chromatography
IBX 2-Iodoxybenzoic acid
IMS Industrial methylated spirit
K$_2$CO$_3$ Potassium carbonate
i-PrOH Isopropanol/isopropyl alcohol/propan-2-ol
LCMS Liquid Chromatograph/Mass Spectroscopy
MeOH Methanol/Methyl alcohol
MW Microwaves
NaH Sodium hydride
NaOH Sodium hydroxide
Na$_2$SO$_4$ Sodium sulfate
Na$_2$CO$_3$ Sodium carbonate
NaHCO$_3$ Sodium bicarbonate/Sodium hydrogen carbonate
NBS N-Bromosuccinimide
NH$_4$Cl Ammonium chloride
NMP 1-Methyl-2-pyrrolidinone
Pd$_2$(dba)$_3$ Tris(dibenzylideneacetone)dipalladium (0)
PSI Pound per square inch
RT Room temperature
sat. Saturated
SCX-2 Pre-packed Isolute® silica-based sorbent with a chemically bonded propylsulfonic acid functional group
TBDMS tert-Butyldimethylsilyl
TFA Trifluoroacetic acid
THF Tetrahydrofuran
TIPS Triisopropylsilyl
TLC Thin layer chromatography
XantPhos 4,5-Bis(diphenylphosphino)-9,9-dimethylxanthene Example 1

1-(4-(4-Acetylpiperazin-1-yl)phenyl)-N-(3-chlorophenyl)-N-isobutylmethanesulfonamide

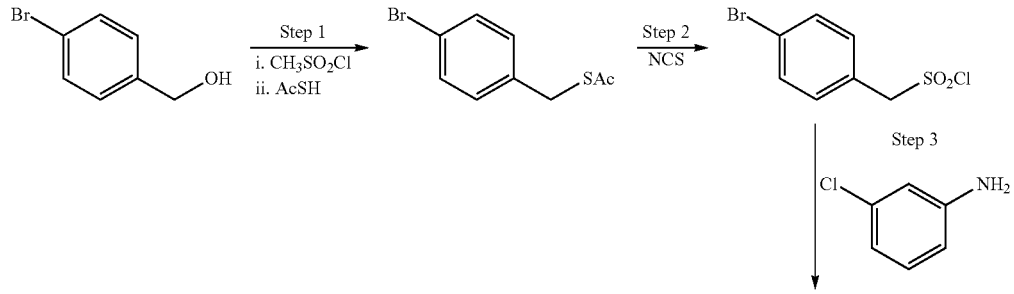

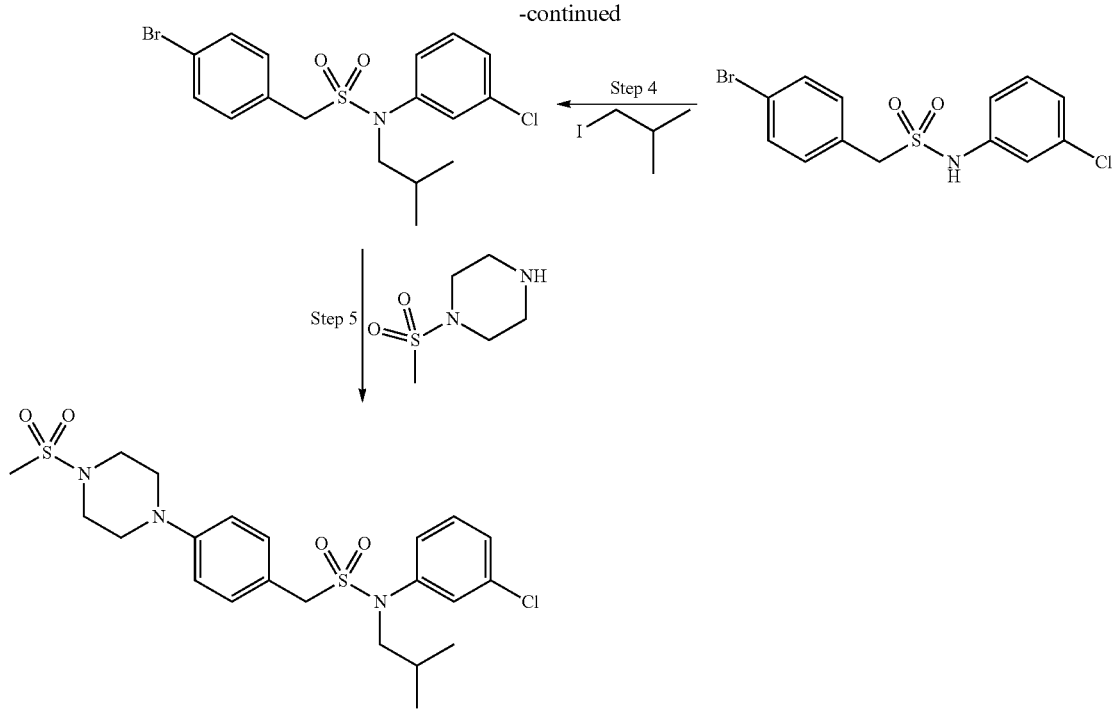

Step 1: Thioacetic acid S-(4-bromo-benzyl)ester

To a solution of 4-bromobenzylalcohol (2 g, 10.7 mmol) in DCM (30 mL) at 0° C. was added Et$_3$N (2.2 mL, 16.0 mmol) followed by methanesulfonyl chloride (910 µL, 11.8 mmol). The reaction was allowed to warm to room temperature, stirred for 2 hours and then quenched with water. Saturated aqueous NaHCO$_3$ was added, the product was extracted with DCM, the combined organic extracts were filtered through a phase separator cartridge and concentrated to give methanesulfonic acid 4-bromo-benzyl ester (2.67 g, 10 mmol, 94%). A solution of the crude product (2.67 g, 10 mmol) in DMSO (40 mL) was stirred at room temperature for 16 hours with potassium thioacetate (1.26 g, 11 mmol). The reaction was treated with water and extracted with DCM, filtered through a phase separator, concentrated and purified by silica gel column chromatography (0-50% DCM in cyclohexane) to give thioacetic acid S-(4-bromo-benzyl)ester (1.81 g, 7.39 mmol, 69%). $^1$H NMR (300 MHz, CDCl$_3$): δ 7.41 (d, 2H), 7.16 (d, 2H), 4.05 (s, 2H), 2.35 (s, 3H).

Step 2: (4-Bromo-phenyl)-methanesulfonyl chloride

To a solution of N-chlorosuccinimide (3.95 g, 29.6 mmol) in acetonitrile (11.6 mL) and 1 M HCl (2.31 mL) at 0° C. was slowly added a solution of thioacetic acid S-(4-bromo-benzyl)ester (1.81 g, 7.39 mmol) in acetonitrile (6.3 mL) over 60 minutes whilst allowing the reaction to warm to 15° C. The remaining solution was added and reaction left to warm to room temperature for 10 minutes. The mixture was cooled to 0° C. and stirred for 1 hour. Water was added and the product was extracted with EtOAc, washed with brine, dried with Na$_2$SO$_4$, concentrated to give (4-bromo-phenyl)-methanesulfonyl chloride (2.6 g, 9.6 mmol). $^1$H NMR (300 MHz, CDCl$_3$): δ 7.60 (d, 2H), 7.36 (d, 2H), 4.81 (s, 2H).

Step 3: C-(4-Bromo-phenyl)-N-(3-chloro-phenyl)-methanesulfonamide

To a solution of (4-bromo-phenyl)-methanesulfonyl chloride (1.4 g, 5.2 mmol) in DCM (20 mL) at room temperature was added pyridine (1.26 mL, 15.6 mmol) followed by 3-chloroaniline (1.1 mL, 10.4 mmol) and the reaction was stirred at room temperature for 3 hours. 1 M aqueous HCl was added and then extracted with DCM, filtered through a separator, concentrated, dry loaded onto silica and purified by silica gel column chromatography (0-100% DCM in cyclohexane) to give C-(4-bromo-phenyl)-N-(3-chloro-phenyl)-methanesulfonamide (0.61 g, 1.68 mmol). $^1$H NMR (300 MHz, CDCl$_3$): δ 7.49 (d, 2H), 7.26 (m, 1H), 7.13-7.15 (m, 4H), 6.96-6.98 (m, 1H), 6.31 (s, 1H), 4.31 (s, 2H).

Step 4: C-(4-Bromo-phenyl)-N-(3-chloro-phenyl)-N-isobutyl-methanesulfonamide To a mixture of C-(4-bromo-phenyl)-N-(3-chloro-phenyl)-methanesulfonamide (0.61 g, 1.68 mmol) and K$_2$CO$_3$ (464 mg, 3.4 mmol) in dimethylformamide (5 mL) was added 1-iodo-2-methylpropane (584 µL, 5.0 mmol). The mixture was heated at 100° C. in microwave reactor for 3 hours. Water was added and the reaction extracted with EtOAc, washed with brine, dried with Na$_2$SO$_4$, concentrated and purified by silica gel column chromatography (0-50% DCM in cyclohexane) to give C-(4-bromo-phenyl)-N-(3-chloro-phenyl)-N-isobutyl-methanesulfonamide (423 mg, 1.0 mmol, 60%). LCMS (m/z, Method A) ES$^+$ 415.8 [M+1]$^+$.

Step 4: 1-(4-(4-acetylpiperazin-1-yl)phenyl)-N-(3-chlorophenyl)-N-isobutylmethanesulfonamide A mixture of C-(4-bromo-phenyl)-N-(3-chloro-phenyl)-N-isobutyl-methanesulfonamide (150 mg, 36 µmol), 1-methanesulfonylpiperazine (59.2 mg, 361 µmol), Pd$_2$(dba)$_3$ (33 mg, 36 μmol), XantPhos (20.9 mg, 36 μmol), and sodium tert-butoxide (104 mg, 1.08 mmol) in toluene (3 mL) was degassed with nitrogen then heated at 120° C. for 30 minutes in a microwave reactor. Water was added and the reaction extracted with EtOAc, washed with brine, dried with $Na_2SO_4$, concentrated and purified by silica gel column chromatography (0-50% EtOAc in cyclohexane) then freeze dried to give the title compound (22.4 mg). $^1$H NMR (400 MHz, DMSO): δ 7.33-7.34 (m, 4H), 7.22 (d, J=8.5 Hz, 2H), 6.95 (d, J=8.5 Hz, 2H), 4.37 (s, 2H), 3.45 (d, J=7.3 Hz, 2H), 3.22-3.27 (m, 8H), 2.92 (s, 3H), 1.44-1.46 (m, 1H), 0.82 (d, J=6.6 Hz, 6H). LCMS (m/z, Method B) $ES^+$ 499.9 $[M+1]^+$.

Example 2

N-(4-Fluoro-benzyl)-N-isobutyl-4-(1-methanesulfonyl-piperidin-4-ylamino)-benzenesulfonamide Step 1: 4-Bromo-N-isobutyl-benzenesulfonamide To a solution of 4-bromobenzenesulfonyl chloride (2 g, 7.8 mmol) in DCM (40 mL) was added pyridine (1.9 mL, 23.5 mmol) followed by isobutylamine (1.56 mL, 15.7 mmol) and the reaction was stirred at room temperature for 16 hours. 1M aqueous HCl was added and the reaction extracted with DCM, filtered through a phase separator and concentrated to give 4-bromo-N-isobutyl-benzenesulfonamide (1.99 g). LCMS (m/z, Method A) $ES^+$ 294$[M+1]^+$ Step 2: 4-Bromo-N-(4-fluoro-benzyl)-N-isobutyl-benzenesulfonamide To a solution of 4-bromo-N-isobutyl-benzenesulfonamide (0.25 g, 856 μmol) in anhydrous dimethylacetamide (5 mL) was added NaH (60% dispersion in mineral oil, 37.7 mg, 942 μmol) and the mixture was stirred at room temperature for 15

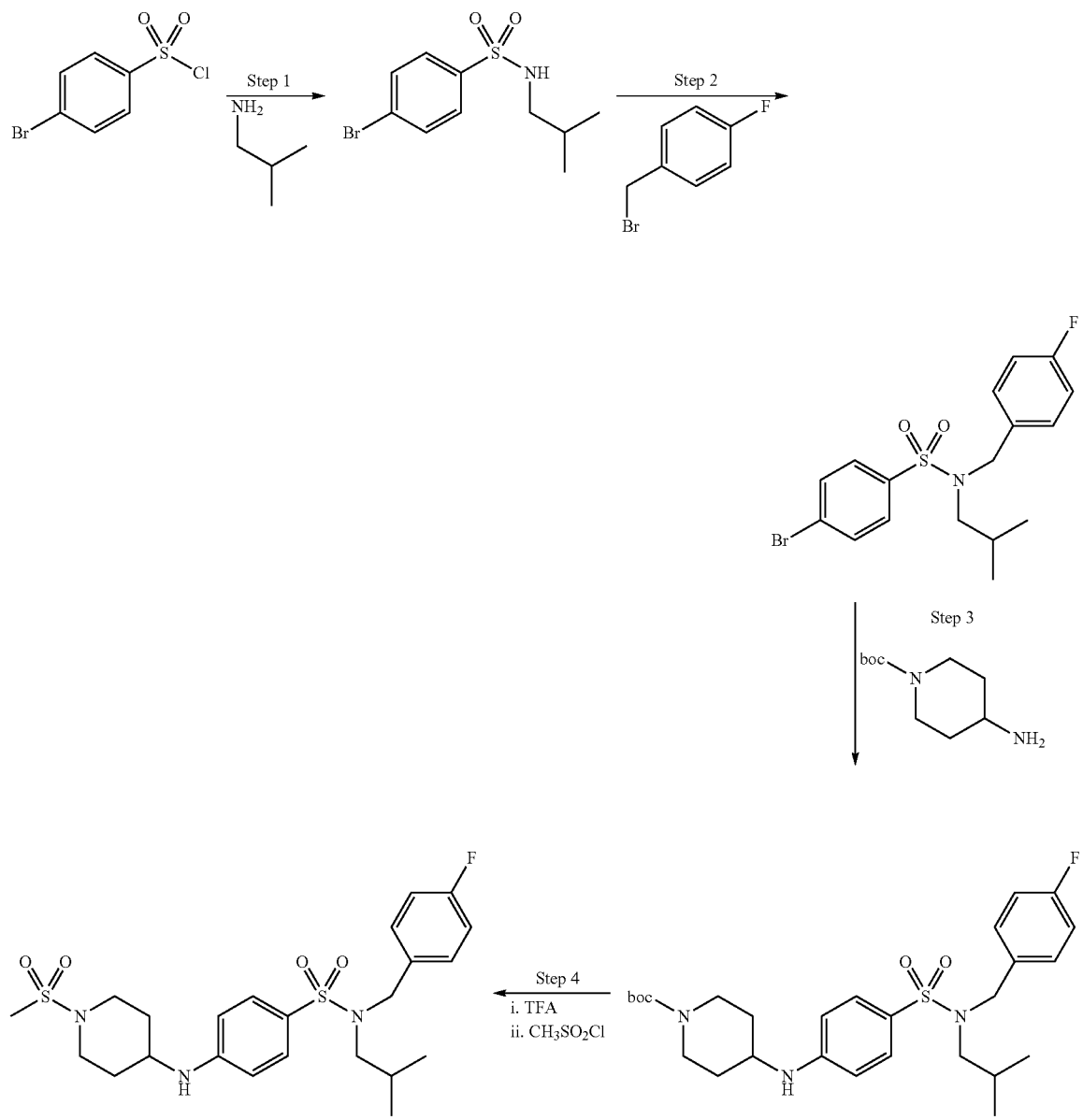

minutes. 4-Fluorobenzyl bromide (117 μL, 942 μmol) was added and reaction heated at 90° C. for 2 hours. The reaction was left to cool to room temperature, water added and then extracted with DCM, filtered through a phase separator, concentrated and purified by silica gel column chromatography (0-25% DCM in cyclohexane) to give 4-bromo-N-(4-fluoro-benzyl)-N-isobutyl-benzenesulfonamide (267 mg, 78%) $^1$H NMR (300 MHz, CDCl$_3$): δ 7.65-7.66 (m, 4H), 7.23 (m, 2H), 6.99 (t, 2H), 4.27 (s, 2H), 2.89 (d, 2H), 1.64 (dt, 1H), 0.74 (d, 6H).

Step 3: 4-{4-[(4-Fluoro-benzyl)-isobutyl-sulfamoyl]-phenylamino}piperidine-1-carboxylic acid tert-butyl ester A mixture of 4-bromo-N-(4-fluoro-benzyl)-N-isobutyl-benzenesulfonamide (200 mg, 500 μmol), 4-amino-1-boc-piperidine (120 mg, 600 μmol), Pd$_2$(dba)$_3$ (46 mg, 50 μmol), XantPhos (29 mg, 50 μmol), and sodium tert-butoxide (106 mg, 1.1 mmol) in toluene (5 mL) was degassed with nitrogen then heated at 125° C. for 30 minutes in a microwave reactor. Water was added then extracted with EtOAc, washed with brine, dried with Na$_2$SO$_4$, concentrated and purified by silica gel column chromatography (0-50% EtOAc in cyclohexane) to give 4-{4-[(4-fluoro-benzyl)-isobutyl-sulfamoyl]-phenylamino}-piperidine-1-carboxylic acid tert-butyl ester (208 mg, 80%). LCMS (m/z, Method A) ES$^-$ 518[M−1]$^-$.

Step 4: N-(4-Fluoro-benzyl)-N-isobutyl-4-(1-methanesulfonyl-piperidin-4-ylamino)-benzenesulfonamide)

To a solution of 4-{4-[(4-fluoro-benzyl)-isobutyl-sulfamoyl]-phenylamino}-piperidine-1-carboxylic acid tert-butyl ester (208 mg) in DCM (9 mL) was added TFA (1 mL) and the reaction was stirred at room temperature for 30 minutes. The reaction was concentrated and purified by SCX column eluting with 2 M NH$_3$ in MeOH to give N-(4-fluoro-benzyl)-N-isobutyl-4-(piperidin-4-ylamino)-benzenesulfonamide. A solution of the crude product (149 mg) in DCM (5 mL) was added DIPEA (124 μL, 711 μmol) followed by methane sulfonylchloride (28 μL, 356 μmol) and the reaction stirred at room temperature for 30 minutes. Water was then added, passed through a phase separator, extracted once more through a phase separator, concentrated and purified by silica gel column chromatography (0-75% EtOAc in cyclohexane) to give the title compound (139 mg). $^1$H NMR (400 MHz, DMSO): δ 7.51 (d, J=8.7 Hz, 2H), 7.4 (dd, J=8.5, 5.6 Hz, 2H), 7.15 (t, J=8.8 Hz, 2H), 6.71 (d, J=8.7 Hz, 2H), 6.55 (d, J=7.8 Hz, 1H), 4.15 (s, 2H), 3.48-3.53 (m, 3H), 2.93 (d, J=11.6 Hz, 2H), 2.89 (s, 3H), 2.76 (d, J=7.4 Hz, 2H), 1.99 (m, 2H), 1.44-1.49 (m, 3H), 0.65 (d, J=6.6 Hz, 6H). LCMS (m/z, Method B) ES$^+$ 498.0 [M+1]+.

Example 3

N-(4-Fluoro-phenyl)-N-isobutyl-4-(1-methanesulfonyl-piperidin-4-yloxy)-benzenesulfonamide

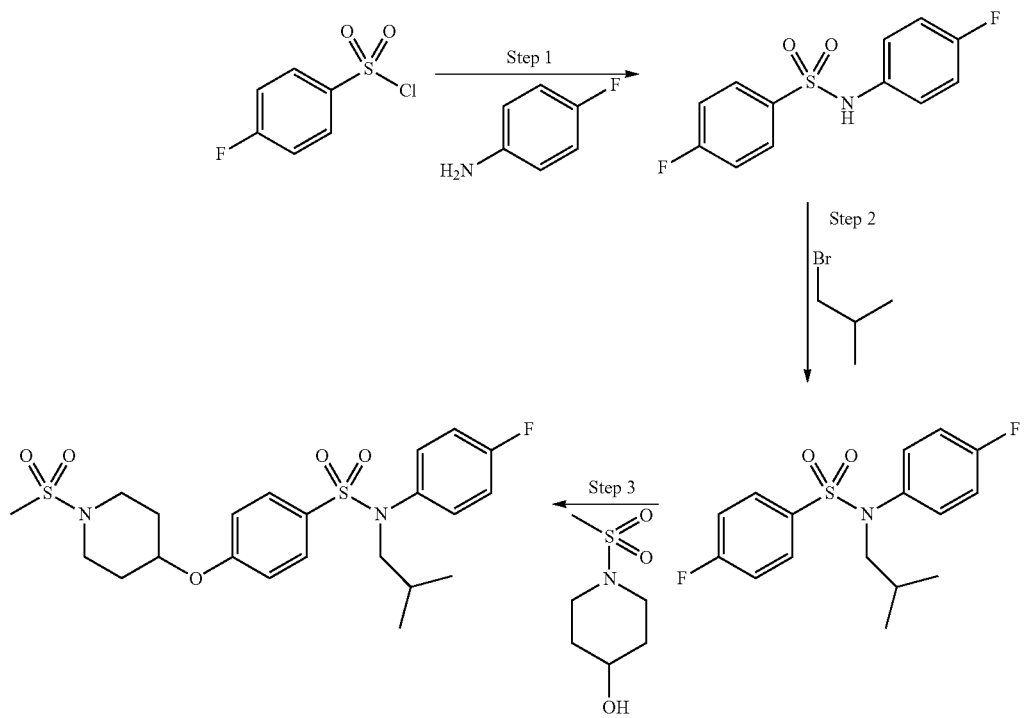

Step 1:
4-Fluoro-N-(4-fluoro-phenyl)-benzenesulfonamide

To a solution of 4-fluorobenzenesulfonyl chloride (2 g, 10.3 mmol) at room temperature was stirred with pyridine (2.49 mL, 30.8 mmol) and 4-fluoroaniline (1.95 mL, 20.6 mmol) for 2 hrs. The reaction was quenched with 1 M HCl aqueous and then extracted with DCM, filtered through a phase separator and purified by silica gel column chromatography (0-100% DCM in cyclohexane) to give 4-fluoro-N-(4-fluoro-phenyl)-benzenesulfonamide (2.15 g, 78%). LCMS (m/z, Method A) ES$^+$ 270 [M+1]$^+$.

Step 2: 4-Fluoro-N-(4-fluoro-phenyl)-N-isobutyl-benzenesulfonamide

To a mixture of 4-fluoro-N-(4-fluoro-phenyl)-benzenesulfonamide (1.0 g, 3.7 mmol) and K$_2$CO$_3$ (1.03 g, 7.4 mmol) in dimethylformamide (5 mL) was added 1-bromo-2-methylpropane (1.21 mL, 11.2 mmol). The mixture was heated at 100° C. in a microwave reactor for 3 hours. Water was added and then extracted with EtOAc, washed with brine, dried with Na$_2$SO$_4$ then concentrated. The crude product was re-dissolved in cyclohexane then concentrated to give 4-fluoro-N-(4-fluoro-phenyl)-N-isobutyl-benzenesulfonamide (1.05 g, 86%). $^1$H NMR (300 MHz, CDCl$_3$): δ 7.56-7.57 (m, 2H), 7.12-7.13 (m, 2H), 7.00 (d, 4H), 3.28 (d, 2H), 1.54 (m, 1H), 0.91 (d, 6H).

Step 3: (N-(4-Fluoro-phenyl)-N-isobutyl-4-(1-methanesulfonyl-piperidin-4-yloxy)-benzenesulfonamide)

To a solution of 1-methanesulfonyl-piperidin-4-ol (61 mg) in anhydrous tetrohydrofuran (5 mL) at room temperature was added NaH (60% dispersion in mineral oil, 15 mg, 369 µmol) and the reaction was stirred at room temperature for 30 minutes. 4-Fluoro-N-(4-fluoro-phenyl)-N-isobutyl-benzenesulfonamide (100 mg, 308 µmol) was added and the reaction was heated at 90° C. for 3 hours. The reaction was allowed to cool to room temperature, water was added and then extracted with EtOAc, concentrated, purified by preparative reverse-phase HPLC and then freeze dried to give the title compound (51.8 mg). $^1$H NMR (400 MHz, DMSO): δ 7.44 (d, J=8.8 Hz, 2H), 7.13-7.14 (m, 7H), 4.69 (t, J=3.8 Hz, 1H), 3.35 (d, J=10.8 Hz, 4H), 3.28 (d, J=7.4 Hz, 3H), 3.12-3.14 (m, 2H), 2.91 (s, 3H), 2.03 (br s, 3H), 1.71-1.79 (m, 3H), 1.41 (t, J=6.8 Hz, 1H), 0.84 (d, J=6.6 Hz, 6H). LCMS (m/z, Method B) ES$^+$ 484.9 [M+1]$^+$.

Example 4

N-Cyclobutyl-N-(3-fluoro-phenyl)-4-(1-methanesulfonyl-piperidin-4-yloxy)-benzenesulfonamide

Step 1: Cyclobutyl-(3-fluoro-phenyl)-amine

A mixture of 3-fluoroiodobenzene (1.0 g, 4.5 mmol), cyclobutylamine (320 µL, 3.8 mmol), Pd$_2$(dba)$_3$ (34 mg, 38 µmol), XantPhos (54 mg, 94 µmol), and sodium tert-butoxide (541 mg, 5.6 mmol) in toluene (10 mL) was degassed with nitrogen then heated at 120° C. for 30 minutes in a microwave reactor. Saturated aqueous NaHCO$_3$ was added and then extracted with EtOAc, washed with brine, dried with Na$_2$SO$_4$, concentrated and purified by silica gel column chromatography (0-50% DCM in cyclohexane) to give cyclobutyl-(3-fluoro-phenyl)-amine (447 mg, 71%). LCMS (m/z, Method A) ES$^+$ 166[M+1]$^+$.

Step 2: N-Cyclobutyl-4-fluoro-N-(3-fluoro-phenyl)-benzenesulfonamide

To a solution of cyclobutyl-(3-fluoro-phenyl)-amine (447 mg, 2.7 mmol) in DCM (8 mL) was added pyridine (438 µL, 5.4 mmol) followed by 4-fluorobenzenesulfonyl chloride (633 mg, 3.3 mmol) in DCM (3 mL) and then the reaction was stirred at room temperature for 2 hrs. The reaction was left to stand at room temperature for 64 hours. 1 M aqueous HCl was added then extracted with DCM, filtered through a phase separator and then purified by silica gel column chromatography (0-50% DCM in cyclohexane) to give N-cyclobutyl-4-fluoro-N-(3-fluoro-phenyl)-benzenesulfonamide (756 mg, 2.3 mmol, 85%). LCMS (m/z, Method A) ES$^+$ 324 [M+1]$^+$.

Step 3: 4-{4-[Cyclobutyl-(3-fluoro-phenyl)-sulfamoyl]-phenoxy}-piperidine-1-carboxylic acid tert-butyl ester To a solution of tert-butyl-4-hydroxy-1-piperidinecarboxylate (137 mg, 681 mmol) in anhydrous THF (5 mL) was added NaH (60% dispersion in mineral oil, 30 mg, 743 mmol) and the reaction was stirred at room temperature for 15 minutes. N-Cyclobutyl-4-fluoro-N-(3-fluoro-phenyl)-benzenesulfonamide (200 mg, 619 µmol) was added and the reaction was heated at 90° C. for 4 hours. The reaction was left to cool to room temperature, water added and extracted with EtOAc,

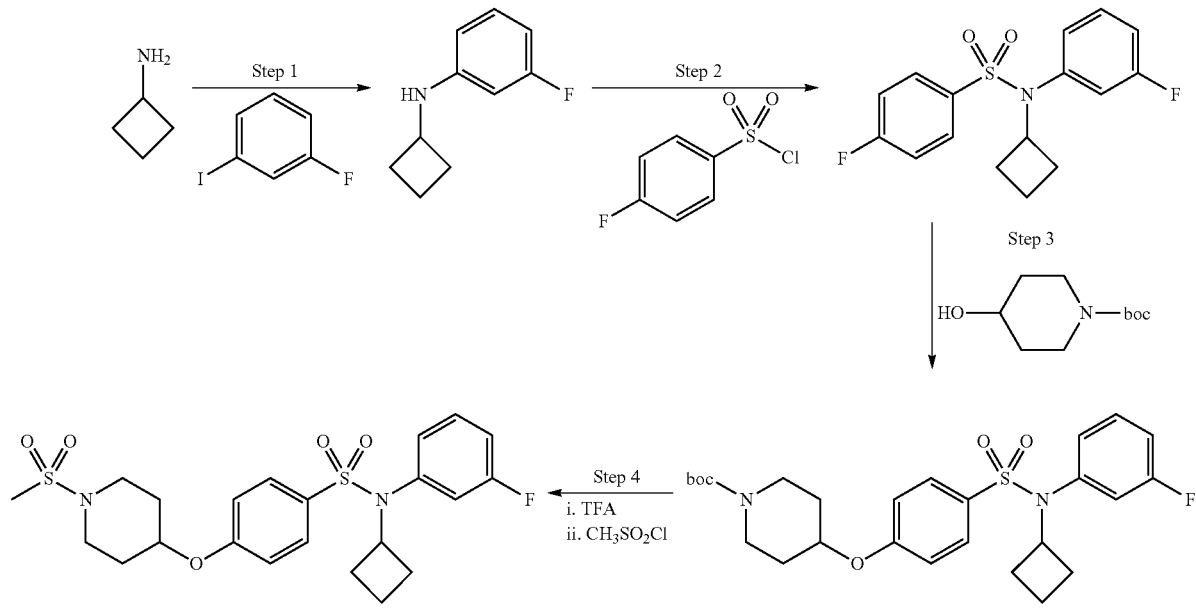

washed with brine, dried with Na₂SO₄ then concentrated and purified by silica gel column chromatography (0-50% EtOAc in cyclohexane) to give 4-{4-[cyclobutyl-(3-fluoro-phenyl)-sulfamoyl]-phenoxy}-piperidine-1-carboxylic acid tert-butyl ester (330 mg). LCMS (m/z, Method A) ES⁺ 527 [M+23]⁺.

Step 4: (N-Cyclobutyl-N-(3-fluoro-phenyl)-4-(1-methanesulfonyl-piperidin-4-yloxy)-benzenesulfonamide)

To a solution of 4-{4-[cyclobutyl-(3-fluoro-phenyl)-sulfamoyl]-phenoxy}-piperidine-1-carboxylic acid tert-butyl ester (330 mg, 655 µmol) in DCM (9 mL) was added TFA (1 mL) and then the reaction was stirred at room temperature for 30 minutes. The reaction was concentrated and then purified by SCX eluting with 2 M NH₃ in MeOH to give N-cyclobutyl-N-(3-fluoro-phenyl)-4-(piperidin-4-yloxy)-benzenesulfonamide (195 mg, 483 µmol). To a solution of N-cyclobutyl-N-(3-fluoro-phenyl)-4-(piperidin-4-yloxy)-benzenesulfonamide in DCM (10 mL) was added DIPEA (168 µL, 965 µmol) and methanesulfonyl chloride (41 µL, 531 µmol) and the reaction was stirred at room temperature for 30 minutes. Water was added and then extracted with DCM, filtered through a phase separator and concentrated. Purification by silica gel column chromatography (0-50% EtOAc in cyclohexane) followed by preparative reverse a phase HPLC gave the title compound (169 mg). ¹H NMR δ (DMSO): 7.46 (2H, d, J=8.8 Hz), 7.38-7.39 (1H, m), 7.16-7.17 (3H, m), 6.77-6.78 (2H, m), 4.69-4.71 (1H, m), 4.20-4.22 (1H, m), 3.33-3.38 (4H, m), 3.13 (2H, ddd, J=12.1, 8.09, 3.4 Hz), 2.91 (3H, s), 2.03-2.06 (4H, m), 1.77-1.81 (4H, m), 1.53-1.56 (2H, m). LCMS (m/z, Method B) ES⁺ 482.9 [M+1]⁺.

Example 5

N-(4-fluorophenyl)-N-isobutyl-6-((1-(methylsulfonyl)piperidin-4-yl)oxy)pyridine-3-sulfonamide

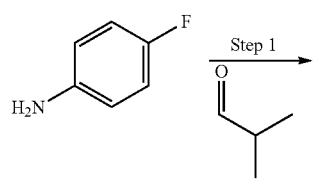

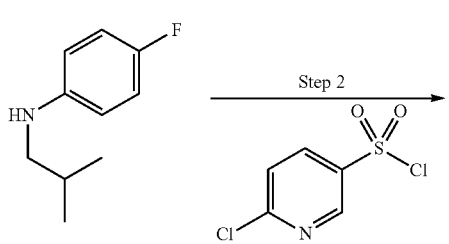

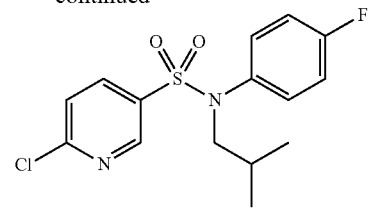

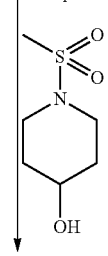

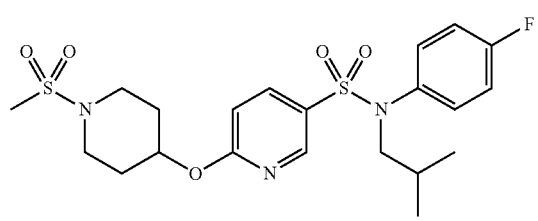

Step 1: (4-Fluoro-phenyl)-isobutyl-amine

To a solution of 4-fluoroaniline (1 g, 9 mmol) in DCM (20 mL) at room temperature was added isobutyraldehyde (985 µL, 10.8 mmol) followed by portionwise sodium triacetoxyborohydride (2.86 g, 13.5 mmol) and the reaction was stirred at room temperature for 64 hours. The reaction was concentrated and then dissolved in DCM and MeOH, dry loaded onto silica then purified by silica gel column chromatography (0-25% DCM in cyclohexane) to give (4-fluoro-phenyl)-isobutyl-amine (817 mg, 54%). LCMS (m/z, Method A) ES+ 168 [M+1]+.

Step 2: 6-Chloro-pyridine-3-sulfonic acid (4-fluoro-phenyl)-isobutyl-amide

To a solution of (4-fluoro-phenyl)-isobutyl-amine (250 mg, 1.5 mmol) in DCM (5 mL) was added pyridine (242 µL, 3.0 mmol) followed by 6-chloropyridine-3-sulfonylchloride (379 mg, 1.8 mmol) and the reaction was stirred at room temperature for 2 hours. Water and saturated NaHCO₃ were added and then extracted with DCM, filtered through a phase separator, concentrated then purified by silica gel column chromatography (0-20% EtOAC in cyclohexane) to give chloro-pyridine-3-sulfonic acid (4-fluoro-phenyl)-isobutyl-amide (411 mg, 80%) LCMS (m/z, Method A) ES⁺ 343 [M+1]⁺.

Step 3: (6-(1-Methanesulfonyl-piperidin-4-yloxy)-pyridine-3-sulfonic acid (4-fluoro-phenyl)-isobutyl-amide)

To a solution of 1-methanesulfonyl-piperidin-4-ol (86 mg, 482 μmol) in anhydrous THF (5 mL) at room temperature was added NaH (60% dispersion in mineral oil, 21 mg, 526 μmol) and the reaction was stirred at room temperature for 15 minutes. Chloro-pyridine-3-sulfonic acid (4-fluoro-phenyl)-isobutyl-amide (150 mg, 439 μmol) was added and the reaction stirred at room temperature for 45 minutes then heated at 80° C. for 2 hours. Water and saturated NaHCO$_3$ were added and then extracted with EtOAc, washed with brine, dried with Na$_2$SO$_4$ then concentrated and purified by silica gel column chromatography (0-25% EtOAc in cyclohexane) to give the title compound (137 mg). $^1$H NMR (400 MHz, DMSO): δ 8.30 (dd, J=2.6, 0.67 Hz, 1H), 7.75 (dd, J=8.8, 2.60 Hz, 1H), 7.19-7.20 (m, 4H), 6.97 (dd, J=8.8, 0.7 Hz, 1H), 5.23-5.25 (m, 1H), 3.39 (d, J=8.8 Hz, 4H), 3.13 (ddd, J=12.2, 8.56, 3.46 Hz, 2H), 2.91 (s, 3H), 2.04-2.09 (m, 2H), 1.78-1.80 (m, 2H), 1.44 (dd, J=13.6, 6.9 Hz, 1H), 0.85 (d, J=6.6 Hz, 6H). LCMS (m/z, Method B) ES$^+$ 485.9 [M+1]$^+$.

Example 6

N-(4-fluorophenyl)-N-isobutyl-5-((1-(methylsulfonyl)piperidin-4-yl)amino)pyridine-2-sulfonamide

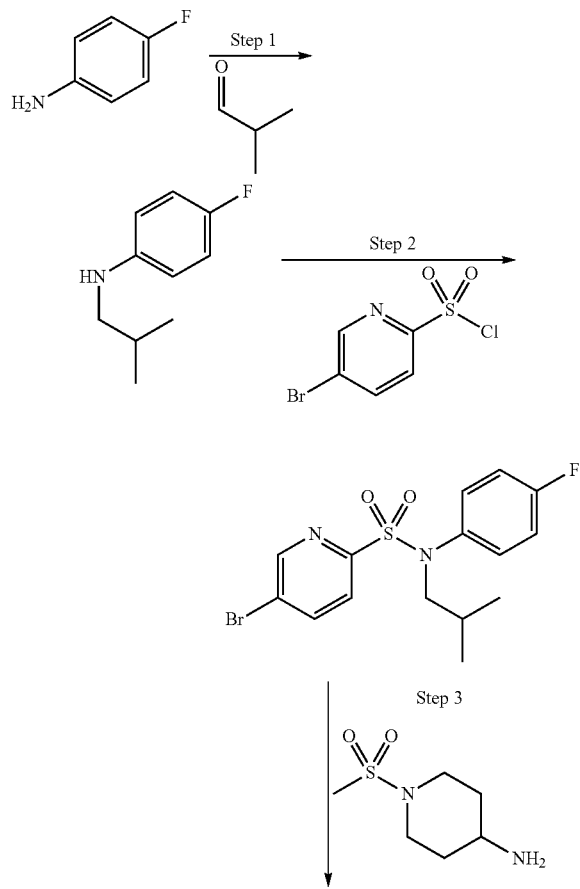

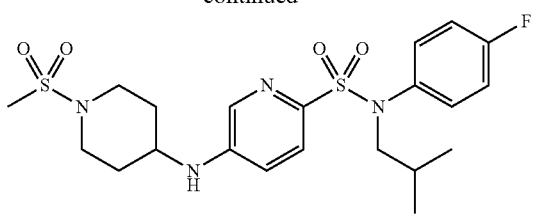

Step 1: (4-Fluoro-phenyl)-isobutyl-amine

To a solution of 4-fluoroaniline (1 g, 9 mmol) in DCM (20 mL) at room temperature was added isobutyraldehyde (985 μL, 10.8 mmol) followed by portionwise sodium triacetoxyborohydride (2.86 g, 13.5 mmol) and the reaction was stirred at room temperature for 64 hours. The reaction was concentrated and then dissolved in DCM and MeOH, dry loaded onto silica then purified by silica gel column chromatography (0-25% DCM in cyclohexane) to give (4-fluoro-phenyl)-isobutyl-amine (817 mg, 54%). LCMS (m/z, Method A) ES$^+$ 168 [M+1]$^+$.

Step 2: 5-Bromo-pyridine-2-sulfonic acid (4-fluoro-phenyl)-isobutyl-amide

To a solution of 5-bromo-pyridine-2-sulfonyl chloride (330 mg, 1.29 mmol) in DCM (10 mL) was added pyridine (208 μL, 2.57 mmol) followed by a solution of (4-fluoro-phenyl)-isobutyl-amine (215 mg, 1.29 mmol) in DCM (10 mL) and the reaction was stirred at room temperature for 16 hours. Water and saturated aqueous NaHCO$_3$ were added and then extracted with DCM, filtered through a phase separator, concentrated then purified by silica gel column chromatography (0-20% EtOAc in cyclohexane) to give 5-bromo-pyridine-2-sulfonic acid (4-fluoro-phenyl)-isobutyl-amide (414 mg, 78%). LCMS (m/z, Method A) ES$^+$ 387/389 [M+1]$^+$.

Step 3: 5-(1-Methanesulfonyl-piperidin-4-ylamino)-pyridine-2-sulfonic acid (4-fluoro-phenyl)-isobutyl-amide A mixture of 5-bromo-pyridine-2-sulfonic acid (4-fluoro-phenyl)-isobutyl-amide (150 mg, 388 μmol), 4-amino-1-methanesulfonylpiperidine (82.8 mg, 465 μmol), Pd$_2$(dba)$_3$ (36 mg, 39 μmol), XantPhos (22 mg, 39 μmol), and sodium tert-butoxide (82 mg, 853 μmol) in toluene (4 mL) was degassed with nitrogen then heated at 125° C. for 30 minutes in a microwave reactor. Saturated aqueous NaHCO$_3$ was added and then extracted with EtOAc, washed with brine, concentrated and purified by silica gel column chromatography (0-75% EtOAc in cyclohexane) to give the title compound (103 mg). $^1$H NMR (400 MHz, DMSO-d6): δ 8.10 (d, 1H), 7.36 (d, 1H), 7.15 (d, 4H), 6.96 (dd, 1H), 6.81 (d, 1H), 3.50-3.52 (m, 5H), 2.89 (s, 5H), 1.99 (s, 2H), 1.43-1.47 (m, 3H), 0.83 (d, 6H). LCMS (m/z, Method A) ES$^+$ 484.9 [M+1]$^+$.

Example 7

N-(4-fluorophenyl)-N-isobutyl-6-((1-(methylsulfonyl)piperidin-4-yl)amino)pyridine-3-sulfonamide

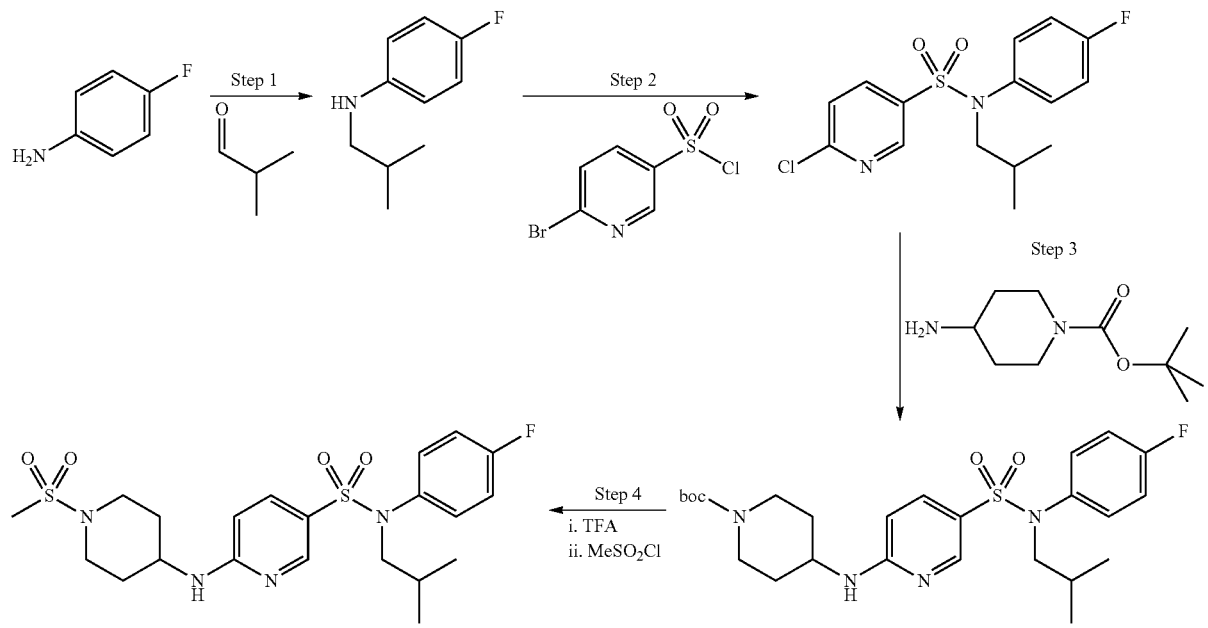

Step 1: (4-Fluoro-phenyl)-isobutyl-amine

To a solution of 4-fluoroaniline (1 g, 9 mmol) in DCM (20 mL) at room temperature was added isobutyraldehyde (985 µL, 10.8 mmol) followed by portionwise sodium triacetoxyborohydride (2.86 g, 13.5 mmol) and the reaction was stirred at room temperature for 64 hours. The reaction was concentrated and then dissolved in DCM and MeOH, dry loaded onto silica then purified by silica gel column chromatography (0-25% DCM in cyclohexane) to give (4-fluoro-phenyl)-isobutyl-amine (817 mg, 54%). LCMS (m/z, Method A) $ES^+$ 168 $[M+1]^+$.

Step 2: 6-Chloro-pyridine-3-sulfonic acid (4-fluoro-phenyl)-isobutyl-amide

To a solution of (4-fluoro-phenyl)-isobutyl-amine (250 mg, 1.5 mmol) in DCM (5 mL) was added pyridine (242 µL, 3.0 mmol) followed by 6-chloropyridine-3-sulfonyl chloride (379 mg, 1.8 mmol) and the reaction was stirred at room temperature for 2 hours. Water and saturated aqueous $NaHCO_3$ were added and then extracted with DCM, filtered through a phase separator, concentrated then purified by silica gel column chromatography (0-20% EtOAc in cyclohexane) to give 6-chloro-pyridine-3-sulfonic acid (4-fluoro-phenyl)-isobutyl-amide (411 mg, 67%). LCMS (m/z, Method A) $ES^+$ 343 $[M+1]^+$.

Step 3: 4-{5-[(4-Fluoro-phenyl)-isobutyl-sulfamoyl]-pyridin-2-ylamino}-piperidine-1-carboxylic acid tert-butyl ester To a solution of 6-chloro-pyridine-3-sulfonic acid (4-fluoro-phenyl)-isobutyl-amide (150 mg, 439 µmol) and 4-amino-1-boc piperidine (114 mg, 570 µmol) in acetonitrile (3 mL) was added DIPEA (115 µl, 658 µmol) and the reaction was heated at 160° C. in a microwave reactor for 2.5 hours. EtOAc and saturated aqueous $NaHCO_3$ were added, extracted, washed with brine, dried with $Na_2SO_4$ then concentrated and purified by silica gel column chromatography (0-50% EtOAc in cyclohexane) to give 4-{5-[(4-fluoro-phenyl)-isobutyl-sulfamoyl]-pyridin-2-ylamino}-piperidine-1-carboxylic acid tert-butyl ester (69 mg, 31%). LCMS (m/z, Method A) $ES^-$ 506 $[M-1]^-$.

Step 4: (6-(1-Methanesulfonyl-piperidin-4-ylamino)-pyridine-3-sulfonic acid (4-fluoro-phenyl)-isobutyl-amide)

To a solution of 4-{5-[(4-fluoro-phenyl)-isobutyl-sulfamoyl]-pyridin-2-ylamino}-piperidine-1-carboxylic acid tert-butyl ester (66 mg, 130 µmol) in DCM (8 mL) was added TFA (2 mL) and the reaction was stirred at room temperature for 30 minutes. The reaction was concentrated and purified by SCX column eluting with 2M $NH_3$ in MeOH to give 6-(piperidin-4-ylamino)-pyridine-3-sulfonic acid (4-fluoro-phenyl)-isobutyl-amide (41 mg, 101 µmol). To a solution of 6-(piperidin-4-ylamino)-pyridine-3-sulfonic acid (4-fluoro-phenyl)-isobutyl-amide (41 mg, 101 µmol) in DCM (5 mL) was added DIPEA (35 µL, 202 µmol) followed by methane sulfonylchloride (1 mL of a 78 µL, 1 mmol solution in 10 mL of DCM) and the reaction stirred at room temperature for 30 minutes. Water and saturated $NaHCO_3$ were then added, extracted, filtered through a phase separator, concentrated and purified by silica gel column chromatography (0-50% EtOAc in cyclohexane) to give the title compound (49 mg). $^1$H NMR (400 MHz, DMSO): δ 8.03 (d, J=2.52 Hz, 1H), 7.54 (d, J=7.47 Hz, 1H), 7.35 (dd, J=8.95, 2.54 Hz, 1H), 7.17 (t, J=8.01 Hz, 4H), 6.51 (d, J=8.98 Hz, 1H), 3.91 (br s, 1H), 3.51 (d, J=11.88 Hz, 2H), 3.25 (d, J=7.31 Hz, 2H), 2.86 (m, 5H), 1.97 (d, J=12.65 Hz, 2H), 1.44-1.49 (m, 2H), 0.82 (d, J=6.63 Hz, 6H). LCMS (m/z, Method B) $ES^+$ 485.0 $[M+1]^+$.

Example 8
N-(4-chlorobenzyl)-4-(((+/−)trans-3-hydroxy-1-(methylsulfonyl)piperidin-4-yl)oxy)-N-isobutylbenzenesulfonamide
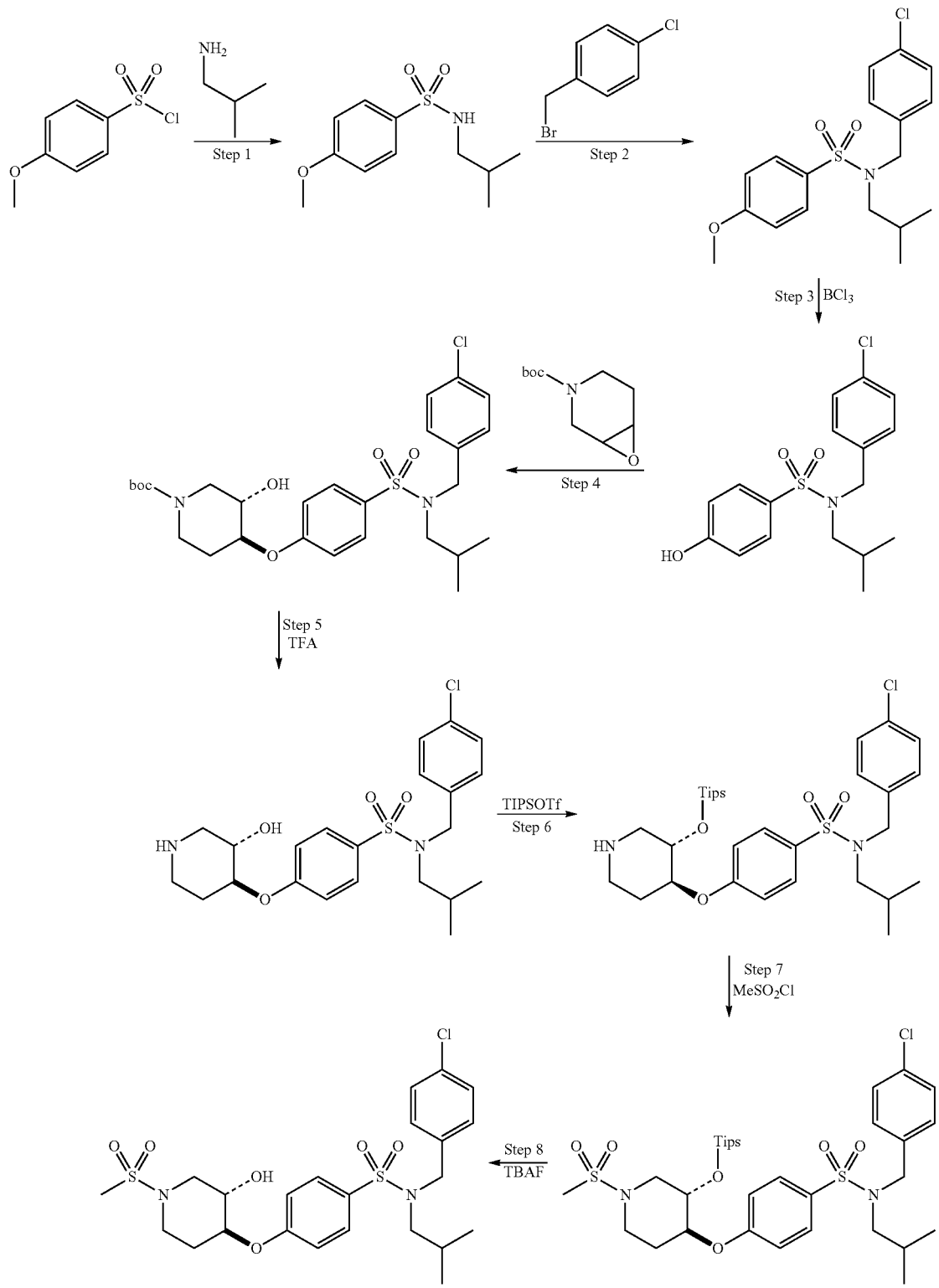

Step 1: N-Isobutyl-4-methoxy-benzenesulfonamide

To a solution of 4-methoxybenzenesulfonylchloride (1 g, 4.8 mmol) in DCM (20 mL) was added pyridine (1.17 mL, 14.5 mmol) followed by isobutylamine (961 µL, 9.7 mmol) and the reaction was stirred at room temperature for 16 hours. 1 M aqueous HCl was added, extracted with DCM, filtered through a phase separator, concentrated then purified by silica gel column chromatography (100% DCM) to give N-isobutyl-4-methoxy-benzenesulfonamide (1.03 g, 88%). LCMS (m/z, Method A) ES$^-$ 242 [M−1]$^-$.

Step 2: N-(4-Chloro-benzyl)-N-isobutyl-4-methoxy-benzenesulfonamide

To a solution of N-isobutyl-4-methoxy-benzenesulfonamide (1.03 g, 4.2 mmol) in anhydrous dimethylacetamide (20 mL) at 0° C. was added NaH (60% dispersion in mineral oil, 186 mg, 4.6 mmol) until no more gas evolved then stirred for a further 10 minutes. 4-Chlorobenzylbromide (951 mg, 4.6 mmol) was added and the reaction heated at 90° C. for 2 hours. The reaction was left to cool to room temperature, water was added, extracted with DCM, filtered through a phase separator, concentrated then purified by silica gel column chromatography (0-50% DCM in cyclohexane) to give N-(4-chloro-benzyl)-N-isobutyl-4-methoxy-benzenesulfonamide (1.03 g, 67%). LCMS (m/z, Method A)) ES$^+$ 368 [M+1]$^+$.

Step 3: N-(4-Chloro-benzyl)-4-hydroxy-N-isobutyl-benzenesulfonamide

To a solution of N-(4-chloro-benzyl)-N-isobutyl-4-methoxy-benzenesulfonamide (1.03 g, 2.8 mmol) in DCM (25 mL) was added tetrabutylammonium iodide (1.14 g, 3.1 mmol) and the reaction was cool to −78° C. To the solution was added boron trichloride (4.2 mL, 4.2 mmol of 1 M solution in DCM) over 2 minutes then stirred for a further 5 minutes. The reaction was left to warm to 0° C. and stirred for further 2 hours. Water and saturated aqueous NaHCO$_3$ were added, extracted with DCM, filtered through a phase separator, concentrated then purified by silica gel column chromatography (0-30% EtOAc in cyclohexane) to give N-(4-chloro-benzyl)-4-hydroxy-N-isobutyl-benzenesulfonamide (629 mg, 64%). LCMS (m/z, Method A) ES$^-$ 352 [M−1]$^-$.

Step 4: (+/−)trans-4-{4-[(4-Chloro-benzyl)-isobutyl-sulfamoyl]-phenoxy}-3-hydroxy-piperidine-1-carboxylic acid tert-butyl ester To a solution of 7-oxa-3-aza-bicyclo[4.1.0]heptane-3-carboxylic acid tert-butyl ester (354 mg, 1.8 mmol) in EtOH (5 mL) was added K$_2$CO$_3$ (246 mg, 1.8 mmol) and a solution of N-(4-chloro-benzyl)-4-hydroxy-N-isobutyl-benzenesulfonamide (629 mg, 1.78 mmol) in EtOH (5 mL) and the reaction was heated at 95° C. for 16 hours. The reaction was left to cool to room temperature and concentrated. Water and EtOAc were added, extracted, washed with brine, dried with Na$_2$SO$_4$ then concentrated and purified by silica gel column chromatography (0-100% EtOAc in cyclohexane) to give (+/−)trans-4-{4-[(4-chloro-benzyl)-isobutyl-sulfamoyl]-phenoxy}-3-hydroxy-piperidine-1-carboxylic acid tert-butyl ester (259 mg, 26%). LCMS (m/z, Method A) ES$^+$ 553 [M+1]$^+$.

Step 5: N-(4-Chloro-benzyl)-4-((+/−)trans-3-hydroxy-piperidin-4-yloxy)-N-isobutyl-benzenesulfonamide To a solution of (+/−)trans-4-{4-[(4-chloro-benzyl)-isobutyl-sulfamoyl]-phenoxy}-3-hydroxy-piperidine-1-carboxylic acid tert-butyl ester (222 mg, 402 µmol) in DCM (8 mL) was added TFA (2 mL) and the reaction was stirred at room temperature for 30 minutes. The reaction was concentrated and purified by SCX column eluting with 2 M NH$_3$ in MeOH to give N-(4-chloro-benzyl)-4-((+/−)trans-3-hydroxy-piperidin-4-yloxy)-N-isobutyl-benzenesulfonamide (202 mg, 447 µmol). LCMS (m/z, Method A) ES$^+$ 453 [M+1]$^+$.

Step 6: N-(4-Chloro-benzyl)-N-isobutyl-4-((+/−)trans-3-triisopropylsilanyloxy-piperidin-4-yloxy)-benzenesulfonamide To a solution of N-(4-chloro-benzyl)-4-((+/−)trans-3-hydroxy-piperidin-4-yloxy)-N-isobutyl-benzenesulfonamide (202 mg, 447 µmol) in DCM (10 mL) was added triethylamine (187 µL, 1.34 mmol) followed by triisopropylsilyltrifluoromethanesulfonate (132 µL, 492 µmol) and the reaction was stirred at room temperature for 1 hour. To the reaction was added Et$_3$N (187 µL, 1.34 mmol) followed by triisopropylsilyltrifluoromethanesulfonate (132 µL, 492 µmol) and reaction stirred for a further 30 minutes at room temperature. Water was added, and the mixture was extracted with DCM, filtered through a phase separator, concentrated then purified by silica gel column chromatography (0-10% MeOH in DCM) to give N-(4-chloro-benzyl)-N-isobutyl-4-((+/−)trans-3-triisopropylsilanyloxy-piperidin-4-yloxy)-benzenesulfonamide (189 mg, 70%). LCMS (m/z, Method A) ES$^+$ 609 [M+1]$^+$.

Step 7: N-(4-Chloro-benzyl)-N-isobutyl-4-((+/−)trans-1-methanesulfonyl-3-triisopropylsilanyloxy-piperidin-4-yloxy)-benzenesulfonamide To a solution of N-(4-chloro-benzyl)-N-isobutyl-4-((+/−)trans-3-triisopropylsilanyloxy-piperidin-4-yloxy)-benzenesulfonamide (185 mg, 304 µmol) in DCM (5 mL) was added DIPEA (106 µL, 609 µmol) followed by methanesulfonyl chloride (1 mL of a 231 µL, 3 mmol solution in 10 mL of DCM) and the reaction stirred at room temperature for 1 hour. Saturated aqueous NaHCO$_3$ was then added, extracted with DCM, filtered through a phase separator and concentrated to give N-(4-Chloro-benzyl)-N-isobutyl-4-((+/−)trans-1-methanesulfonyl-3-triisopropylsilanyloxy-piperidin-4-yloxy)-benzenesulfonamide (271 mg, 100%). LCMS (m/z, Method A) ES$^+$ 709 [M+23]$^+$.

Step 8: (N-(4-Chloro-benzyl)-4-((+/−)trans-3-hydroxy-1-methanesulfonyl-piperidin-4-yloxy)-N-isobutyl-benzenesulfonamide)

To a solution of N-(4-Chloro-benzyl)-N-isobutyl-4-((+/−)trans-1-methanesulfonyl-3-triisopropylsilanyloxy-piperidin-4-yloxy)-benzenesulfonamide (271 mg) in THF (5 mL) was added a 1 M solution of tetrabutylammonium fluoride in THF (609 µL, 609 mmol) and the reaction was stirred at room temperature for 30 minutes. Water was added and then extracted with EtOAc, washed with brine, dried with Na$_2$SO$_4$ then concentrated, purified by silica gel column chromatography (0-75% EtOAc in cyclohexane) and freeze dried to give the title compound (107 mg). $^1$H NMR (400 MHz, DMSO): δ 7.76 (d, 2H), 7.36-7.37 (m, 4H), 7.20 (d, 2H), 5.54 (d, 1H), 4.41 (td, 1H), 4.23 (s, 2H), 3.70-3.72 (m, 1H), 3.52 (dd, 1H), 3.42 (d, 1H), 3.04-3.08 (m, 1H), 2.94 (s, 3H), 2.90 (dd, 1H), 2.83 (d, 2H), 2.12-2.19 (m, 1H), 1.57-1.59 (m, 2H), 0.67 (d, 6H). LCMS (m/z, Method B) ES$^+$ 531 [M+1]$^+$.

Example 9

4-(4-Acetyl-piperazin-1-yl)-N-isobutyl-N-(2-trifluoromethyl-benzyl)-benzenesulfonamide

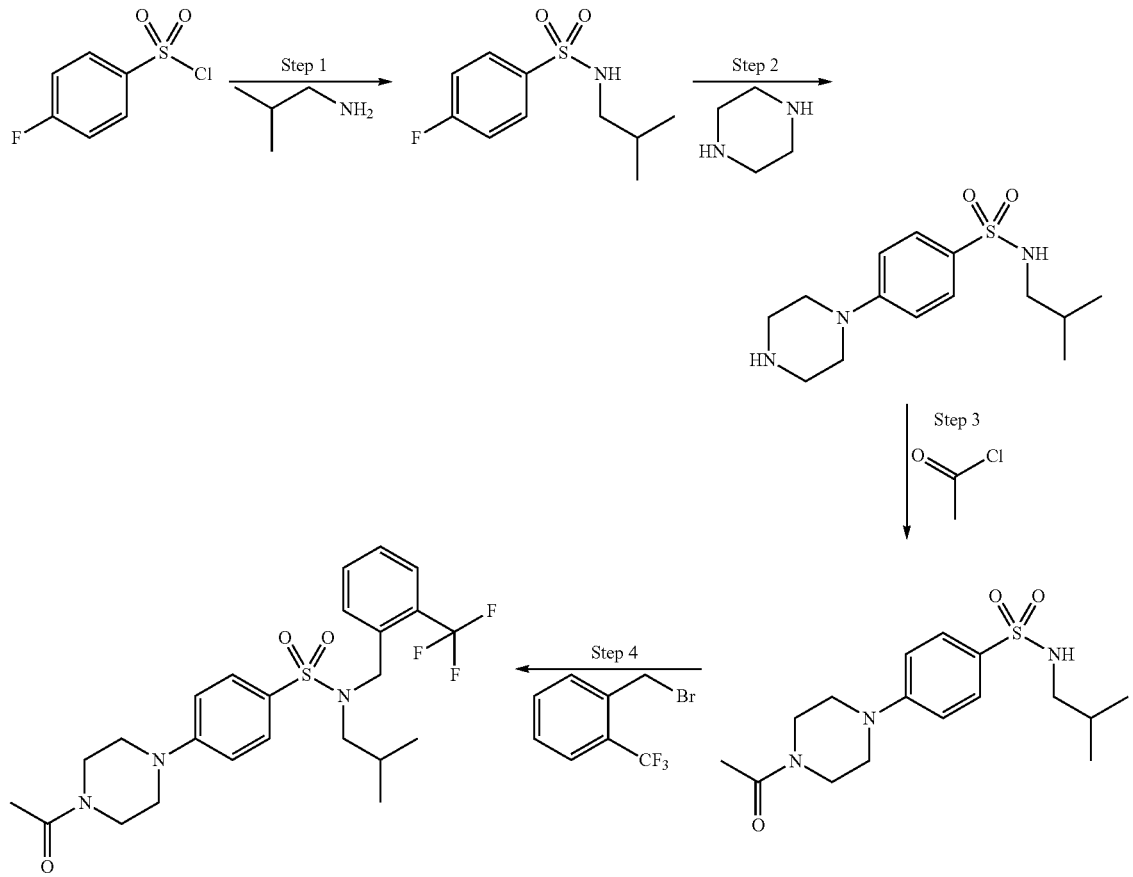

Step 1: 4-Fluoro-N-isobutyl-benzenesulfonamide

A solution of isobutylamine (6.64 mL, 66.8 mmol) and pyridine (6.24 mL, 77.1 mmol) in DCM (100 mL) was treated with 4-fluorobenzene sulfonyl chloride (10.0 g, 51.4 mmol) and stirred at room temperature for 18 hours. The mixture was diluted with DCM, washed with 1 N aqueous HCl, saturated aqueous NaHCO$_3$, water and brine, dried over Na$_2$SO$_4$ and concentrated under vacuum. Trituration with pentane gave 4-fluoro-N-isobutyl-benzenesulfonamide (10.48 g, 88%) as a pale yellow solid. $^1$H NMR (400 MHz, DMSO) δ 7.88-7.81 (m, 2H), 7.63 (t, J=6.1 Hz, 1H), 7.47-7.39 (m, 2H), 2.54 (t, J=6.5 Hz, 2H), 1.67-1.55 (m, 1H), 0.80 (d, J=6.7 Hz, 6H). LCMS (m/z, Method B) ES$^+$ 232.0 [M+1]$^+$.

Step 2: N-Isobutyl-4-piperazin-1-yl-benzenesulfonamide

A microwave vial was charged with 4-fluoro-N-isobutyl-benzenesulfonamide (1.0 g, 4.32 mmol), piperazine (1.86 g, 21.60 mmol) and water (20 mL) and heated at 150° C. for 1 hour using a microwave reactor. The solid from the reaction mixture was collected by filtration, washed with water and dried to give N-isobutyl-4-piperazin-1-yl-benzenesulfonamide (1.15 g, 90%). $^1$H NMR (300 MHz, CDCl$_3$) δ 7.70 (d, J=9.0 Hz, 2H), 6.90 (d, J=9.0 Hz, 2H), 4.33 (t, J=6.5 Hz, 1H), 3.32-3.25 (m, 4H), 3.05-2.99 (m, 4H), 2.73 (t, J=6.6 Hz, 2H), 1.78-1.65 (m, 1H), 0.87 (d, J=6.7 Hz, 7H). LCMS (m/z, Method A) ES$^+$ 298.2 [M+1]$^+$.

Step 3: 4-(4-Acetyl-piperazin-1-yl)-N-isobutyl-benzenesulfonamide

A solution of N-isobutyl-4-piperazin-1-yl-benzenesulfonamide (1.14 g, 3.83 mmol) and Et$_3$N (795 µL, 5.75 mmol) in DCM (25 mL) was treated with acetyl chloride (340 mL, 4.79 mmol) and stirred at room temperature for 30 minutes. The mixture was diluted with DCM, washed with 1 N aqueous HCl, saturated aqueous NaHCO$_3$, water and brine, dried over Na$_2$SO$_4$ and concentrated under vacuum. Purification by silica gel column chromatography (60-75% EtOAc in DCM) gave 4-(4-acetyl-piperazin-1-yl)-N-isobutyl-benzenesulfonamide (1.23 g, 95%) as a white solid. $^1$H NMR (400 MHz, DMSO) δ 7.58 (d, J=8.8 Hz, 2H), 7.27 (t, J=6.2 Hz, 1H), 7.04 (d, J=8.8 Hz, 2H), 3.62-3.54 (m, 4H), 3.38-3.26 (m, 8H), 2.49-2.43 (m, 2H), 2.04 (s, 3H), 1.65-1.54 (m, 1H), 0.80 (d, J=6.7 Hz, 6H). LCMS (m/z, Method B) ES$^+$ 340.0 [M+1]$^+$.

Step 4: (4-(4-Acetyl-piperazin-1-yl)-N-isobutyl-N-(2-trifluoromethyl-benzyl)-benzenesulfonamide)

A solution of 4-(4-acetyl-piperazin-1-yl)-N-isobutyl-benzenesulfonamide (100 mg, 0.295 mmol) in DMA (2 mL) was treated with NaH (60% dispersion in mineral oil, 18 mg, 0.443 mmol) and stirred at room temperature for 30 minutes. 2-(Trifluoromethyl)benzyl bromide (141 mg, 0.590 mmol) was added and the mixture heated at 90° C. for 1 hour. The cooled mixture was diluted with EtOAc, washed with water and brine, dried over $Na_2SO_4$ and concentrated under vacuum. Purification by silica gel column chromatography (0-100% EtOAc in DCM) gave the title compound (110 mg, 75%). $^1$H NMR (400 MHz, DMSO) δ 7.81 (d, J=7.9 Hz, 1H), 7.69-7.71 (m, 4H), 7.50 (t, J=7.6 Hz, 1H), 7.08 (d, J=8.8 Hz, 2H), 4.36 (s, 2H), 3.59 (d, J=5.26 Hz, 4H), 3.38 (dd, J=26.2, 5.0 Hz, 4H), 2.86 (d, J=7.2 Hz, 2H), 2.05 (s, 3H), 1.36 (t, J=6.7 Hz, 1H), 0.70 (d, J=6.6 Hz, 6H). LCMS (m/z Method B) ES$^+$ 498.1 [M+1]$^+$.

Example 10

N-(4-fluorobenzyl)-N-isobutyl-5-((1-(methylsulfonyl)piperidin-4-yl)oxy)pyridine-2-sulfonamide

Step 1: 4-(6-Chloro-pyridin-3-yloxy)-piperidine-1-carboxylic acid tert-butyl ester A solution of 2-chloro-5-hydroxy pyridine (5.00 g, 38.60 mmol), 1-Boc-4-hydroxypiperidine (9.32 g, 46.31 mmol) and triphenyl phosphine (15.19 g, 57.90 mmol) in THF (200 mL) at 0° C. was treated dropwise with diisopropylazodicarboxylate (11.14 mL, 57.90 mmol). The mixture was stirred at room temperature for 18 hours, diluted with EtOAc, washed with water and brine, dried over $Na_2SO_4$ and concentrated under vacuum. Purification by silica gel column chromatography (25-40% EtOAc in petrol (40-60° C.)) gave 4-(6-chloro-pyridin-3-yloxy)-piperidine-1-carboxylic acid tert-butyl ester (5.70 g, 47%) as a pale yellow residue. $^1$H NMR (300 MHz, CDCl$_3$) δ 8.06 (d, J=2.8 Hz, 1H), 7.23-7.16 (m, 2H), 4.51-4.41 (m, 1H), 3.75-3.64 (m, 2H), 3.40-3.29 (m, 2H), 1.99-1.86 (m, 2H), 1.83-1.67 (m, 2H), 1.47 (s, 9H). LCMS (m/z, Method A) ES$^+$ 311.1 [M+1]$^+$.

Step 2: 2-Chloro-5-(piperidin-4-yloxy)-pyridine

A solution of 4-(6-chloro-pyridin-3-yloxy)-piperidine-1-carboxylic acid tert-butyl ester (5.68 g, 18.16 mmol) in DCM (2 mL) was treated with TFA (25 mL) and stirred at room temperature for 1 hour. The mixture was concentrated under vacuum, dissolved in 1 N aqueous HCl and washed with EtOAc. The aqueous a phase was basified with ammonium hydroxide and extracted into EtOAc. The combined extracts were dried over $Na_2SO_4$ and concentrated under vacuum to give 2-chloro-5-(piperidin-4-yloxy)-pyridine (4.58 g) as a yellow solid. $^1$H NMR (300 MHz, DMSO) δ 8.54 (br s, 1H), 8.18 (d, J=3.1 Hz, 1H), 7.60-7.53 (m, 1H), 7.45 (d, J=8.8 Hz, 1H), 4.76-4.65 (m, 1H), 3.30-3.19 (m, 2H), 3.11-3.00 (m, 2H), 2.15-2.03 (m, 2H), 1.89-1.74 (m, 2H). LCMS (m/z, Method A) ES$^+$ 213.1 [M+1]$^+$.

Step 3: 2-Chloro-5-(1-methanesulfonyl-piperidin-4-yloxy)-pyridine

A solution of 2-chloro-5-(piperidin-4-yloxy)-pyridine (4.55 g, 21.39 mmol) and Et$_3$N (5.92 mL, 42.8 mmol) in

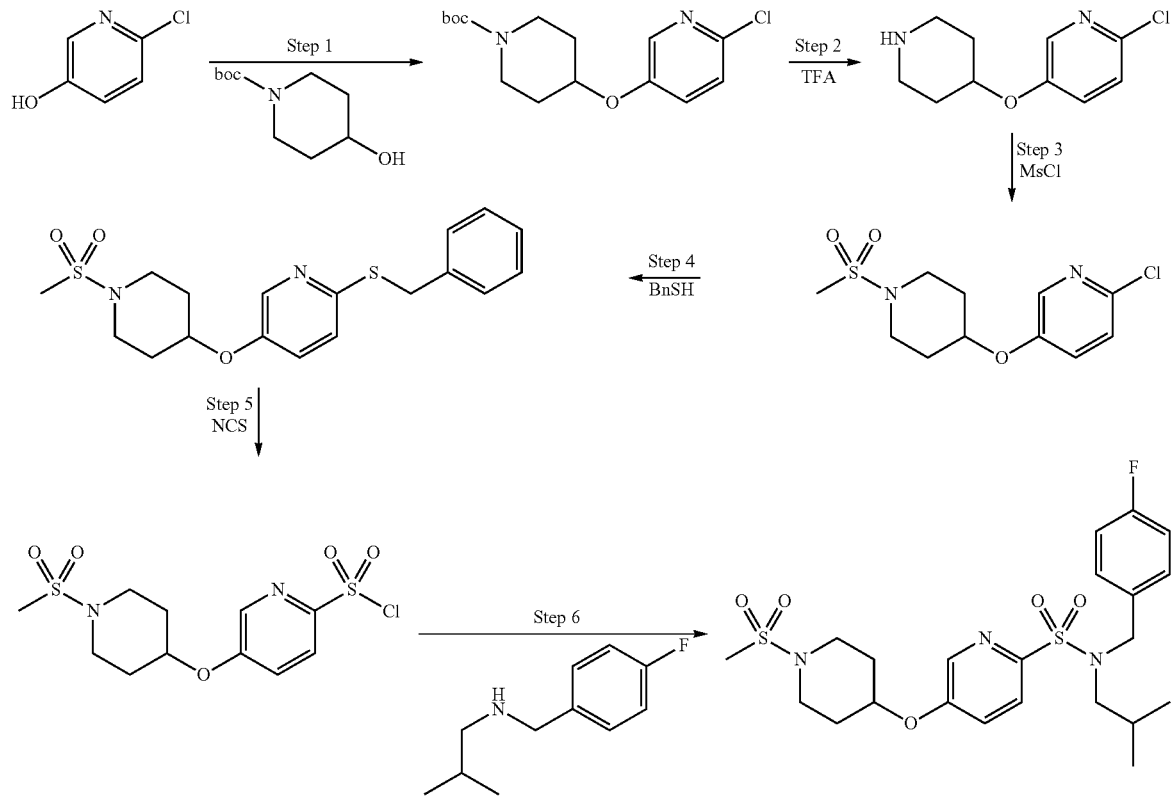

DCM (50 mL) was treated with methanesulfonyl chloride (2.48 mL, 32.09 mmol) and stirred at room temperature for 2 hours. The mixture was diluted with DCM, washed with 1 N aqueous HCl, saturated aqueous NaHCO$_3$, water and brine, dried over Na$_2$SO$_4$ and concentrated under vacuum. Purification by silica gel column chromatography (0-70% EtOAc in cyclohexane) gave 2-chloro-5-(1-methanesulfonyl-piperidin-4-yloxy)-pyridine (3.19 g, 51%). $^1$H NMR (300 MHz, CDCl$_3$) δ 8.07 (d, J=2.9 Hz, 1H), 7.28-7.16 (m, 2H), 4.58-4.49 (m, 1H), 3.44-3.28 (m, 4H), 2.83 (s, 3H), 2.13-1.92 (m, 4H). LCMS (m/z, Method A) ES$^+$ 290.9 [M+1]$^+$.

Step 4: 2-Benzylsulfanyl-5-(1-methanesulfonyl-piperidin-4-yloxy)-pyridine

A suspension of NaH (60% dispersion in mineral oil, 413 mg, 10.32 mmol) in dry DMF (12 mL) at 0° C. was treated dropwise with benzyl mercaptan (1.21 mL, 10.32 mmol). After the addition the mixture was stirred at room temperature for 15 minutes. 2-Chloro-5-(1-methanesulfonyl-piperidin-4-yloxy)-pyridine (1.00 g, 3.44 mmol) was added and the mixture stirred at room temperature for 18 hours, heated at 80° C. for a further 8 hours and allowed to cool overnight. The mixture was diluted with EtOAc, washed with water and brine, dried over Na$_2$SO$_4$ and concentrated under vacuum. Purified by silica gel column chromatography (30-50% EtOAc in cyclohexane) to give 2-benzylsulfanyl-5-(1-methanesulfonyl-piperidin-4-yloxy)-pyridine (659 mg, 51%). $^1$H NMR (300 MHz, CDCl$_3$) δ 8.20 (br s, 1H), 7.40-7.34 (m, 2H), 7.32-7.18 (s, 4H), 7.14-7.05 (m, 2H), 4.52-4.43 (m, 1H), 4.39 (s, 2H), 3.36 (t, J=5.6 Hz, 4H), 2.82 (s, 3H), 2.08-1.91 (m, 4H). LCMS (m/z, Method A) ES$^+$ 379.1 [M+1]$^+$.

Step 5: 5-(1-Methanesulfonyl-piperidin-4-yloxy)-pyridine-2-sulfonyl chloride A suspension of 2-benzylsulfanyl-5-(1-methanesulfonyl-piperidin-4-yloxy)-pyridine (650 mg, 1.72 mmol) in acetic acid (8 mL) and water (4 mL) at 0° C. was treated with N-chlorosuccinimide (917 mg, 6.87 mmol) and stirred at room temperature for 4 hours. The mixture was concentrated under vacuum and the aqueous a phase extracted with EtOAc. The combined extracts were washed with saturated aqueous NaHCO$_3$, water and brine, dried over Na$_2$SO$_4$ and concentrated under vacuum. Purification by silica gel column chromatography (0-100% EtOAc in cyclohexane) gave 5-(1-methanesulfonyl-piperidin-4-yloxy)-pyridine-2-sulfonyl chloride (269 mg, 44%). $^1$H NMR (300 MHz, CDCl$_3$) δ 8.43 (d, J=2.8 Hz, 1H), 8.08 (d, J=8.8 Hz, 1H), 7.38 (dd, J=8.8, 2.9 Hz, 1H), 4.79-4.71 (m, 1H), 3.50-3.33 (m, 4H), 2.85 (s, 3H), 2.21-1.99 (m, 4H). LCMS (m/z, Method A) ES$^+$ 355.1 [M+1]$^+$.

Step 6: (5-(1-Methanesulfonyl-piperidin-4-yloxy)-pyridine-2-sulfonic acid (4-fluoro-benzyl)-isobutyl-amide)

A solution of (4-fluorobenzyl)-isobutylamine (53 mg, 0.295 mmol) and pyridine (34 μL, 0.423 mmol) in DCM (3 mL) was treated with 5-(1-methanesulfonyl-piperidin-4-yloxy)-pyridine-2-sulfonyl chloride (75 mg, 0.211 mmol) and stirred at room temperature for 18 hours. The mixture was diluted with DCM, washed with 1 M aqueous citric acid, saturated aqueous NaHCO$_3$, water and brine, dried over Na$_2$SO$_4$ and concentrated under vacuum. Purification by silica gel column chromatography (0-100% EtOAc in cyclohexane) and re-purification by silica gel column chromatography (0-10% EtOAc in DCM) to give the title compound (39 mg, 37%). $^1$H NMR (400 MHz, DMSO) δ 8.45 (d, J=2.8 Hz, 1H), 7.89 (d, J=8.7 Hz, 1H), 7.66 (dd, J=8.8, 2.9 Hz, 1H), 7.38-7.32 (m, 2H), 7.17-7.09 (m, 2H), 4.84-4.76 (m, 1H), 4.39 (s, 2H), 3.43-3.34 (m, 2H), 3.18-3.10 (m, 2H), 3.00 (d, J=7.5 Hz, 2H), 2.92 (s, 3H), 2.11-2.01 (m, 2H), 1.84-1.73 (m, 2H), 1.63-1.52 (m, 1H), 0.68 (d, J=6.6 Hz, 6H). LCMS (m/z, Method B) ES$^+$ 499.9 [M+1]$^+$.

Example 11

1-Methanesulfonyl-piperidine-4-carboxylic acid {4-[isobutyl-(2-trifluoromethyl-phenyl)-sulfamoyl]-phenyl}-amide

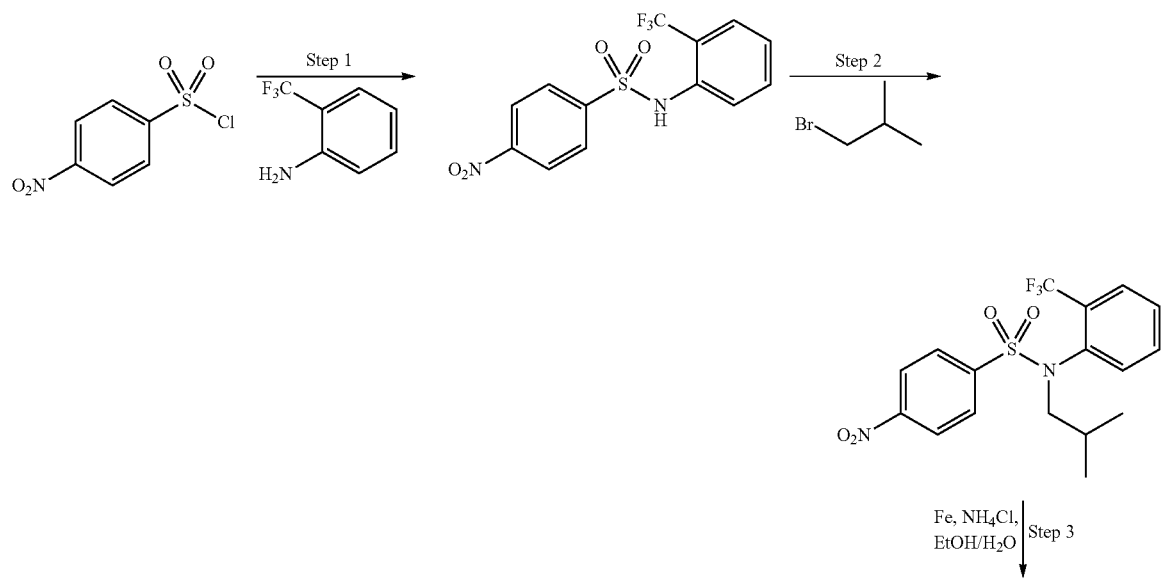

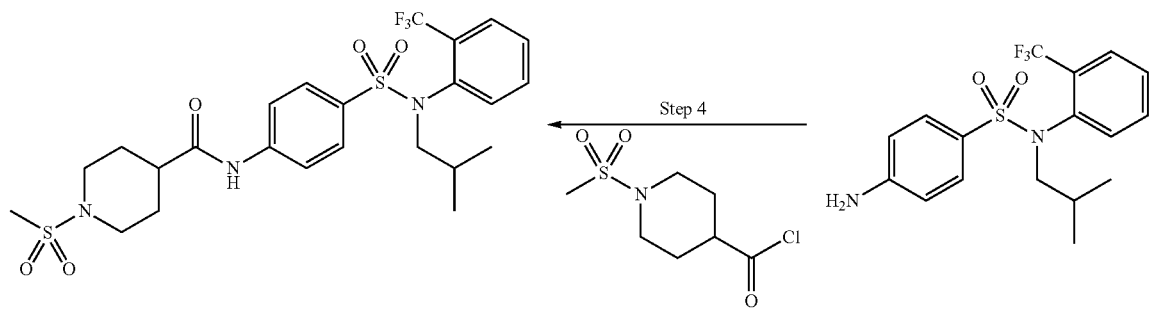

Step 1: 4-Nitro-N-(2-trifluoromethyl-phenyl)-benzenesulfonamide

A solution of 2-(trifluoromethyl)aniline (1.51 g, 9.37 mmol) and pyridine (1.08 mL, 13.38 mmol) in DCM (30 mL) was treated with 4-nitrobenzenesulfonyl chloride (1.48 g, 6.69 mmol) and stirred at room temperature for 18 hours. The mixture was diluted with DCM, washed with 1 M aqueous HCl, saturated aqueous NaHCO$_3$, water and brine, dried over Na$_2$SO$_4$ and concentrated under vacuum. Trituration with pentane gave 4-nitro-N-(2-trifluoromethyl-phenyl)-benzenesulfonamide (1.91 g, 82%). $^1$H NMR (300 MHz, CDCl$_3$) δ 8.31-8.23 (m, 2H), 7.95-7.85 (m, 3H), 7.64-7.50 (m, 2H), 7.31 (t, J=7.7 Hz, 1H), 6.89 (br s, 1H). LCMS (m/z, Method A) ES$^+$ 347.1 [M+1]$^+$.

Step 2: N-Isobutyl-4-nitro-N-(2-trifluoromethyl-phenyl)-benzenesulfonamide

A mixture of 4-nitro-N-(2-trifluoromethyl-phenyl)-benzenesulfonamide (1.90 g, 5.49 mmol), 1-bromo-2-methyl propane (1.19 mL, 10.97 mmol) and K$_2$CO$_3$ (1.51 g, 10.97 mmol) in DMF (20 mL) was heated at 100° C. for 18 hours. The cooled mixture was diluted with EtOAc, washed with water and brine, dried over Na$_2$SO$_4$ and concentrated under vacuum. Purification by silica gel column chromatography (0-30% EtOAc in cyclohexane) gave N-isobutyl-4-nitro-N-(2-trifluoromethyl-phenyl)-benzenesulfonamide (1.69 g, 77%). $^1$H NMR (300 MHz, CDCl$_3$) δ 8.34 (d, J=8.8 Hz, 2H), 7.88 (d, J=8.8 Hz, 2H), 7.78-7.70 (m, 1H), 7.61-7.47 (m, 2H), 7.23-7.16 (m, 1H), 3.48-3.31 (m, 2H), 1.76-1.60 (m, 1H), 0.88 (dd, J=10.1, 6.6 Hz, 6H). LCMS (m/z, Method A) ES$^+$ no mass ion observed.

Step 3: 4-Amino-N-isobutyl-N-(2-trifluoromethyl-phenyl)-benzenesulfonamide

A partial solution of N-isobutyl-4-nitro-N-(2-trifluoromethyl-phenyl)-benzenesulfonamide (1.68 g, 4.19 mmol), in EtOH (IMS grade, 50 mL) and water (15 mL) was treated with iron powder (~325 mesh, 936 mg, 16.76 mmol) and ammonium chloride (896 mg, 16.76 mmol) and heated at reflux for 1 hour. The cooled mixture was filtered through diatomaceous earth washing the filter cake with EtOH and the filtrate concentrated to low volume under vacuum. The residue obtained was diluted with water and extracted into DCM. The combined extracts were dried over Na$_2$SO$_4$ and concentrated under vacuum. Purification by silica gel column chromatography (0-75% EtOAc in cyclohexane) gave 4-amino-N-isobutyl-N-(2-trifluoromethyl-phenyl)-benzenesulfonamide (1.53 g, 98%). $^1$H NMR (300 MHz, CDCl$_3$) δ 7.72 (dd, J=7.5, 2.1 Hz, 1H), 7.54-7.39 (m, 4H), 7.14 (d, J=7.7 Hz, 1H), 6.70-6.63 (m, 2H), 3.35 (dd, J=13.5, 8.3 Hz, 1H), 3.15 (dd, J=13.5, 5.3 Hz, 1H), 1.71-1.55 (m, 1H), 0.88 (d, J=6.5 Hz, 3H), 0.77 (d, J=6.7 Hz, 3H). LCMS (m/z, Method A) ES$^+$ 373.1 [M+1]$^+$.

Step 4: (1-Methanesulfonyl-piperidine-4-carboxylic acid {4-[isobutyl-(2-trifluoromethyl-phenyl)-sulfamoyl]-phenyl}-amide)

A solution of 4-amino-N-isobutyl-N-(2-trifluoromethyl-phenyl)-benzenesulfonamide (100 mg, 0.268 mmol), 1-(methylsulfonyl)-4-piperidinecarbonyl chloride (108 mg, 0.48 mmol) and DIPEA (138 µL, 0.804 mmol) in DCM (8 mL) was stirred at room temperature for 3 hours. The mixture was diluted with DCM, washed with 1 N aqueous HCl, saturated aqueous NaHCO$_3$, water and brine, dried over Na$_2$SO$_4$ and concentrated under vacuum. Purification by silica gel column chromatography (0-100% EtOAc in cyclohexane) and triturating with Et$_2$O/pentane gave the title compound (98 mg, 65%). $^1$H NMR (400 MHz, DMSO δ 10.42 (s, 1H), 7.85 (d, J=8.8 Hz, 2H), 7.82 (dd, J=7.7, 1.9 Hz, 1H), 7.62-7.63 (m, 1H), 7.58 (d, J=8.8 Hz, 2H), 6.99 (d, J=7.8 Hz, 1H), 3.63 (d, J=11.8 Hz, 2H), 3.38-3.39 (m, 1H), 3.11 (dd, J=13.4, 4.7 Hz, 1H), 2.90 (s, 3H), 2.76-2.78 (m, 2H), 1.95 (d, J=13.5 Hz, 2H), 1.63-1.68 (m, 2H), 1.44-1.48 (m, 1H), 1.09 (t, J=7.0 Hz, 1H), 0.88 (d, J=6.5 Hz, 3H), 0.71 (d, J=6.7 Hz, 3H). LCMS (m/z, Method B) ES$^+$ 562.0 [M+1]$^+$.

Example 12

4-[(4-Fluoro-phenyl)-isobutyl-sulfamoyl]-N-(1-methanesulfonyl-piperidin-4-yl)-benzamide

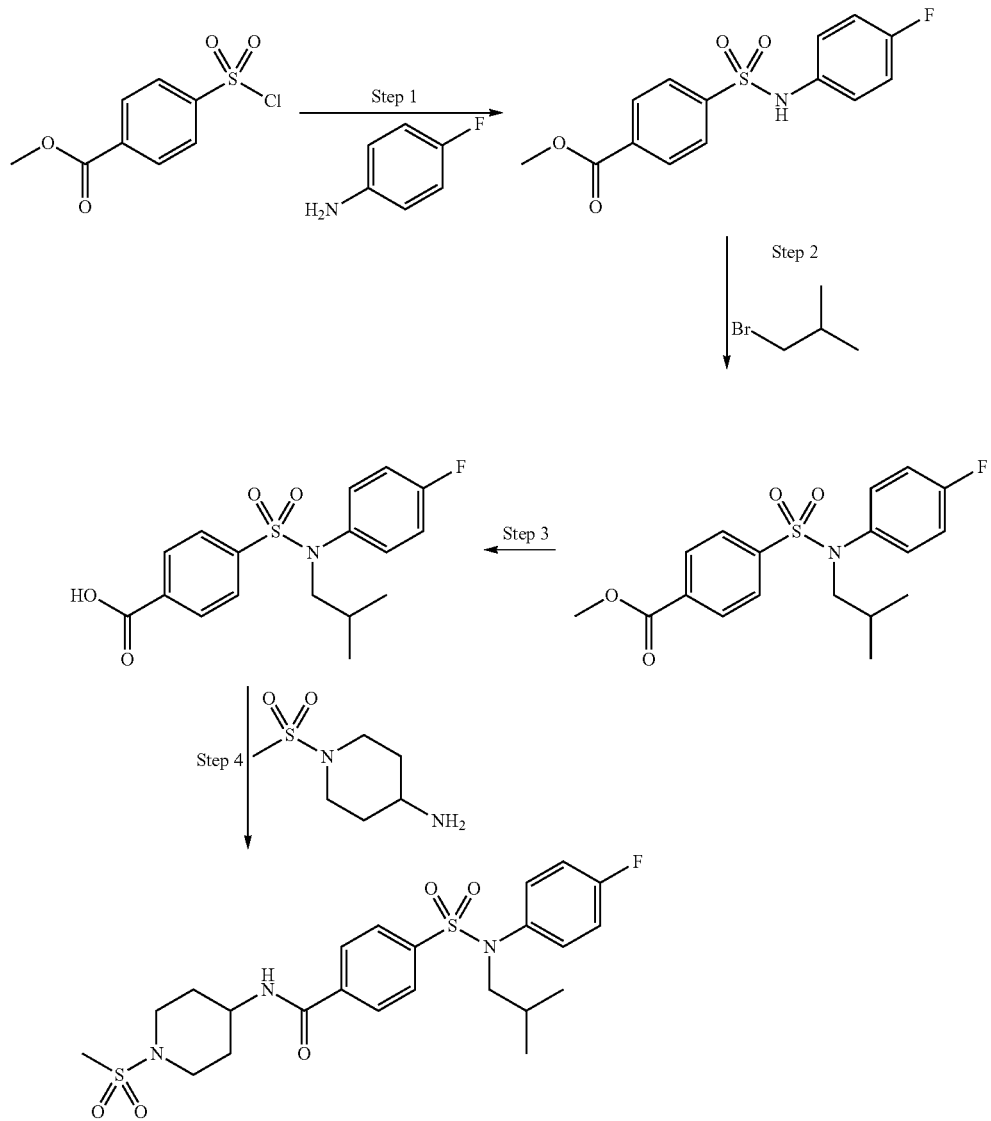

Step 1: 4-(4-Fluoro-phenylsulfamoyl)-benzoic acid methyl ester

A solution of 4-fluoroaniline (484 µL, 5.11 mmol) and pyridine (688 µL, 8.52 mmol) in DCM (20 mL) was treated with methyl 4-(chlorosulfonyl)benzoate (1.00 g, 4.26 mmol) and stirred at room temperature for 3 hours. The mixture was diluted with DCM, washed with 1 N aqueous HCl, saturated aqueous $NaHCO_3$, water and brine, dried over $Na_2SO_4$ and concentrated under vacuum. Triturating with pentane gave 4-(4-fluoro-phenylsulfamoyl)-benzoic acid methyl ester (1.02 g, 77%). $^1$H NMR (300 MHz, $CDCl_3$) δ 8.10 (d, J=8.4 Hz, 2H), 7.78 (d, J=8.4 Hz, 2H), 7.07-6.99 (m, 2H), 6.98-6.88 (m, 2H), 6.75 (br s, 1H), 3.94 (s, 3H). LCMS (m/z, Method A) $ES^+$ 310.0 $[M+1]^+$.

Step 2: 4-[(4-Fluoro-phenyl)-isobutyl-sulfamoyl]-benzoic acid methyl ester

A mixture of 4-(4-fluoro-phenylsulfamoyl)-benzoic acid methyl ester (1.00 g, 3.23 mmol), 1-bromo-2-methyl propane (527 µL, 4.85 mmol), and $K_2CO_3$ (891 mg, 6.46 mmol) in DMF (10 mL) was heated at 90° C. for 18 hours. The cooled mixture was diluted with EtOAc, washed with water and brine, dried over $Na_2SO_4$ and concentrated under vacuum. Purification by silica gel column chromatography (0-50% EtOAc in cyclohexane) gave 4-[(4-fluoro-phenyl)-isobutyl-sulfamoyl]-benzoic acid methyl ester (1.69 g, 77%). $^1$H NMR (300 MHz, $CDCl_3$) δ 8.12 (d, J=8.3 Hz, 2H), 7.63 (d, J=8.3 Hz, 2H), 6.99 (d, J=6.5 Hz, 4H), 3.96 (s, 3H), 3.31 (d, J=7.3 Hz, 2H), 1.58-1.56 (m, 1H), 0.92 (d, J=6.7 Hz, 6H). LCMS (m/z, Method A) $ES^+$ 366.1 $[M+1]^+$.

Step 3: 4-[(4-Fluoro-phenyl)-isobutyl-sulfamoyl]-benzoic acid

A solution of 4-[(4-fluoro-phenyl)-isobutyl-sulfamoyl]-benzoic acid methyl ester (1.05 g, 2.87 mmol) in MeOH (40 mL) was treated with 1 M aqueous NaOH (8.6 mL, 8.60 mmol) and stirred at room temperature for 2.5 hours. The MeOH was removed under vacuum, the aqueous a phase diluted with water, washed with EtOAc and acidified to pH 1-2 using 1 N aqueous HCl. The acidic aqueous was extracted with EtOAc. The combined extracts were dried over $Na_2SO_4$ and concentrated under vacuum to give 4-[(4-fluoro-phenyl)-isobutyl-sulfamoyl]-benzoic acid (914 mg, 91%). $^1$H NMR (300 MHz, DMSO) δ 13.48 (br s, 1H), 8.10 (d, J=8.3 Hz, 2H), 7.65 (d, J=8.3 Hz, 2H), 7.25-7.05 (m, 4H), 3.35 (d, J=7.3 Hz, 2H), 1.51-1.33 (m, 1H), 0.85 (d, J=6.6 Hz, 6H). LCMS (m/z, Method A) ES$^+$ 352.0 [M+1]$^+$.

Step 4: 4-[(4-Fluoro-phenyl)-isobutyl-sulfamoyl]-N-(1-methanesulfonyl-piperidin-4-yl)-benzamide A solution of 4-[(4-fluoro-phenyl)-isobutyl-sulfamoyl]-benzoic acid (100 mg, 0.285 mmol), 4-amino-1-methanesulfonyl piperidine (66 mg, 0.370 mmol) and DIPEA (146 μL, 0.855 mmol) in DMF (2 mL) was treated with HATU (162 mg, 0.428 mmol) and stirred at room temperature for 18 hours. The mixture was diluted with EtOAc, washed with 1 N aqueous HCl, saturated aqueous NaHCO$_3$, water and brine, dried over Na$_2$SO$_4$ and concentrated under vacuum. Purification by silica gel column chromatography (0-50% EtOAc in DCM) and triturating with Et$_2$O gave the title compound (124 mg, 85%). $^1$H NMR (400 MHz, DMSO) δ 8.60 (d, J=7.6 Hz, 1H), 8.00 (d, J=8.3 Hz, 2H), 7.63 (d, J=8.3 Hz, 2H), 7.20 (t, J=8.7 Hz, 2H), 7.11 (dd, J=8.8, 5.0 Hz, 2H), 3.93-3.95 (m, 1H), 3.58 (d, J=11.8 Hz, 2H), 2.88 (s, 5H), 1.93 (s, 1H), 1.90 (s, 2H), 1.58-1.61 (m, 2H), 1.42-1.44 (m, 1H), 0.85 (d, J=6.6 Hz, 6H). LCMS (m/z, Method B) ES$^+$ 511.8 [M+1]$^+$.

Example 13

N-Isobutyl-4-(1-methanesulfonyl-piperidin-4-ylidenemethyl)-N-(2-trifluoromethyl-benzyl)-benzenesulfonamide

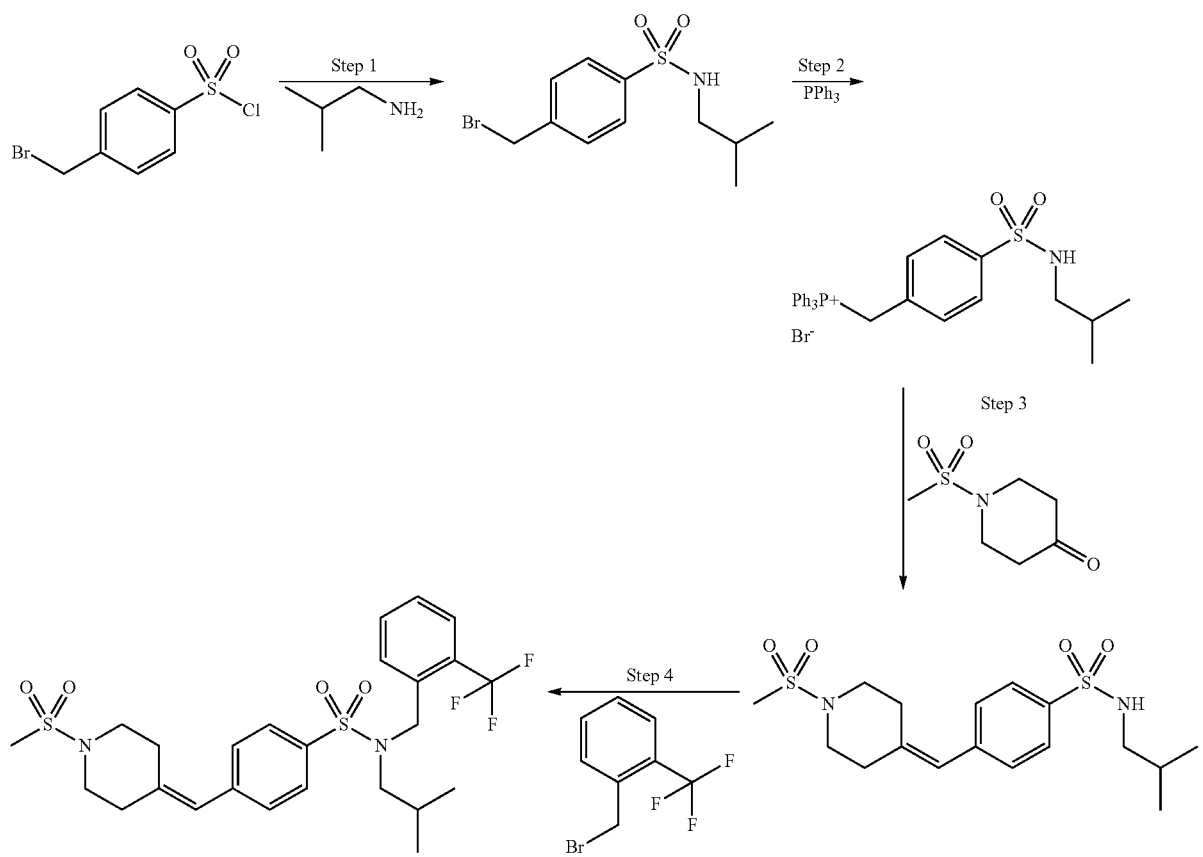

Step 1: 4-Bromomethyl-N-isobutyl-benzenesulfonamide

A solution of isobutylamine (1.10 mL, 11.14 mmol) and pyridine (600 μL, 7.42 mmol) in DCM (60 mL) was treated with 4-(bromomethyl)benzene sulfonyl chloride (2.00 g, 7.42 mmol) and stirred at room temperature for 1.5 hours. The mixture was diluted with DCM, washed with 1 N aqueous HCl, saturated aqueous NaHCO$_3$, water and brine, dried over Na$_2$SO$_4$ and concentrated under vacuum. Purification by silica gel column chromatography (0-50% EtOAc in cyclohexane) gave 4-bromomethyl-N-isobutyl-benzenesulfonamide (1.08 g, 48%). $^1$H NMR (300 MHz, CDCl$_3$) δ 7.83 (d, J=8.1 Hz, 2H), 7.53 (d, J=8.1 Hz, 2H), 4.50 (s, 2H), 4.43 (t, J=6.4 Hz, 1H), 2.78 (t, J=6.6 Hz, 2H), 1.81-1.65 (m, 1H), 0.88 (d, J=6.7 Hz, 6H). LCMS (m/z, Method A) ES⁺ 308.0 [M+Na]⁺.

Step 2: 4-Isobutylsulfamoyl-benzyl-phosphonium bromide

A mixture of 4-bromomethyl-N-isobutyl-benzenesulfonamide (1.08 g, 3.53 mmol) and triphenylphosphine (1.39 g, 5.29 mmol) in toluene (20 mL) was heated at reflux for 18 hours. The precipitate was collected from the cooled mixture, washed with toluene and air dried to give 4-isobutylsulfamoyl-benzyl-phosphonium bromide (1.88 g, 94%). ¹H NMR (300 MHz, DMSO) δ 7.96-7.88 (m, 2H), 7.79-7.56 (m, 15H), 7.20-7.13 (m, 2H), 5.29 (d, J=16.1 Hz, 2H), 2.53-2.46 (m, 2H), 1.64-1.48 (m, 1H), 0.77 (d, J=6.7 Hz, 6H). LCMS (m/z, Method A) ES⁺ 488.1 [M+Na]⁺.

Step 3: N-Isobutyl-4-(1-methanesulfonyl-piperidin-4-ylidenemethyl)-benzenesulfonamide A solution of 4-isobutylsulfamoyl-benzyl-phosphonium bromide (1.87 g, 3.29 mmol) in DMF (10 mL) was treated with NaH (60% dispersion in mineral oil, 329 mg, 8.22 mmol) and stirred at room temperature for 1 hour. 1-(Methylsulfonyl)piperidin-4-one (758 mg, 4.28 mmol) was added and the mixture stirred at room temperature for 18 hours. The mixture was diluted with EtOAc, washed with water and brine, dried over Na₂SO₄ and concentrated under vacuum. Purification by silica gel column chromatography (0-100% EtOAc in cyclohexane) gave N-isobutyl-4-(1-methanesulfonyl-piperidin-4-ylidenemethyl)-benzenesulfonamide (392 mg, 31%). ¹H NMR (300 MHz, CDCl₃) δ 7.81 (d, J=8.2 Hz, 2H), 7.31 (d, J=8.2 Hz, 2H), 6.43 (s, 1H), 4.40 (t, J=6.5 Hz, 1H), 3.37 (t, J=5.7 Hz, 2H), 3.25 (t, J=5.8 Hz, 2H), 2.82-2.76 (m, 5H), 2.60 (t, J=5.7 Hz, 2H), 2.53 (t, J=5.7 Hz, 2H), 1.80-1.66 (m, 1H), 0.88 (d, J=6.7 Hz, 6H). LCMS (m/z, Method A) ES⁺ 523.1 [M+Na]⁺.

Step 4: (N-Isobutyl-4-(1-methanesulfonyl-piperidin-4-ylidenemethyl)-N-(2-trifluoromethyl-benzyl)-benzenesulfonamide)

A mixture of N-isobutyl-4-(1-methanesulfonyl-piperidin-4-ylidenemethyl)-benzenesulfonamide (375 mg, 0.97 mmol), 2-(trifluoromethyl)benzyl bromide (289 mg, 1.22 mmol) and K₂CO₃ (201 mg, 1.46 mmol) in DMF (5 mL) was heated at 110° C. for 6 hours. The cooled mixture was diluted with EtOAc, washed with water and brine, dried over Na₂SO₄ and concentrated under vacuum. Purification by silica gel column chromatography (0-100% EtOAc in cyclohexane) and concentrating the residue from Et₂O gave the title compound (290 mg, 55%). ¹H NMR (400 MHz, DMSO) δ 7.83 (d, J=8.3 Hz, 2H), 7.70-7.73 (m, 3H), 7.49 (t, J=8.1 Hz, 3H), 6.51 (s, 1H), 4.46 (s, 2H), 3.22 (dt, J=30.4, 5.7 Hz, 4H), 2.96 (d, J=7.3 Hz, 2H), 2.89 (s, 3H), 2.49-2.50 (m, 4H), 1.39-1.40 (m, 1H), 0.70 (d, J=6.6 Hz, 6H). LCMS (m/z, Method B) ES⁺ 544.9 [M+1]⁺.

Example 14

4-(Hydroxyl(1-(methylsulfonyl)piperidin-4-yl)methyl-N-isobutyl-N-(2-(trifluoromethyl)benzyl)benzenesulfonamide

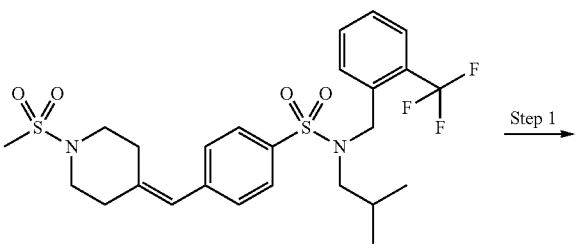

Step 1

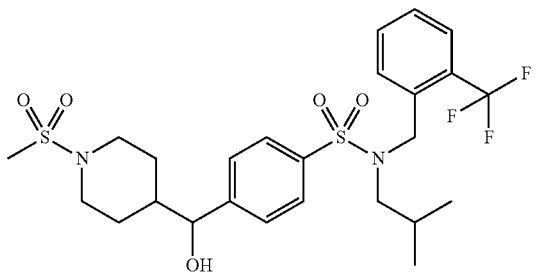

A solution of N-isobutyl-4-(1-methanesulfonyl-piperidin-4-ylidenemethyl)-N-(2-trifluoromethyl-benzyl)-benzenesulfonamide (1.05 g, 1.93 mmol) in THF (5 mL) under a nitrogen atmosphere was treated with borane THF complex (1.0 M solution in THF, 15.4 mL, 15.4 mmol) and stirred at room temperature for 2 hours. The reaction mixture was cooled to 0° C. and quenched by addition of 95% ethanol (IMS grade), 2 M aqueous NaOH (10 mL) and hydrogen peroxide (50 wt % in water, 10 mL). The mixture was stirred for 1 hour, diluted with saturated aqueous NH₄Cl, and extracted with EtOAc. The combined extracts were washed with brine, dried over Na₂SO₄ and concentrated under vacuum. Purification by silica gel column chromatography (0-100% EtOAc in cyclohexane) and re-purification by preparative reverse a phase HPLC (gradient 30-98% acetonitrile in water with 0.1% formic acid) followed by silica gel column chromatography (0-20% EtOAc in DCM) gave the title compound (75 mg, 7%). ¹H NMR (400 MHz, DMSO) δ 7.83 (d, J=8.2 Hz, 2H), 7.70-7.69 (m, 3H), 7.55 (d, J=8.1 Hz, 2H), 7.52-7.47 (m, 1H), 5.52 (d, J=4.5 Hz, 1H), 4.50-4.43 (m, 3H), 3.61-3.49 (m, 2H), 2.94 (m, 2H), 2.81 (s, 3H), 2.64-2.53 (m, 2H), 1.83-1.75 (m, 1H), 1.67-1.56 (m, 1H), 1.44-1.20 (m, 4H), 0.69 (d, J=6.6 Hz, 6H). LCMS (m/z, Method B) ES⁺ 563.0[M+1]⁺.

The above compounds, together with additional compounds made using the above procedure, are shown in Table 1 below, together with RORc IC₅₀ (micromolar) data for selected compounds determined from the assay described below.

TABLE 1

| | Structure | Name | (IC$_{50}$) [uM] |
|---|---|---|---|
| 1 | 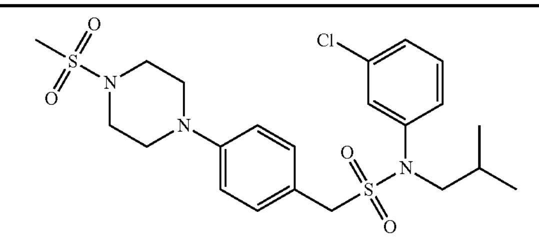 | N-(3-chlorophenyl)-N-isobutyl-1-(4-(4-(methylsulfonyl)piperazin-1-yl)phenyl)methanesulfonamide | |
| 2 | 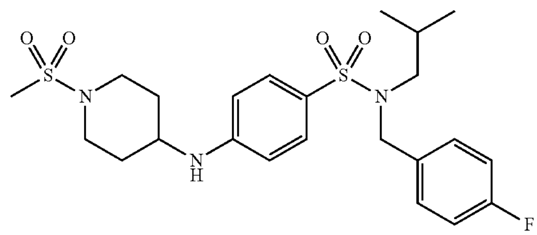 [SMILES: CC(C)CN(Cc1ccc(F)cc1)S(=O)(=O)c1ccc(NC2CCN(S(C)(=O)=O)CC2)cc1] | N-(4-Fluoro-benzyl)-N-isobutyl-4-(1-methanesulfonyl-piperidin-4-ylamino)-benzenesulfonamide | 0.008 |
| 3 | 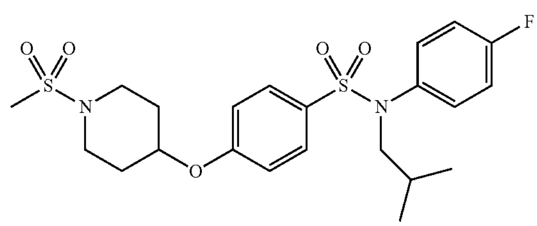 [SMILES: CC(C)CN(c1ccc(F)cc1)S(=O)(=O)c1ccc(OC2CCN(S(C)(=O)=O)CC2)cc1] | N-(4-Fluoro-phenyl)-N-isobutyl-4-(1-methanesulfonyl-piperidin-4-yloxy)-benzenesulfonamide | 0.016 |
| 4 | 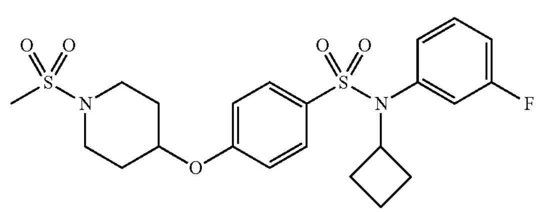 [SMILES: CS(=O)(=O)N1CCC(Oc2ccc(S(=O)(=O)N(c3cccc(F)c3)C3CCC3)cc2)CC1] | N-Cyclobutyl-N-(3-fluoro-phenyl)-4-(1-methanesulfonyl-piperidin-4-yloxy)-benzenesulfonamide | 0.029 |
| 5 | 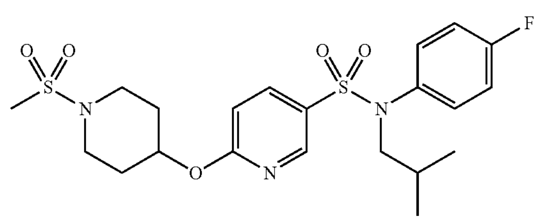 [SMILES: CC(C)CN(c1ccc(F)cc1)S(=O)(=O)c1ccc(OC2CCN(S(C)(=O)=O)CC2)nc1] | N-(4-fluorophenyl)-N-isobutyl-6-((1-(methylsulfonyl)piperidin-4-yl)oxy)pyridine-3-sulfonamide | |
| 6 | 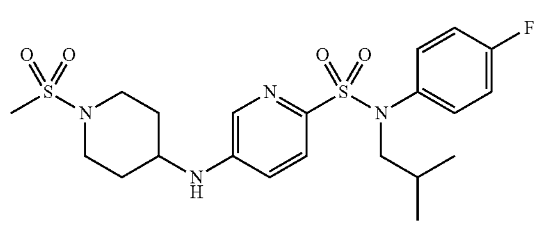 [SMILES: CC(C)CN(c1ccc(F)cc1)S(=O)(=O)c1ccc(NC2CCN(S(C)(=O)=O)CC2)cn1] | N-(4-fluorophenyl)-N-isobutyl-5-((1-(methylsulfonyl)piperidin-4-yl)amino)pyridine-2-sulfonamide | |
| 7 | 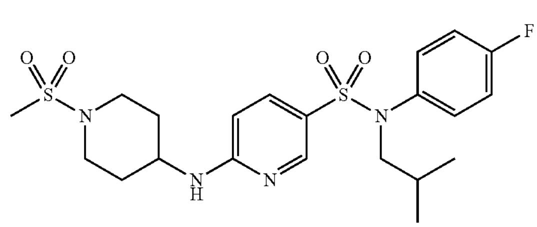 [SMILES: CC(C)CN(c1ccc(F)cc1)S(=O)(=O)c1ccc(NC2CCN(S(C)(=O)=O)CC2)nc1] | N-(4-fluorophenyl)-N-isobutyl-6-((1-(methylsulfonyl)piperidin-4-yl)amino)pyridine-3-sulfonamide | |

TABLE 1-continued

| | Structure | Name | (IC$_{50}$) [uM] |
|---|---|---|---|
| 8 | 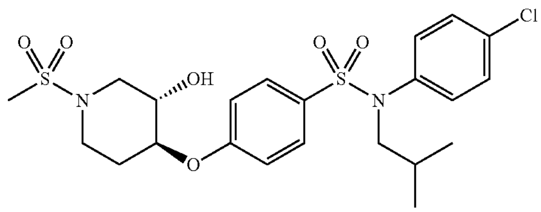 [SMILES: CC(C)CN(c1ccc(Cl)cc1)S(=O)(=O)c1ccc(O[C@H]2CCN(S(C)(=O)=O)C[C@@H]2O)cc1] | N-(4-chlorophenyl)-4-(((+/−)trans-3-hydroxy-1-(methylsulfonyl)piperidin-4-yl)oxy)-N-isobutylbenzenesulfonamide | |
| 9 | 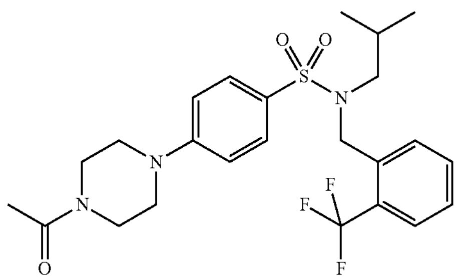 [SMILES: CC(=O)N1CCN(c2ccc(S(=O)(=O)N(Cc3ccccc3C(F)(F)F)CC(C)C)cc2)CC1] | 4-(4-Acetyl-piperazin-1-yl)-N-isobutyl-N-(2-trifluoromethyl-benzyl)-benzenesulfonamide | 0.009 |
| 10 | 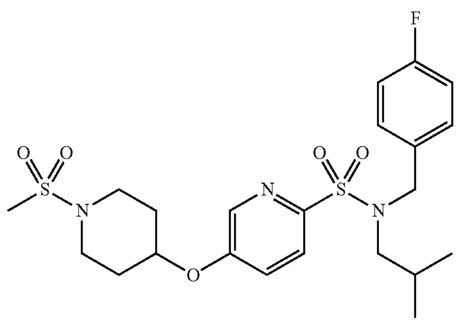 [SMILES: CC(C)CN(Cc1ccc(F)cc1)S(=O)(=O)c1ccc(OC2CCN(S(C)(=O)=O)CC2)cn1] | N-(4-fluorobenzyl)-N-isobutyl-5-((1-(methylsulfonyl)piperidin-4-yl)oxy)pyridine-2-sulfonamide | |
| 11 | 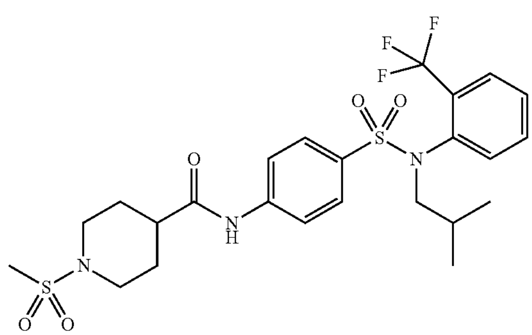 [SMILES: CC(C)CN(c1ccccc1C(F)(F)F)S(=O)(=O)c1ccc(NC(=O)C2CCN(S(C)(=O)=O)CC2)cc1] | 1-Methanesulfonyl-piperidine-4-carboxylic acid {4-[isobutyl-(2-trifluoromethyl-phenyl)-sulfamoyl]-phenyl}-amide | 0.013 |
| 12 | 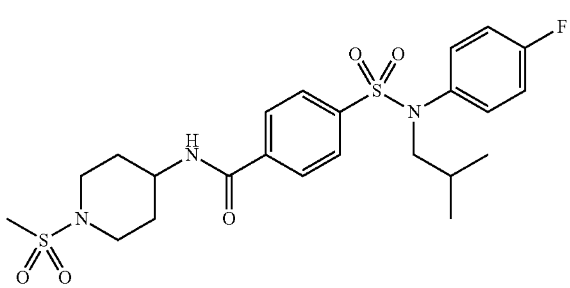 [SMILES: CC(C)CN(c1ccc(F)cc1)S(=O)(=O)c1ccc(C(=O)NC2CCN(S(C)(=O)=O)CC2)cc1] | 4-[(4-Fluoro-phenyl)-isobutyl-sulfamoyl]-N-(1-methanesulfonyl-piperidin-4-yl)-benzamide | 6.1 |

TABLE 1-continued

| | Structure | Name | (IC$_{50}$) [uM] |
|---|---|---|---|
| 13 | 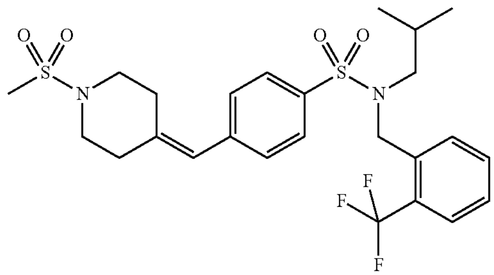 [SMILES: CC(C)CN(Cc1ccccc1C(F)(F)F)S(=O)(=O)c1ccc(C=C2CCN(S(C)(=O)=O)CC2)cc1] | N-Isobutyl-4-(1-methanesulfonyl-piperidin-4-ylidenemethyl)-N-(2-trifluoromethyl-benzyl)-benzenesulfonamide | 0.014 |
| 14 | 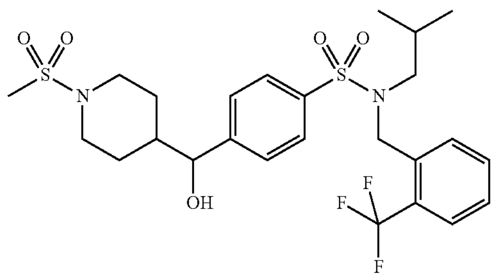 [SMILES: CC(C)CN(Cc1ccccc1C(F)(F)F)S(=O)(=O)c1ccc(C(O)C2CCN(S(C)(=O)=O)CC2)cc1] | 4-(hydroxyl(1-(methylsulfonyl)piperidin-4-yl)methyl-N-isobutyl-N-(2-(trifluoromethyl)benzyl) benzenesulfonamide | |
| 15 | 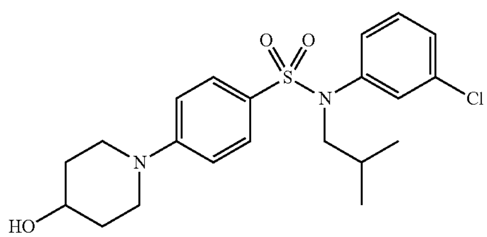 [SMILES: CC(C)CN(c1cccc(Cl)c1)S(=O)(=O)c1ccc(N2CCC(O)CC2)cc1] | N-(3-Chloro-phenyl)-4-(4-hydroxy-piperidin-1-yl)-N-isobutyl-benzenesulfonamide | 0.771 |
| 16 | 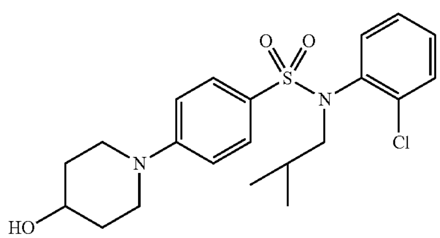 [SMILES: CC(C)CN(c1ccccc1Cl)S(=O)(=O)c1ccc(N2CCC(O)CC2)cc1] | N-(2-Chloro-phenyl)-4-(4-hydroxy-piperidin-1-yl)-N-isobutyl-benzenesulfonamide | 1.3 |
| 17 | 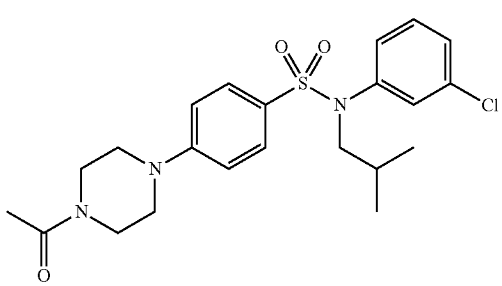 [SMILES: CC(=O)N1CCN(c2ccc(S(=O)(=O)N(CC(C)C)c3cccc(Cl)c3)cc2)CC1] | 4-(4-Acetyl-piperazin-1-yl)-N-(3-chloro-phenyl)-N-isobutyl-benzenesulfonamide | 0.138 |
| 18 | 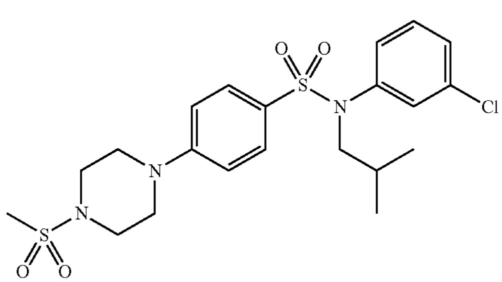 [SMILES: CC(C)CN(c1cccc(Cl)c1)S(=O)(=O)c1ccc(N2CCN(S(C)(=O)=O)CC2)cc1] | N-(3-Chloro-phenyl)-N-isobutyl-4-(4-methanesulfonyl-piperazin-1-yl)-benzenesulfonamide | 0.126 |

TABLE 1-continued

| | Structure | Name | (IC$_{50}$) [uM] |
|---|---|---|---|
| 19 | 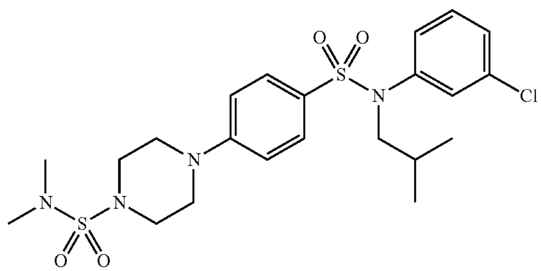 [SMILES: CC(C)CN(c1cccc(Cl)c1)S(=O)(=O)c1ccc(N2CCN(S(=O)(=O)N(C)C)CC2)cc1] | 4-{4-[(3-Chloro-phenyl)-isobutyl-sulfamoyl]-phenyl}-piperazine-1-sulfonic acid dimethylamide | 0.062 |
| 20 | 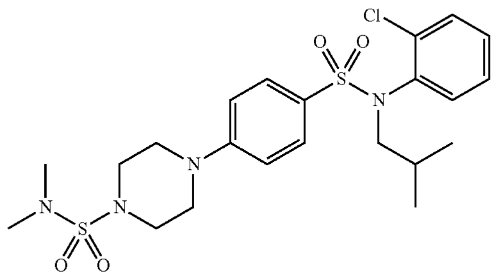 [SMILES: CC(C)CN(c1ccccc1Cl)S(=O)(=O)c1ccc(N2CCN(S(=O)(=O)N(C)C)CC2)cc1] | 4-{4-[(2-Chloro-phenyl)-isobutyl-sulfamoyl]-phenyl}-piperazine-1-sulfonic acid dimethylamide | 0.081 |
| 21 | 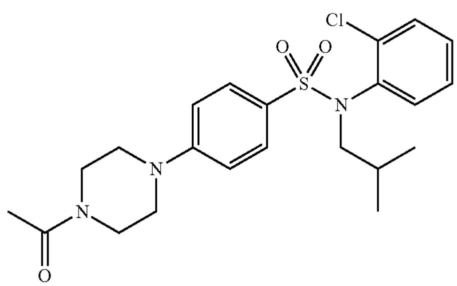 [SMILES: CC(=O)N1CCN(c2ccc(S(=O)(=O)N(CC(C)C)c3ccccc3Cl)cc2)CC1] | 4-(4-Acetyl-piperazin-1-yl)-N-(2-chloro-phenyl)-N-isobutyl-benzenesulfonamide | 0.099 |
| 22 | 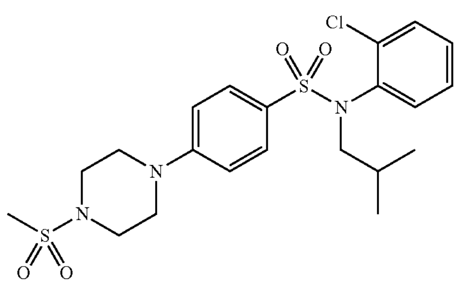 [SMILES: CC(C)CN(c1ccccc1Cl)S(=O)(=O)c1ccc(N2CCN(S(C)(=O)=O)CC2)cc1] | N-(2-Chloro-phenyl)-N-isobutyl-4-(4-methanesulfonyl-piperazin-1-yl)-benzenesulfonamide | 0.087 |
| 23 | 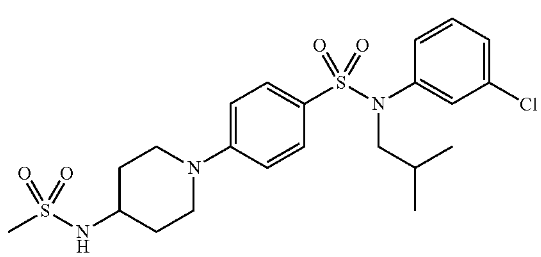 [SMILES: CC(C)CN(c1cccc(Cl)c1)S(=O)(=O)c1ccc(N2CCC(NS(C)(=O)=O)CC2)cc1] | N-(3-Chloro-phenyl)-N-isobutyl-4-(4-methanesulfonylamino-piperidin-1-yl)-benzenesulfonamide | 0.169 |

TABLE 1-continued

| | Structure | Name | (IC$_{50}$) [uM] |
|---|---|---|---|
| 24 | 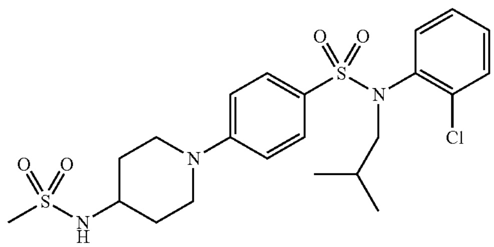 [SMILES: CC(C)CN(c1ccccc1Cl)S(=O)(=O)c1ccc(N2CCC(NS(C)(=O)=O)CC2)cc1] | N-(2-Chloro-phenyl)-N-isobutyl-4-(4-methanesulfonylamino-piperidin-1-yl)-benzenesulfonamide | 0.128 |
| 25 | 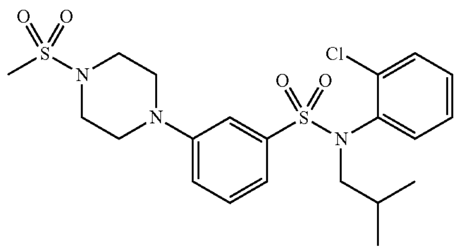 [SMILES: CC(C)CN(c1ccccc1Cl)S(=O)(=O)c1cccc(N2CCN(S(C)(=O)=O)CC2)c1] | N-(2-Chloro-phenyl)-N-isobutyl-3-(4-methanesulfonyl-piperazin-1-yl)-benzenesulfonamide | 0.528 |
| 26 | 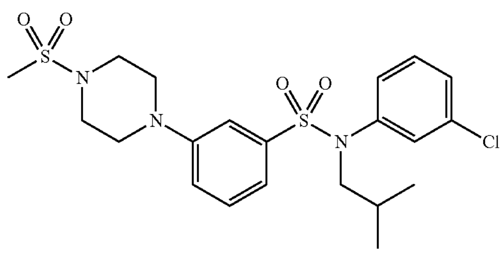 [SMILES: CC(C)CN(c1cccc(Cl)c1)S(=O)(=O)c1cccc(N2CCN(S(C)(=O)=O)CC2)c1] | N-(3-Chloro-phenyl)-N-isobutyl-3-(4-methanesulfonyl-piperazin-1-yl)-benzenesulfonamide | 0.414 |
| 27 | 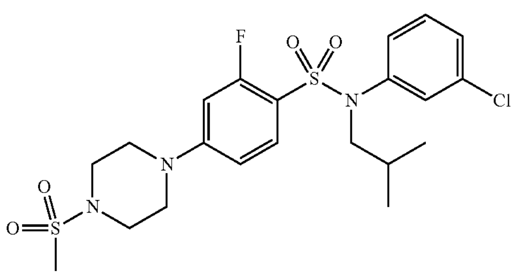 [SMILES: CC(C)CN(c1cccc(Cl)c1)S(=O)(=O)c1ccc(N2CCN(S(C)(=O)=O)CC2)cc1F] | N-(3-Chloro-phenyl)-2-fluoro-N-isobutyl-4-(4-methanesulfonyl-piperazin-1-yl)-benzenesulfonamide | 0.033 |
| 28 | 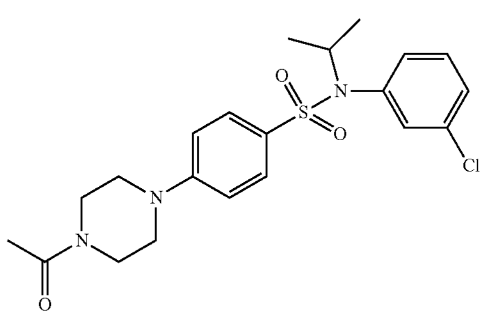 [SMILES: CC(=O)N1CCN(c2ccc(S(=O)(=O)N(c3cccc(Cl)c3)C(C)C)cc2)CC1] | 4-(4-Acetyl-piperazin-1-yl)-N-(3-chloro-phenyl)-N-isopropyl-benzenesulfonamide | 1.6 |

TABLE 1-continued

| | Structure | Name | (IC$_{50}$) [uM] |
|---|---|---|---|
| 29 | 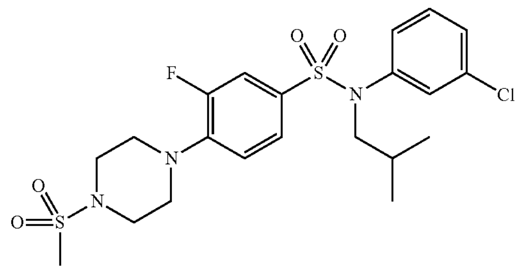 [SMILES: CC(C)CN(c1cccc(Cl)c1)S(=O)(=O)c1ccc(N2CCN(S(C)(=O)=O)CC2)c(F)c1] | N-(3-Chloro-phenyl)-3-fluoro-N-isobutyl-4-(4-methanesulfonyl-piperazin-1-yl)-benzenesulfonamide | 0.036 |
| 30 | 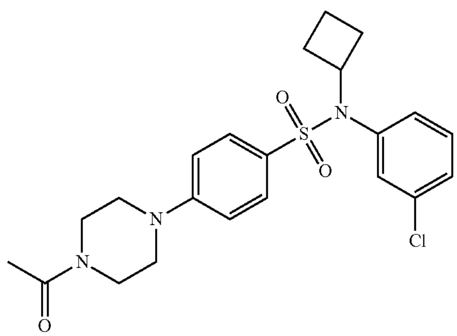 [SMILES: CC(=O)N1CCN(c2ccc(S(=O)(=O)N(c3cccc(Cl)c3)C3CCC3)cc2)CC1] | 4-(4-Acetyl-piperazin-1-yl)-N-(3-chloro-phenyl)-N-cyclobutyl-benzenesulfonamide | 0.149 |
| 31 | 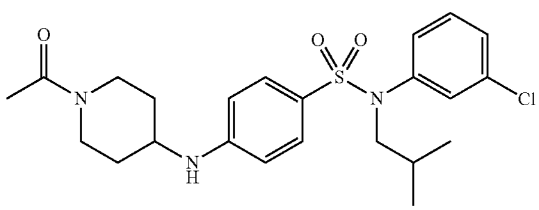 [SMILES: CC(=O)N1CCC(Nc2ccc(S(=O)(=O)N(CC(C)C)c3cccc(Cl)c3)cc2)CC1] | 4-(1-Acetyl-piperidin-4-ylamino)-N-(3-chloro-phenyl)-N-isobutyl-benzenesulfonamide | 0.258 |
| 32 | 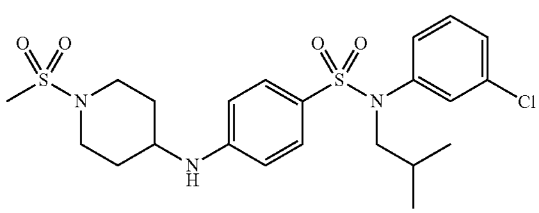 [SMILES: CC(C)CN(c1cccc(Cl)c1)S(=O)(=O)c1ccc(NC2CCN(S(C)(=O)=O)CC2)cc1] | N-(3-Chloro-phenyl)-N-isobutyl-4-(1-methanesulfonyl-piperidin-4-ylamino)-benzenesulfonamide | 0.007 |
| 33 | 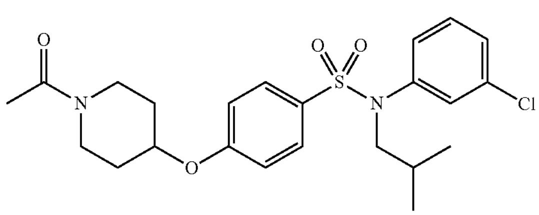 [SMILES: CC(=O)N1CCC(Oc2ccc(S(=O)(=O)N(CC(C)C)c3cccc(Cl)c3)cc2)CC1] | 4-(1-Acetyl-piperidin-4-yloxy)-N-(3-chloro-phenyl)-N-isobutyl-benzenesulfonamide | 0.198 |
| 34 | 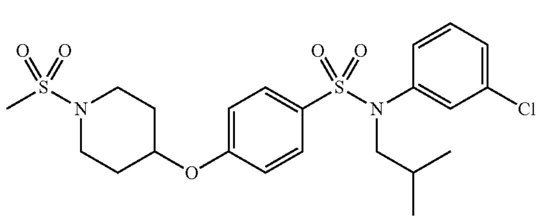 [SMILES: CC(C)CN(c1cccc(Cl)c1)S(=O)(=O)c1ccc(OC2CCN(S(C)(=O)=O)CC2)cc1] | N-(3-Chloro-phenyl)-N-isobutyl-4-(1-methanesulfonyl-piperidin-4-yloxy)-benzenesulfonamide | 0.008 |

TABLE 1-continued

| | Structure | Name | (IC$_{50}$) [uM] |
|---|---|---|---|
| 35 | 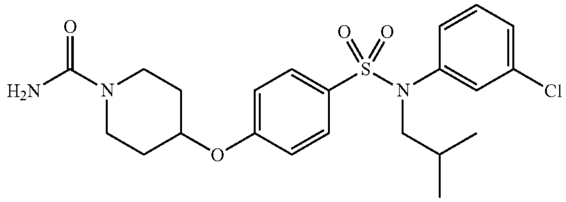 [SMILES: CC(C)CN(c1cccc(Cl)c1)S(=O)(=O)c1ccc(OC2CCN(C(N)=O)CC2)cc1] | 4-{4-[(3-Chloro-phenyl)-isobutyl-sulfamoyl]-phenoxy}-piperidine-1-carboxylic acid amide | 0.108 |
| 36 | 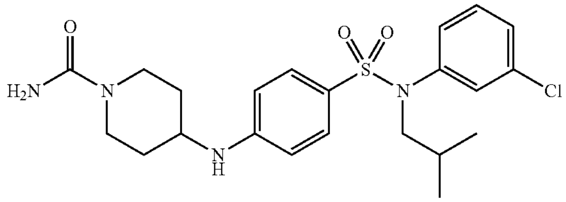 [SMILES: CC(C)CN(c1cccc(Cl)c1)S(=O)(=O)c1ccc(NC2CCN(C(N)=O)CC2)cc1] | 4-{4-[(3-Chloro-phenyl)-isobutyl-sulfamoyl]-phenylamino}-piperidine-1-carboxylic acid amide | 0.066 |
| 37 | 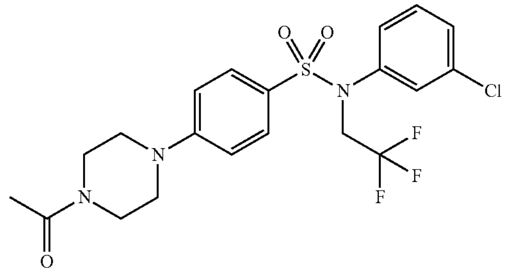 [SMILES: CC(=O)N1CCN(c2ccc(S(=O)(=O)N(CC(F)(F)F)c3cccc(Cl)c3)cc2)CC1] | 4-(4-Acetyl-piperazin-1-yl)-N-(3-chloro-phenyl)-N-(2,2,2-trifluoro-ethyl)-benzenesulfonamide | 0.305 |
| 38 | 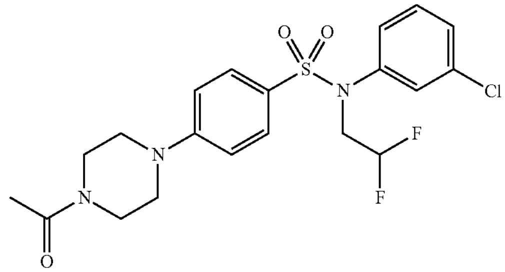 | 4-(4-Acetyl-piperazin-1-yl)-N-(3-chloro-phenyl)-N-(2,2-difluoro-ethyl)-benzenesulfonamide | 1.4 |
| 39 | 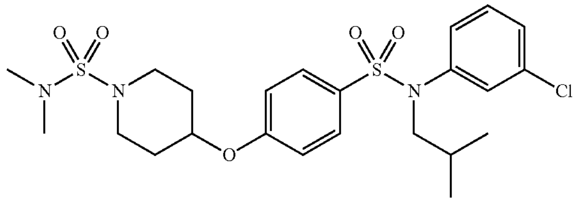 [SMILES: CC(C)CN(c1cccc(Cl)c1)S(=O)(=O)c1ccc(OC2CCN(S(=O)(=O)N(C)C)CC2)cc1] | 4-{4-[(3-Chloro-phenyl)-isobutyl-sulfamoyl]-phenoxy}-piperidine-1-sulfonic acid dimethylamide | 0.191 |
| 40 | 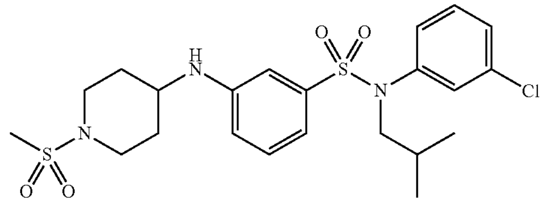 [SMILES: CC(C)CN(c1cccc(Cl)c1)S(=O)(=O)c1cccc(NC2CCN(S(C)(=O)=O)CC2)c1] | N-(3-Chloro-phenyl)-N-isobutyl-3-(1-methanesulfonyl-piperidin-4-ylamino)-benzenesulfonamide | 0.48 |

TABLE 1-continued

| | Structure | Name | (IC$_{50}$) [uM] |
|---|---|---|---|
| 41 | 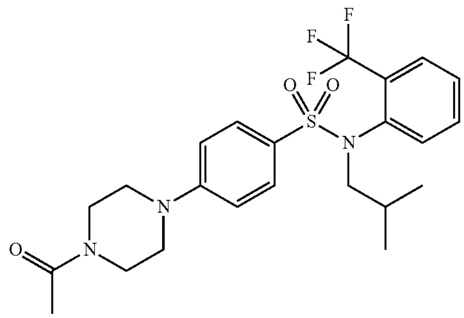 [SMILES: CC(=O)N1CCN(c2ccc(S(=O)(=O)N(CC(C)C)c3ccccc3C(F)(F)F)cc2)CC1] | 4-(4-Acetyl-piperazin-1-yl)-N-isobutyl-N-(2-trifluoromethyl-phenyl)-benzenesulfonamide | 0.028 |
| 42 | 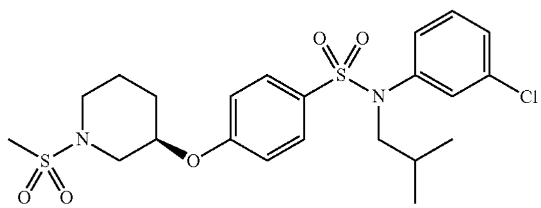 [SMILES: CC(C)CN(c1cccc(Cl)c1)S(=O)(=O)c1ccc(O[C@@H]2CCCN(S(C)(=O)=O)C2)cc1] | N-(3-Chloro-phenyl)-N-isobutyl-4-((R)-1-methanesulfonyl-piperidin-3-yloxy)-benzenesulfonamide | 0.164 |
| 43 | 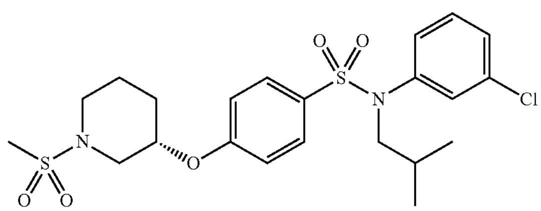 [SMILES: CC(C)CN(c1cccc(Cl)c1)S(=O)(=O)c1ccc(O[C@H]2CCCN(S(C)(=O)=O)C2)cc1] | N-(3-Chloro-phenyl)-N-isobutyl-4-((S)-1-methanesulfonyl-piperidin-3-yloxy)-benzenesulfonamide | 0.281 |
| 44 | 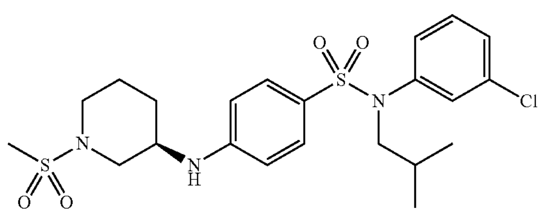 [SMILES: CC(C)CN(c1cccc(Cl)c1)S(=O)(=O)c1ccc(N[C@@H]2CCCN(S(C)(=O)=O)C2)cc1] | N-(3-Chloro-phenyl)-N-isobutyl-4-((R)-1-methanesulfonyl-piperidin-3-ylamino)-benzenesulfonamide | 0.117 |
| 45 | 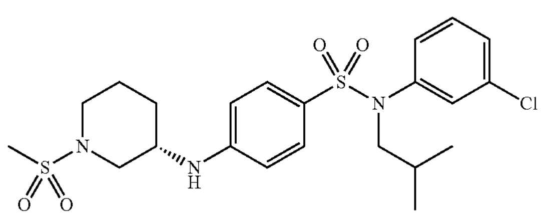 [SMILES: CC(C)CN(c1cccc(Cl)c1)S(=O)(=O)c1ccc(N[C@H]2CCCN(S(C)(=O)=O)C2)cc1] | N-(3-Chloro-phenyl)-N-isobutyl-4-((S)-1-methanesulfonyl-piperidin-3-ylamino)-benzenesulfonamide | 0.271 |
| 46 | 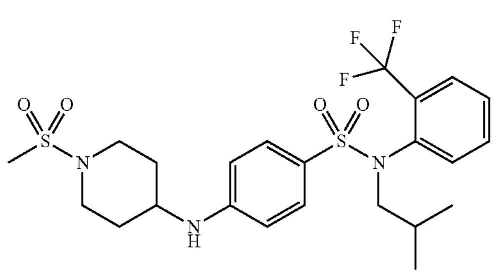 [SMILES: CC(C)CN(c1ccccc1C(F)(F)F)S(=O)(=O)c1ccc(NC2CCN(S(C)(=O)=O)CC2)cc1] | N-Isobutyl-4-(1-methanesulfonyl-piperidin-4-ylamino)-N-(2-trifluoromethyl-phenyl)-benzenesulfonamide | 0.033 |

TABLE 1-continued

| | Structure | Name | (IC$_{50}$) [uM] |
|---|---|---|---|
| 47 | 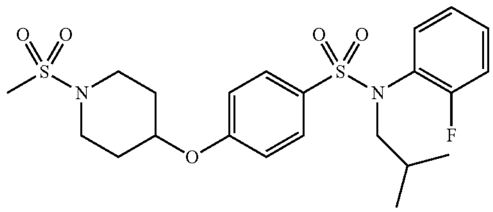 [SMILES: CC(C)CN(c1ccccc1F)S(=O)(=O)c1ccc(OC2CCN(S(C)(=O)=O)CC2)cc1] | N-(2-Fluoro-phenyl)-N-isobutyl-4-(1-methanesulfonyl-piperidin-4-yloxy)-benzenesulfonamide | 0.056 |
| 48 | 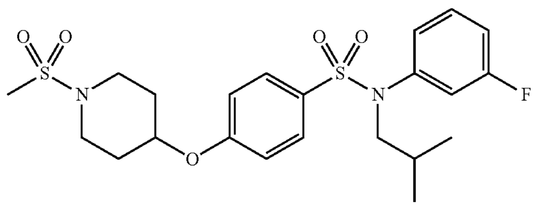 [SMILES: CC(C)CN(c1cccc(F)c1)S(=O)(=O)c1ccc(OC2CCN(S(C)(=O)=O)CC2)cc1] | N-(3-Fluoro-phenyl)-N-isobutyl-4-(1-methanesulfonyl-piperidin-4-yloxy)-benzenesulfonamide | 0.008 |
| 49 | 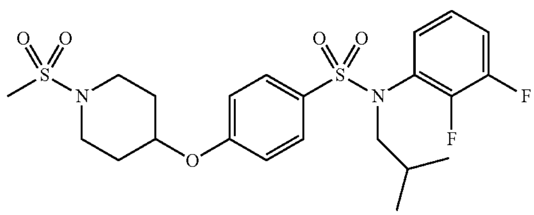 [SMILES: CC(C)CN(c1cccc(F)c1F)S(=O)(=O)c1ccc(OC2CCN(S(C)(=O)=O)CC2)cc1] | N-(2,3-Difluoro-phenyl)-N-isobutyl-4-(1-methanesulfonyl-piperidin-4-yloxy)-benzenesulfonamide | 0.008 |
| 50 | 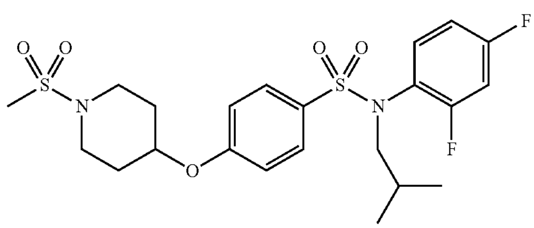 [SMILES: CC(C)CN(c1ccc(F)cc1F)S(=O)(=O)c1ccc(OC2CCN(S(C)(=O)=O)CC2)cc1] | N-(2,4-Difluoro-phenyl)-N-isobutyl-4-(1-methanesulfonyl-piperidin-4-yloxy)-benzenesulfonamide | 0.009 |
| 51 | 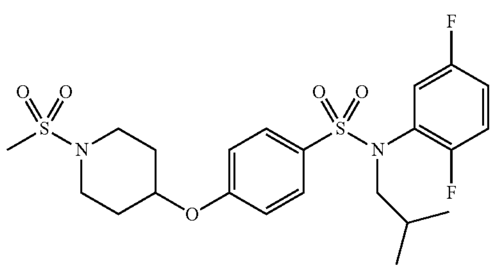 [SMILES: CC(C)CN(c1cc(F)ccc1F)S(=O)(=O)c1ccc(OC2CCN(S(C)(=O)=O)CC2)cc1] | N-(2,5-Difluoro-phenyl)-N-isobutyl-4-(1-methanesulfonyl-piperidin-4-yloxy)-benzenesulfonamide | 0.008 |
| 52 | 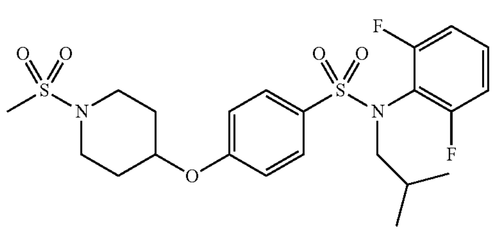 [SMILES: CC(C)CN(c1c(F)cccc1F)S(=O)(=O)c1ccc(OC2CCN(S(C)(=O)=O)CC2)cc1] | N-(2,6-Difluoro-phenyl)-N-isobutyl-4-(1-methanesulfonyl-piperidin-4-yloxy)-benzenesulfonamide | 0.011 |
| 53 | 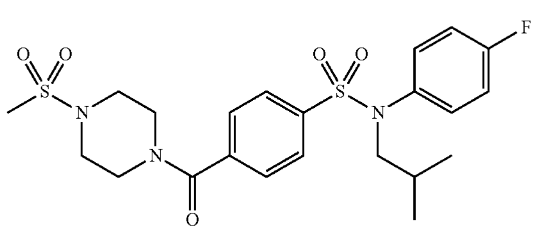 [SMILES: CC(C)CN(c1ccc(F)cc1)S(=O)(=O)c1ccc(C(=O)N2CCN(S(C)(=O)=O)CC2)cc1] | N-(4-Fluoro-phenyl)-N-isobutyl-4-(4-methanesulfonyl-piperazine-1-carbonyl)-benzenesulfonamide | 0.299 |

TABLE 1-continued

| | Structure | Name | (IC$_{50}$) [uM] |
|---|---|---|---|
| 54 | 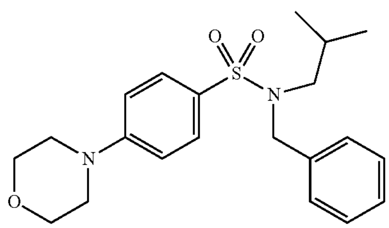 [SMILES: CC(C)CN(Cc1ccccc1)S(=O)(=O)c1ccc(N2CCOCC2)cc1] | N-Benzyl-N-isobutyl-4-morpholin-4-yl-benzenesulfonamide | 0.511 |
| 55 | 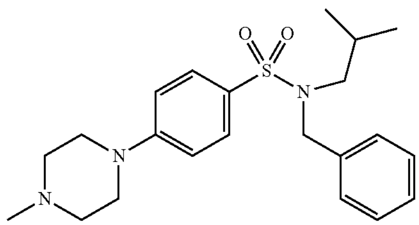 [SMILES: CC(C)CN(Cc1ccccc1)S(=O)(=O)c1ccc(N2CCN(C)CC2)cc1] | N-Benzyl-N-isobutyl-4-(4-methyl-piperazin-1-yl)-benzenesulfonamide | 5.6 |
| 56 | 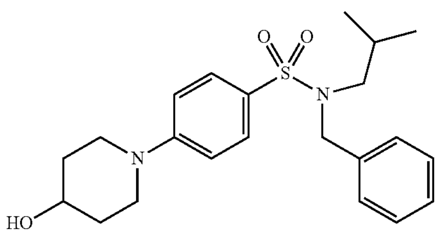 [SMILES: CC(C)CN(Cc1ccccc1)S(=O)(=O)c1ccc(N2CCC(O)CC2)cc1] | N-Benzyl-4-(4-hydroxy-piperidin-1-yl)-N-isobutyl-benzenesulfonamide | 0.438 |
| 57 | 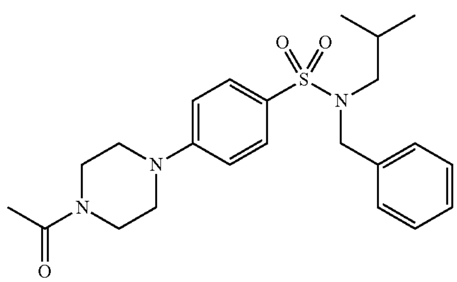 [SMILES: CC(=O)N1CCN(c2ccc(S(=O)(=O)N(Cc3ccccc3)CC(C)C)cc2)CC1] | 4-(4-Acetyl-piperazin-1-yl)-N-benzyl-N-isobutyl-benzenesulfonamide | 0.417 |
| 58 | 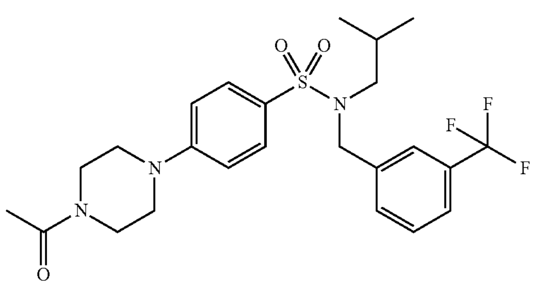 [SMILES: CC(=O)N1CCN(c2ccc(S(=O)(=O)N(Cc3cccc(C(F)(F)F)c3)CC(C)C)cc2)CC1] | 4-(4-Acetyl-piperazin-1-yl)-N-isobutyl-N-(3-trifluoromethyl-benzyl)-benzenesulfonamide | 0.244 |
| 59 | 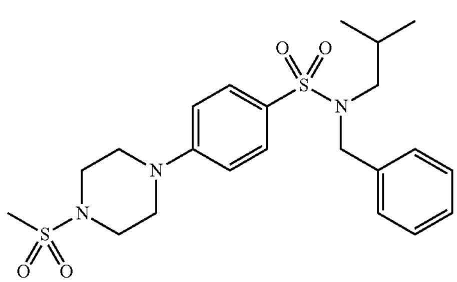 [SMILES: CC(C)CN(Cc1ccccc1)S(=O)(=O)c1ccc(N2CCN(S(C)(=O)=O)CC2)cc1] | N-Benzyl-N-isobutyl-4-(4-methanesulfonyl-piperazin-1-yl)-benzenesulfonamide | 0.366 |

TABLE 1-continued

| | Structure | Name | (IC$_{50}$) [uM] |
|---|---|---|---|
| 60 | 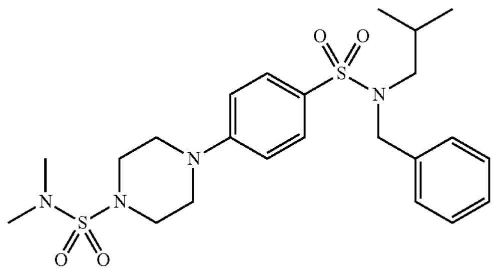 [SMILES: CC(C)CN(Cc1ccccc1)S(=O)(=O)c1ccc(N2CCN(S(=O)(=O)N(C)C)CC2)cc1] | 4-[4-(Benzyl-isobutyl-sulfamoyl)-phenyl]-piperazine-1-sulfonic acid dimethylamide | 0.174 |
| 61 | 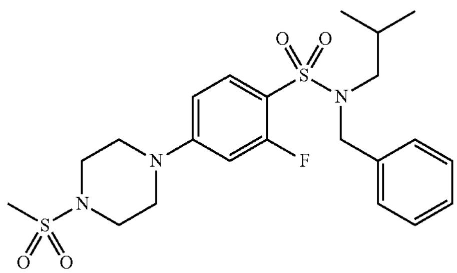 [SMILES: CC(C)CN(Cc1ccccc1)S(=O)(=O)c1ccc(N2CCN(S(C)(=O)=O)CC2)cc1F] | N-Benzyl-2-fluoro-N-isobutyl-4-(4-methanesulfonyl-piperazin-1-yl)-benzenesulfonamide | 0.093 |
| 62 | 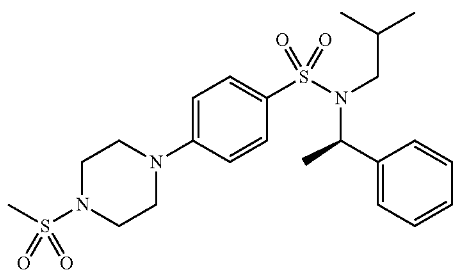 [SMILES: CC(C)CN([C@H](C)c1ccccc1)S(=O)(=O)c1ccc(N2CCN(S(C)(=O)=O)CC2)cc1] | N-Isobutyl-4-(4-methanesulfonyl-piperazin-1-yl)-N-((R)-1-phenyl-ethyl)-benzenesulfonamide | 0.483 |
| 63 | 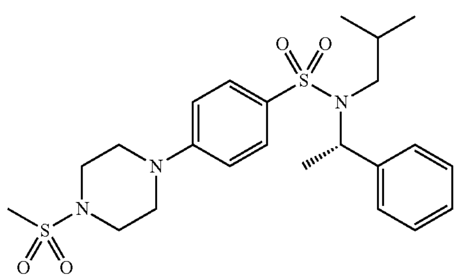 [SMILES: CC(C)CN([C@@H](C)c1ccccc1)S(=O)(=O)c1ccc(N2CCN(S(C)(=O)=O)CC2)cc1] | N-Isobutyl-4-(4-methanesulfonyl-piperazin-1-yl)-N-((S)-1-phenyl-ethyl)-benzenesulfonamide | 0.039 |
| 64 | 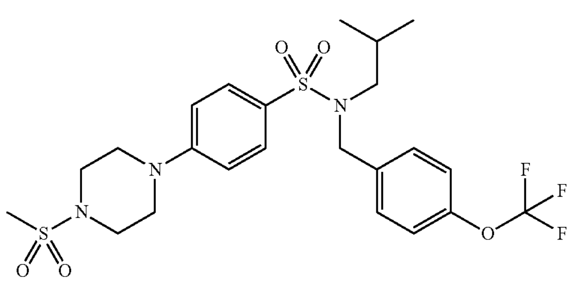 [SMILES: CC(C)CN(Cc1ccc(OC(F)(F)F)cc1)S(=O)(=O)c1ccc(N2CCN(S(C)(=O)=O)CC2)cc1] | N-Isobutyl-4-(4-methanesulfonyl-piperazin-1-yl)-N-(4-trifluoromethoxy-benzyl)-benzenesulfonamide | 0.102 |

TABLE 1-continued

| | Structure | Name | (IC$_{50}$) [uM] |
|---|---|---|---|
| 65 | 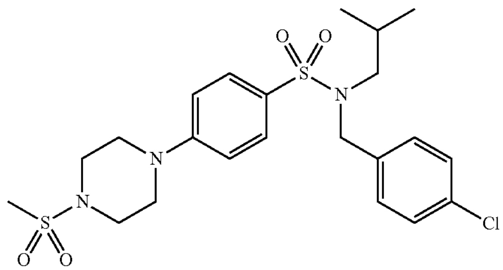 [SMILES: CC(C)CN(Cc1ccc(Cl)cc1)S(=O)(=O)c1ccc(N2CCN(S(C)(=O)=O)CC2)cc1] | N-(4-Chloro-benzyl)-N-isobutyl-4-(4-methanesulfonyl-piperazin-1-yl)-benzenesulfonamide | 0.061 |
| 66 | 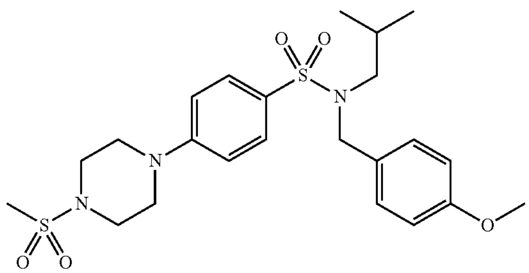 | N-Isobutyl-4-(4-methanesulfonyl-piperazin-1-yl)-N-(4-methoxy-benzyl)-benzenesulfonamide | 0.079 |
| 67 | 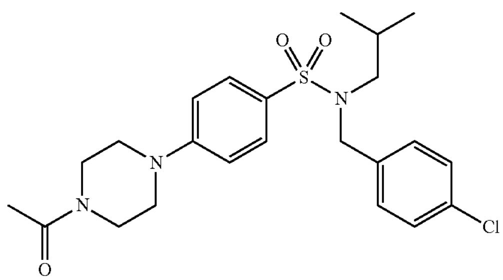 [SMILES: CC(=O)N1CCN(c2ccc(S(=O)(=O)N(Cc3ccc(Cl)cc3)CC(C)C)cc2)CC1] | 4-(4-Acetyl-piperazin-1-yl)-N-(4-chloro-benzyl)-N-isobutyl-benzenesulfonamide | 0.087 |
| 68 | 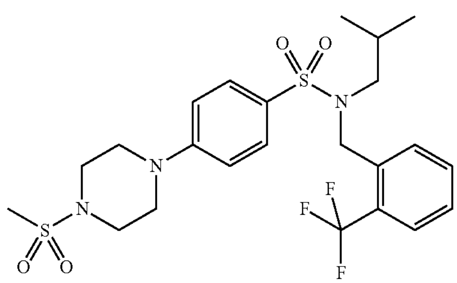 [SMILES: CC(C)CN(Cc1ccccc1C(F)(F)F)S(=O)(=O)c1ccc(N2CCN(S(C)(=O)=O)CC2)cc1] | N-Isobutyl-4-(4-methanesulfonyl-piperazin-1-yl)-N-(2-trifluoromethyl-benzyl)-benzenesulfonamide | 0.034 |
| 69 | 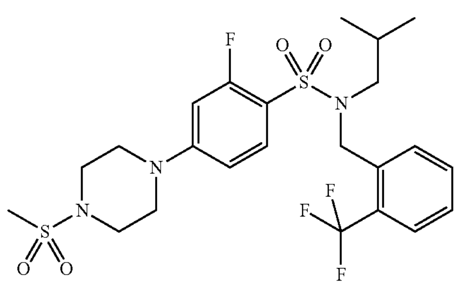 [SMILES: CC(C)CN(Cc1ccccc1C(F)(F)F)S(=O)(=O)c1ccc(N2CCN(S(C)(=O)=O)CC2)cc1F] | 2-Fluoro-N-isobutyl-4-(4-methanesulfonyl-piperazin-1-yl)-N-(2-trifluoromethyl-benzyl)-benzenesulfonamide | 0.02 |

TABLE 1-continued

| | Structure | Name | (IC$_{50}$) [uM] |
|---|---|---|---|
| 70 | 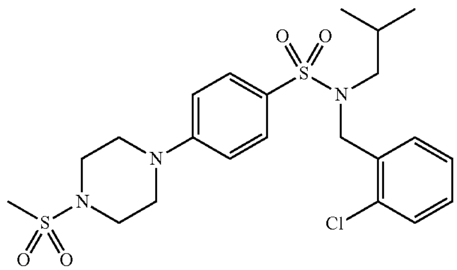 [SMILES: CC(C)CN(Cc1ccccc1Cl)S(=O)(=O)c1ccc(N2CCN(S(C)(=O)=O)CC2)cc1] | N-(2-Chloro-benzyl)-N-isobutyl-4-(4-methanesulfonyl-piperazin-1-yl)-benzenesulfonamide | 0.021 |
| 71 | 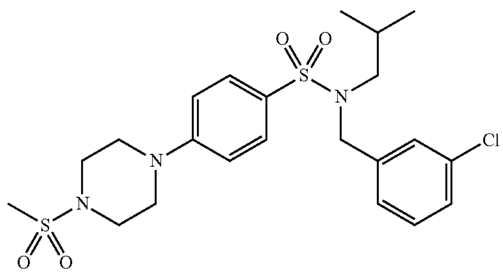 [SMILES: CC(C)CN(Cc1cccc(Cl)c1)S(=O)(=O)c1ccc(N2CCN(S(C)(=O)=O)CC2)cc1] | N-(3-Chloro-benzyl)-N-isobutyl-4-(4-methanesulfonyl-piperazin-1-yl)-benzenesulfonamide | 0.07 |
| 72 | 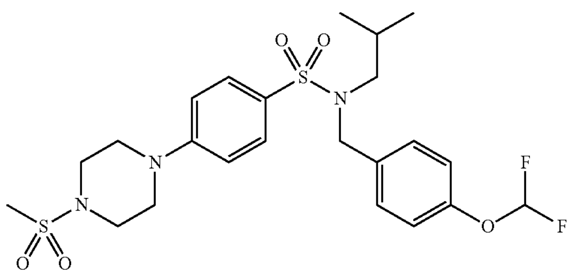 [SMILES: CC(C)CN(Cc1ccc(OC(F)F)cc1)S(=O)(=O)c1ccc(N2CCN(S(C)(=O)=O)CC2)cc1] | N-(4-Difluoromethoxy-benzyl)-N-isobutyl-4-(4-methanesulfonyl-piperazin-1-yl)-benzenesulfonamide | 0.083 |
| 73 | 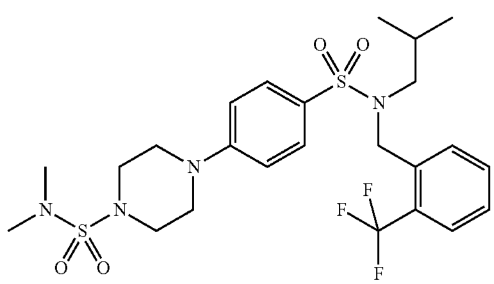 [SMILES: CC(C)CN(Cc1ccccc1C(F)(F)F)S(=O)(=O)c1ccc(N2CCN(S(=O)(=O)N(C)C)CC2)cc1] | 4-{4-[Isobutyl-(2-trifluoromethyl-benzyl)-sulfamoyl]-phenyl}-piperazine-1-sulfonic acid dimethylamide | 0.023 |
| 74 | 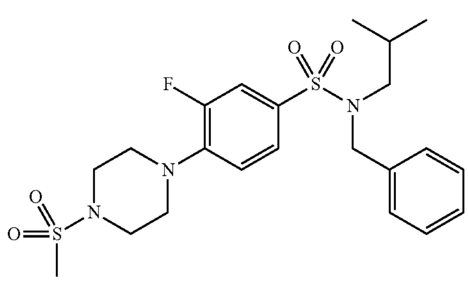 [SMILES: CC(C)CN(Cc1ccccc1)S(=O)(=O)c1ccc(N2CCN(S(C)(=O)=O)CC2)c(F)c1] | N-Benzyl-3-fluoro-N-isobutyl-4-(4-methanesulfonyl-piperazin-1-yl)-benzenesulfonamide | 0.051 |

TABLE 1-continued

| | Structure | Name | (IC$_{50}$) [uM] |
|---|---|---|---|
| 75 | 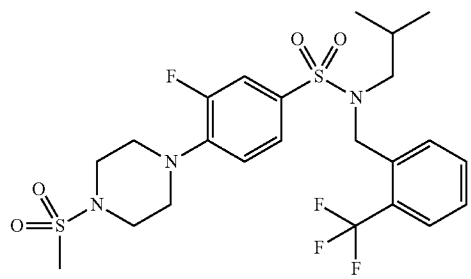 [SMILES: CC(C)CN(Cc1ccccc1C(F)(F)F)S(=O)(=O)c1ccc(N2CCN(S(C)(=O)=O)CC2)c(F)c1] | 3-Fluoro-N-isobutyl-4-(4-methanesulfonyl-piperazin-1-yl)-N-(2-trifluoromethyl-benzyl)-benzenesulfonamide | 0.008 |
| 76 | 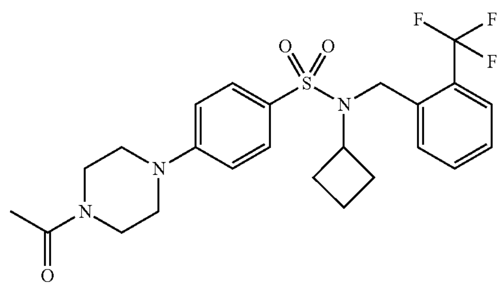 [SMILES: CC(=O)N1CCN(c2ccc(S(=O)(=O)N(Cc3ccccc3C(F)(F)F)C3CCC3)cc2)CC1] | 4-(4-Acetyl-piperazin-1-yl)-N-cyclobutyl-N-(2-trifluoromethyl-benzyl)-benzenesulfonamide | 0.031 |
| 77 | 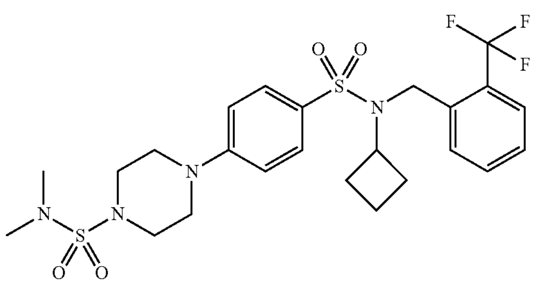 [SMILES: CN(C)S(=O)(=O)N1CCN(c2ccc(S(=O)(=O)N(Cc3ccccc3C(F)(F)F)C3CCC3)cc2)CC1] | 4-{4-[Cyclobutyl-(2-trifluoromethyl-benzyl)-sulfamoyl]-phenyl}-piperazine-1-sulfonic acid dimethylamide | 0.025 |
| 78 | 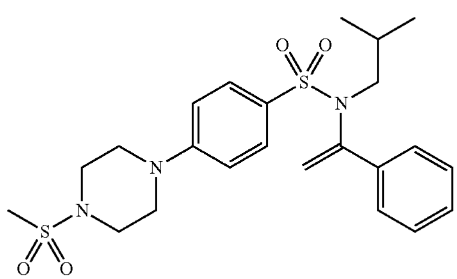 [SMILES: C=C(c1ccccc1)N(CC(C)C)S(=O)(=O)c1ccc(N2CCN(S(C)(=O)=O)CC2)cc1] | N-Isobutyl-4-(4-methanesulfonyl-piperazin-1-yl)-N-(1-phenyl-vinyl)-benzenesulfonamide | 0.023 |
| 79 | 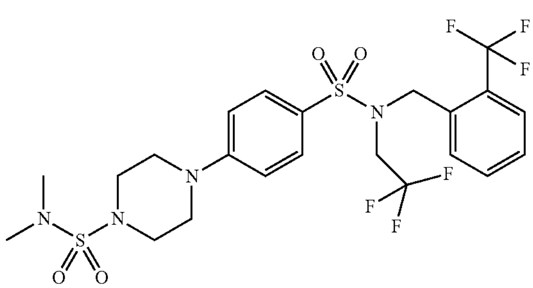 [SMILES: CN(C)S(=O)(=O)N1CCN(c2ccc(S(=O)(=O)N(Cc3ccccc3C(F)(F)F)CC(F)(F)F)cc2)CC1] | 4-{4-[(2,2,2-Trifluoro-ethyl)-(2-trifluoromethyl-benzyl)-sulfamoyl]-phenyl}-piperazine-1-sulfonic acid dimethylamide | 0.055 |

TABLE 1-continued

| | Structure | Name | (IC$_{50}$) [uM] |
|---|---|---|---|
| 80 | 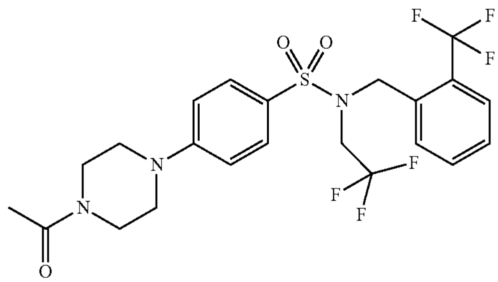 [SMILES: CC(=O)N1CCN(c2ccc(S(=O)(=O)N(Cc3ccccc3C(F)(F)F)CC(F)(F)F)cc2)CC1] | 4-(4-Acetyl-piperazin-1-yl)-N-(2,2,2-trifluoro-ethyl)-N-(2-trifluoromethyl-benzyl)-benzenesulfonamide | 0.087 |
| 81 | 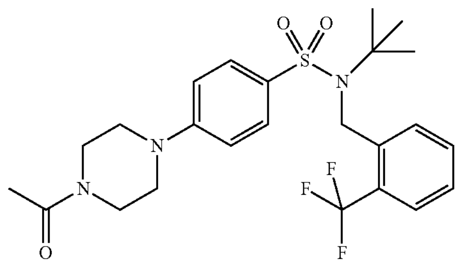 [SMILES: CC(=O)N1CCN(c2ccc(S(=O)(=O)N(Cc3ccccc3C(F)(F)F)C(C)(C)C)cc2)CC1] | 4-(4-Acetyl-piperazin-1-yl)-N-tert-butyl-N-(2-trifluoromethyl-benzyl)-benzenesulfonamide | 0.11 |
| 82 | 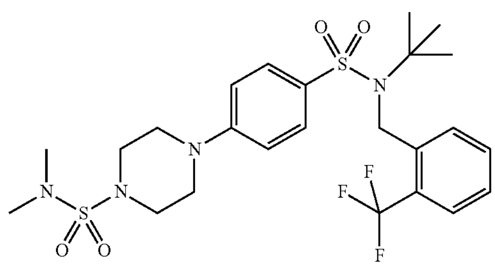 [SMILES: CN(C)S(=O)(=O)N1CCN(c2ccc(S(=O)(=O)N(Cc3ccccc3C(F)(F)F)C(C)(C)C)cc2)CC1] | 4-{4-[tert-Butyl-(2-trifluoromethyl-benzyl)-sulfamoyl]-phenyl}-piperazine-1-sulfonic acid dimethylamide | 0.051 |
| 83 | 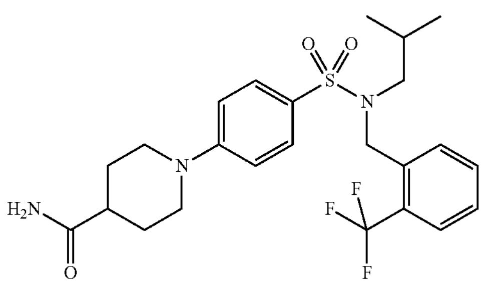 [SMILES: CC(C)CN(Cc1ccccc1C(F)(F)F)S(=O)(=O)c1ccc(N2CCC(C(N)=O)CC2)cc1] | 1-{4-[Isobutyl-(2-trifluoromethyl-benzyl)-sulfamoyl]-phenyl}-piperidine-4-carboxylic acid amide | 0.024 |
| 84 | 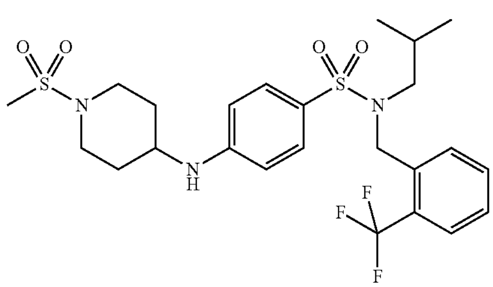 [SMILES: CC(C)CN(Cc1ccccc1C(F)(F)F)S(=O)(=O)c1ccc(NC2CCN(S(C)(=O)=O)CC2)cc1] | N-Isobutyl-4-(1-methanesulfonyl-piperidin-4-ylamino)-N-(2-trifluoromethyl-benzyl)-benzenesulfonamide | 0.006 |

TABLE 1-continued

| | Structure | Name | (IC$_{50}$) [uM] |
|---|---|---|---|
| 85 | 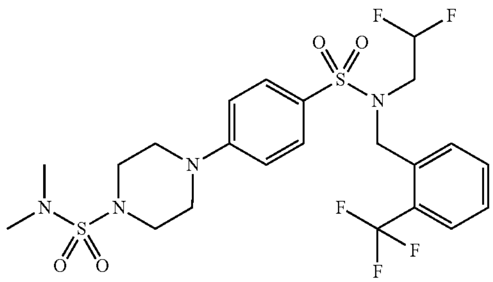 [SMILES: CN(C)S(=O)(=O)N1CCN(c2ccc(S(=O)(=O)N(Cc3ccccc3C(F)(F)F)CC(F)F)cc2)CC1] | 4-{4-[(2,2-Difluoro-ethyl)-(2-trifluoromethyl-benzyl)-sulfamoyl]-phenyl}-piperazine-1-sulfonic acid dimethylamide | 0.116 |
| 86 | 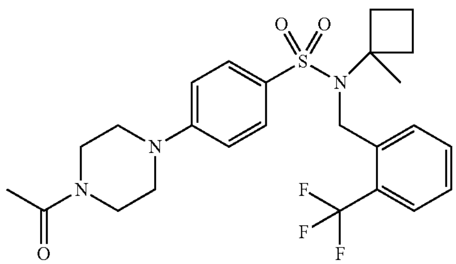 [SMILES: CC(=O)N1CCN(c2ccc(S(=O)(=O)N(Cc3ccccc3C(F)(F)F)C3(C)CCC3)cc2)CC1] | 4-(4-Acetyl-piperazin-1-yl)-N-(1-methyl-cyclobutyl)-N-(2-trifluoromethyl-benzyl)-benzenesulfonamide | 0.07 |
| 87 | 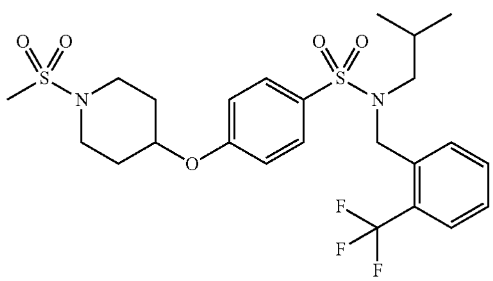 [SMILES: CC(C)CN(Cc1ccccc1C(F)(F)F)S(=O)(=O)c1ccc(OC2CCN(S(C)(=O)=O)CC2)cc1] | N-Isobutyl-4-(1-methanesulfonyl-piperidin-4-yloxy)-N-(2-trifluoromethyl-benzyl)-benzenesulfonamide | 0.006 |
| 88 | 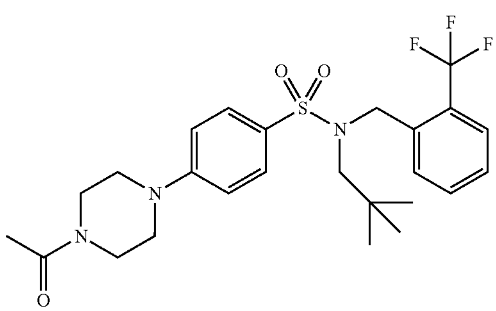 [SMILES: CC(=O)N1CCN(c2ccc(S(=O)(=O)N(Cc3ccccc3C(F)(F)F)CC(C)(C)C)cc2)CC1] | 4-(4-Acetyl-piperazin-1-yl)-N-(2,2-dimethyl-propyl)-N-(2-trifluoromethyl-benzyl)-benzenesulfonamide | 0.039 |
| 89 | 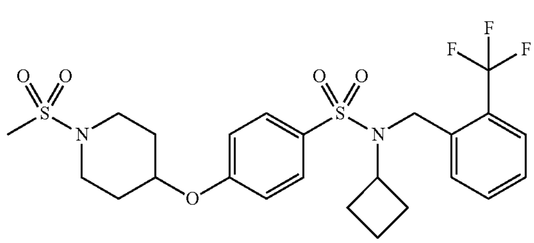 [SMILES: CS(=O)(=O)N1CCC(Oc2ccc(S(=O)(=O)N(Cc3ccccc3C(F)(F)F)C3CCC3)cc2)CC1] | N-Cyclobutyl-4-(1-methanesulfonyl-piperidin-4-yloxy)-N-(2-trifluoromethyl-benzyl)-benzenesulfonamide | 0.009 |

TABLE 1-continued

| | Structure | Name | (IC$_{50}$) [uM] |
|---|---|---|---|
| 90 | 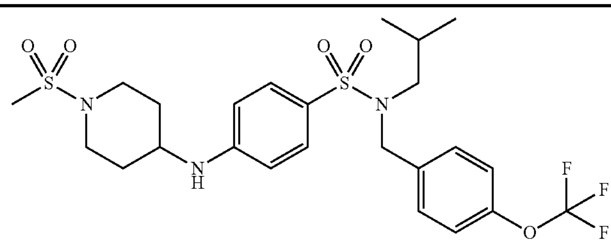 | N-Isobutyl-4-(1-methanesulfonyl-piperidin-4-ylamino)-N-(4-trifluoromethoxy-benzyl)-benzenesulfonamide | 0.011 |
| 91 | 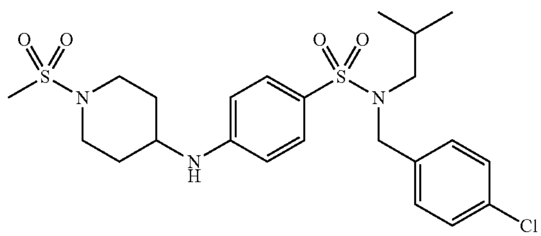 [SMILES: CC(C)CN(Cc1ccc(Cl)cc1)S(=O)(=O)c1ccc(NC2CCN(S(C)(=O)=O)CC2)cc1] | N-(4-Chloro-benzyl)-N-isobutyl-4-(1-methanesulfonyl-piperidin-4-ylamino)-benzenesulfonamide | 0.01 |
| 92 | 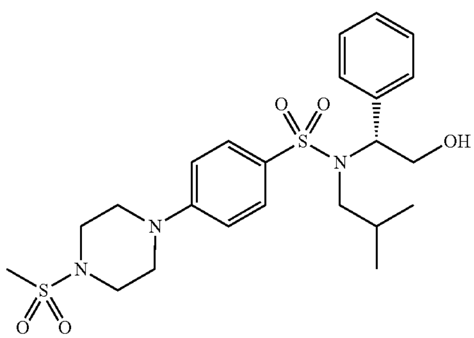 [SMILES: CC(C)CN([C@@H](CO)c1ccccc1)S(=O)(=O)c1ccc(N2CCN(S(C)(=O)=O)CC2)cc1] | N-((R)-2-Hydroxy-1-phenyl-ethyl)-N-isobutyl-4-(4-methanesulfonyl-piperazin-1-yl)-benzenesulfonamide | 3.1 |

Example 15

In Vitro RORc Ligand Binding Assay

This assay was used to determine a compound's potency in inhibiting activity of RORc by determining, Ki$_{app}$, IC$_{50}$, or percent inhibition values. Consumables used in this Example are shown in Table 2 below.

TABLE 2

| Consumable | Supplier and product code |
|---|---|
| GFB Unifilter plates | Perkin Elmer 6005177 |
| 3-[(3-Cholamidopropyl)dimethylammonio]-1-propanesulfonate (CHAPS) | Sigma C5070 |
| 96-well polypropylene U-bottom assay plate | Nunc 267245 |
| HEPES buffer, 1M | Sigma H3375 |
| Magnesium chloride (MgCl$_2$) | Sigma M8266 |
| D,L-Dithiothreitol (DTT) | Sigma D0632 |
| Sodium chloride (NaCl) | Sigma 71382 |
| Bovine serum albumin (BSA) | Sigma A7030 [lyophilized powder, ≥98% (agarose gel electrophoresis), Essentially fatty acid free, essentially globulin free] |
| 25-hydroxycholesterol | Sigma H1015 |
| 25-[26,27-$^3$H]hydroxycholesterol | Perkin Elmer NET674250UC American Radiolabeled Chemicals ART0766 |

TABLE 2-continued

| Consumable | Supplier and product code |
|---|---|
| RORc ligand binding domain | Genentech (e.g., PUR 28048), expressed in E. coli |
| Plate seals | Perkin Elmer 6005185 |
| Microscint 0 | Perkin Elmer 6013611 |

Filter Plate Preparation

On day of the assay, 100 uL of 0.05% CHAPS (in deionized H$_2$O) was added to all wells of the GFB Unifilter plate and allowed soak for 1 h. A wash buffer of 50 mM HEPES (pH 7.4), 150 mM NaCl, and 5 mM MgCl$_2$ was prepared to wash the filter plate. To prepare an assay buffer, BSA was added to the wash buffer to reach 0.01% and DTT was added to reach 1 mM.

Compounds

For IC$_{50}$ mode, 10 mM compound stocks were serially diluted in DMSO with DMSO to give 20× required final concentration in DMSO (15 uL compound+30 uL DMSO). The 20× compound stocks were diluted in DMSO with Assay Buffer 4-fold to reach 5× the final test concentration in 25% DMSO (10 uL compound+30 uL Assay Buffer). Solutions were mixed by aspiration several times with a pipette set on 50 uL volume. For the assay, 10 uL of 5× compound stock solutions in 25% DMSO were added to the assay plate in duplicate.

For two point screening, 10 mM stock compound solutions were diluted in DMSO to obtain 200 uM (20× the high test concentration) and then diluted 10-fold further to reach 20 uM (20× the low test concentration). The 20× stocks were diluted 4-fold with Assay Buffer (10 uL compound+30 uL Assay Buffer) to reach 5× the test concentrations (50 uM and 5 uM) and 10 uL were added to two assay plates for the duplicate wells. With each concentration tested on 2 plates, each set of 80 compounds used 4 assay plates (1 uM and 10 uM, with n=2).

Nonspecific Binding (NSB) Samples, Total Binding (TB) Samples and No Receptor (No R) Samples 25-hydroxycholesterol (1 uM) was used to determine the level of NSB signal is prepared in DMSO as for compounds above, then diluted in Assay Buffer to give a final concentration of 5 uM. For 25-hydroxycholesterol in 25% DMSO/75% Assay Buffer; 10 uL per well was used for NSB samples. Wells for Total Binding and No Receptor sample determination contained 10 uL of 25% DMSO/75% Assay Buffer per well.

Radioligand (25-[³H]hydroxycholesterol) Preparation

25-[³H]hydroxycholesterol was diluted in Assay Buffer to obtain 15 nM and vortex to mix. Add 20 uL to all wells to reach 6 nM final concentration in the assay.

Receptor Preparation

The optimal concentration for RORc receptor was found to be 0.6 ug/mL. Stock receptor solution was diluted in assay buffer to obtain 1.5 ug/mL in Assay Buffer. 20 uL was added to all wells. For No Receptor samples, 20 uL Assay Buffer was substituted for receptor solution.

Sample Addition to Plates and Incubation

Assay plates were 96-well polypropylene V-bottom plates. 10 uL of 5× compound in 25% DMSO/75% Assay Buffer was added to Test wells. 10 uL of 25% DMSO/75% Assay Buffer was added to Total Binding or No Receptor wells. 10 uL of 5 uM 25-hydroxycholesterol in 25% DMSO/75% Assay Buffer was added to NSB wells. 20 uL of 15 nM 25-[³H]hydroxycholesterol prepared in Assay Buffer was added to all wells. 20 uL of 1.5 ug/mL RORc receptor was added to wells (or 40 uL Assay Buffer to No R wells). Following addition to the wells, the plates were incubated 3 h at 25° C.

Filtration

Using a Packard Filtermate Harvester, the filter plate were washed 4 times following transfer of the incubated samples. Plates were dry-filtered completely (2 h at 50° C. or overnight at room temperature). 50 uL Microscint 0 was added to all wells and read on Topcount protocol Inverted.

Final Concentrations

Final concentrations were as follows: 50 mM HEPES buffer (pH 7.4); 150 mM NaCl; 1 mM DTT; 5 mM $MgCl_2$; 0.01% BSA; 5% DMSO; 0.6 ug/mL RORc receptor; 6 nM 25-[³H]hydroxycholesterol. For NSB wells, 1 uM 25-hydroxycholesterol was also present.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula VIII

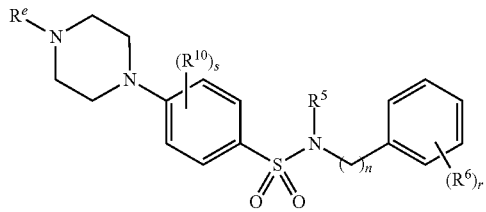

or a pharmaceutically acceptable salt thereof,
wherein:
  n is 1;
  r is from 0 to 3;
  s is from 0 to 2;
  $R^5$ is: $C_{1-6}$alkyl; $C_{3-6}$cycloalkyl; $C_{3-6}$cycloalkyl-$C_{1-6}$alkyl; $C_{1-6}$alkoxy-$C_{1-6}$alkyl; or hydroxy-$C_{1-6}$ alkyl, wherein the $C_{1-6}$ alkyl and $C_{3-6}$ cycloalkyl moieties may be substituted one or more times with halo;
  each $R^6$ is independently: $C_{1-6}$alkyl; halo; $C_{1-6}$alkoxy; or cyano; wherein the $C_{1-6}$alkyl moieties may be unsubstituted or substituted one or more times with halo;
  each $R^{10}$ is independently: $C_{1-6}$alkyl; halo; $C_{1-6}$alkoxy; or halo-$C_{1-6}$alkyl; and
  $R^e$ is: hydrogen; $C_{1-6}$alkyl-carbonyl; $C_{3-6}$cycloalkyl-carbonyl; $C_{3-6}$cycloalkyl-$C_{1-6}$ alkyl-carbonyl; $C_{1-6}$ alkyl-sulfonyl; $C_{3-6}$ cycloalkyl-sulfonyl; $C_{3-6}$ cycloalkyl-$C_{1-6}$ alkyl-sulfonyl; aminocarbonyl; N—$C_{1-6}$ alkyl-aminocarbonyl; N,N-di-$C_{1-6}$ alkyl-aminocarbonyl; aminosulfonyl; N—$C_{1-6}$alkyl-aminosulfonyl; or N,N-di-$C_{1-6}$alkyl-aminosulfonyl.

2. The compound of claim 1, wherein $R^6$ is halo or trifluoromethyl.

3. The compound of claim 1, wherein $R^e$ is: acetyl; or methanesulfonyl.

4. The compound of claim 1, wherein $R^e$ is acetyl.

5. The compound of claim 1, wherein $R^e$ is methanesulfonyl.

* * * * *